(12) United States Patent
Ismagilov et al.

(10) Patent No.: US 11,624,062 B2
(45) Date of Patent: Apr. 11, 2023

(54) METHODS AND SYSTEMS FOR PERFORMING SINGLE CELL ANALYSIS OF MOLECULES AND MOLECULAR COMPLEXES

(71) Applicant: CALIFORNIA INSTITUTE OF TECHNOLOGY, Pasadena, CA (US)

(72) Inventors: Rustem F. Ismagilov, Pasadena, CA (US); Matthew S. Curtis, Pasadena, CA (US); Mary Arrastia, Pasadena, CA (US); David A. Selck, Pasadena, CA (US); Mitchell Guttman, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/141,901

(22) Filed: Sep. 25, 2018

(65) Prior Publication Data

US 2019/0144854 A1 May 16, 2019

Related U.S. Application Data

(60) Provisional application No. 62/562,894, filed on Sep. 25, 2017, provisional application No. 62/562,684, filed on Sep. 25, 2017.

(51) Int. Cl.

| | |
|---|---|
| *C12N 15/10* | (2006.01) |
| *B01L 3/00* | (2006.01) |
| *C12Q 1/6855* | (2018.01) |
| *G01N 33/58* | (2006.01) |
| *G01N 33/68* | (2006.01) |
| *C12Q 1/6806* | (2018.01) |
| *C40B 30/04* | (2006.01) |
| *C40B 40/08* | (2006.01) |
| *C40B 70/00* | (2006.01) |

(52) U.S. Cl.
CPC .... *C12N 15/1065* (2013.01); *B01L 3/502715* (2013.01); *B01L 3/502738* (2013.01); *C12Q 1/6806* (2013.01); *C12Q 1/6855* (2013.01); *G01N 33/58* (2013.01); *G01N 33/68* (2013.01); *B01L 2200/027* (2013.01); *B01L 2200/141* (2013.01); *B01L 2200/16* (2013.01); *B01L 2300/0816* (2013.01); *B01L 2300/0861* (2013.01); *B01L 2300/161* (2013.01); *B01L 2400/065* (2013.01); *C40B 30/04* (2013.01); *C40B 40/08* (2013.01); *C40B 70/00* (2013.01)

(58) Field of Classification Search
CPC ........... C12N 15/1065; B01L 3/502738; B01L 3/502715; B01L 2400/065; B01L 2300/0816; B01L 2200/141; B01L 2200/027; B01L 2300/0861; B01L 2300/161; B01L 2200/16; C12Q 1/6806; C12Q 1/6855; G01N 33/68; G01N 33/58; C40B 70/00; C40B 40/08; C40B 30/04
See application file for complete search history.

(56) References Cited

U.S. PATENT DOCUMENTS

| | | |
|---|---|---|
| 2007/0026439 A1 | 2/2007 | Faulstich et al. |
| 2009/0021728 A1 | 1/2009 | Heinz et al. |
| 2014/0329698 A1 | 11/2014 | Bignell et al. |
| 2015/0225786 A1* | 8/2015 | Litterst ............... C12Q 1/6809 506/2 |
| 2016/0114322 A1 | 4/2016 | Ismagilov et al. |
| 2016/0281134 A1 | 9/2016 | Wu |
| 2016/0288121 A1 | 10/2016 | Ismagilov et al. |
| 2017/0159136 A1* | 6/2017 | Church ................. C07H 21/04 |
| 2019/0118177 A1 | 4/2019 | Ismagilov et al. |
| 2020/0263234 A1* | 8/2020 | Seelig ................. C12Q 1/6806 |

FOREIGN PATENT DOCUMENTS

| | | |
|---|---|---|
| WO | 91/19567 A1 | 12/1991 |
| WO | 2014/152155 A1 | 9/2014 |
| WO | 2017/034970 A1 | 3/2017 |
| WO | 2019/060900 A1 | 3/2019 |
| WO | 2019/060914 A2 | 3/2019 |

OTHER PUBLICATIONS

Frei et al. (Nature Methods, v. 13, No. 3, Mar. 2016, p. 269-275, S1-S9).*
Abbyad et al., "Rails and anchors: guiding and trapping droplet microreactors in two dimensions", *The Royal Society of Chemistry,Lab on a Chip*,2011, 11; pp. 813-821.
Behbehani G.K. et al., "Transient partial permeabilization with saponin enables cellular barcoding prior to surface marker staining" *Cytometry Part A*, 2014, vol. 85, pp. 1011-1019.
Bindu, S. et al., "A Comparative Study on Permeabilization Treatments for in situDetermmation of Phytase of*Rhodotomia graciiis*", Letters in Applied Microbiology, 27, pp. 336-340, 1988.
Blackstock, D. et al., "Halo-Tag Mediated Self-Labeling of Fluorescent Proteins to Molecular Beacons for Nucleic Acid Detection", Chem. Commun., 50, pp. 13735-13733, (2014).
Chen, W. et al., "Reactive Oxygen Species (ROS) Inducible DNA Cross-Linking Agents and Their Effect on Cancer Cells and Normal Lymphocytes", J. Med. Chem, 57, pp. 4498-4510, (2013).

(Continued)

*Primary Examiner* — Robert H Havlin
(74) *Attorney, Agent, or Firm* — Steinfl + Bruno LLP

(57) ABSTRACT

Methods, systems and related compositions are provided to perform single-cell marking of a nucleic acid and/or protein in a sample based on in-cell or in-organelle barcoding of nucleic acid and/or protein complexes of the cell or organelle; the methods and systems herein described are configured to provide in-cell or in-organelle single-cell marked nucleic acid and/or protein complexes comprising a single-cell, cell-specific, or a single-cell organelle-specific marker.

17 Claims, 33 Drawing Sheets

Specification includes a Sequence Listing.

(56) References Cited

OTHER PUBLICATIONS

Collins, D.J. et al., "The Poisson Distribution and Beyond: Methods for Microfluidic Droplet Production and Single Cell Encapsulation", Lab on a Chip, 15(17), pp. 3439-3459, (2015).
Coste, F. et al., "Crystal Structure of a Double-Standard DNA Containing a Cisplatin Interstrand Cross-Link at 1.63 A Resolution: Hydration at the Platinated Site", Nucleic Acids Research, vol. 27, No. 8, pp. 1837-1846, (1999).
Dangla et al., "Trapping Microfluidic Drops in Wells of SUrface Energy" *Physical review letters*, 2011, 107, 124501.
Dekker, J. et al., "Capturing Chromosome Conformation", Science, vol. 295, pp. 1306-1311, (2001). 7 pages.
Dev, V.G. et al., "Nucleolus Organizers in MUS Musoulus Subspecies and in the RAG Mouse Cell Line", Genetics, 86, pp. 389-398, (1976).
Du, W. et al., "SlipChip", Lab Chip, 9(16), pp. 2286-2292, (2069). 14 pages.
E. Macosko et al., "Highly paralle: Genome-wide Expression profiling of Individual Cells Using Nanoliter Droplets" *Cell*, 2015, 161, 1202-1214.
Engreitz, J M. et al., "RNA-RNA Interactions Enable Specific Targeting of Noncoding RNAs to Nascent Pre-mRNAs and Chromatin Sites", Cell, 159, pp. 188-199, (2014).
Engreitz, J M. et al., "The Xist lncRNA Exploits Three-Dimensional Genome Architecture to Spread Across the X-Chromosome", Science, 341(6147), 1237973, (2013). 18 pages.
Frei a P. et al., "Highly multiplexed simultaneous detection of RNAs and proteins in single cells", *Nature Methods*,2016, vol. 13, No. 3, pp. 269-275, 19 pages.
G-Biosciences, Detergents: Handbook & Selection Guide to Detergents & Detergent Removal, (Geno Technology Inc., (2018).
Ge, S. et al., "Digital, Ultrasensitive, End-Point Protein Measurements with Large Dynamic Rance via Brownian Trapping with Drift", J. Am. Chem. Soc., 136. pp. 14662-14665, (2014).
Greenwood, C. et al., "Proximity Assays for Sensitive Quantification of Proteins", Biomolecular Detection and Quantification, 4, pp. 10-16, (2615).
Guainazzi, A. et al., "Using Synthetic DNA Interstrand Crosslinks to Elucidate Repair Pathways and Identify New Therapeutic Targets for Cancer Chemotherapy", Cell Mol. Life Sci., 67(21), pp. 3683-3697, (2010). 21 pages.
Harris, M.E et al., "RNA CrossLinking Methods", Methods Enzymol., 468, pp. 127-146, (2011). 15 pages.
Hoffman. E.A. et al., "Formaldehyde Crosslinking: A Tool for the Study of Chromatin Complexes", Journal of Biological Chemistry, vol. 296, No. 44, pp. 26404-26411, (2015). 9 pages.
Hosic, S. et al , "Microfluidic Sample Preparation for Single Cell Analysis", Analytical Chemistry, 88(1), pp. 354-380, (2016). 58 pages.
International Search Report for International Application No. PCT/US2018/052676 filed on Sep. 25, 2018 on behalf of California Institute of Technology dated Jan. 23, 2019 7 pages.
International Search Report for International Application No. PCT/US2018/052733 filed on Sep. 25, 2018 on behalf of California Institute of Technology dated Apr. 18, 2019 4 pages.
Kang, Y. et al. "Transcript amplification from single bacterium for transcriptome analysis." *Genome Res*. 21, 925-935 (2011).
Kang, Y., et al. (2815). "Single prokaryotic cell isolation and total transcript amplification protocol for transcriptomic analysis." *Nat. Protocols*10(7): 974-984.
Kenndy-Darling, J. et al., "Measuring the Formaldehyde Protein-DNA Cross-Link Reversal Rate", Analytical Chemistry, 86(12), pp. 5678-5681, (2014).
Kirchner, J. J. et al., "Interstrand Cross-Linking of Duplex DNA by Nitrous Acid. Covalent Structure of the dG-to-dG Cross-Link at the Sequence 5'-CG", Journal of the American Chemical Society, 114(11); pp. 4621-4627, (1991).
Kozov, I.A. et al., "Efficient Strategies, for the Conjugation of Oligonucleotides to Antibodies Enabling Highly Sensitive Protein Detection", Biopolymers, 73(5), pp. 621-630, (2003).

Le, T.B et al., "High-Resolution Mapping of the Spatial Organization of a Bacterial Chromosome", Science, vol. 342, pp. 731-734, (2813). 5 pages.
Lee, S H. et al., "Effective Mixing in a Microfluidic Chip Using Magnetic Particles", Lab on a Chip, 9(3), pp. 479-482, (2088).
Li, L. et al., "Dead-End Filling of SlipChip Evaluated Theoretically and Experimentally as a Function of the Surface Chemistry and the Gap Size Between the Plates for Lubricated and Dry SlipChips", Langmuir, 26(14), pp. 12465-12471, (2010), 17 pages.
Ling, G et al., "DNase I Digestion of isolated Nulcei for Genome-Wide Mapping of DNase Hypersensitivity Sites in Chromatin", Methods Molecular Biology, 977, pp. 21-33, (2014). 12 pages.
Liu, W. et al., "SlipChip for Immunoassays in Nanoliter Volumes", Anal. Chem., 82(8), pp. 3276-3282. (2018). 14 pages.
Los, G.V. et al., "HaloTag: A Novel Protein Labeling Technology for Cell Imaging and Protein Analysis", ACS Chemical Biology, vol. 3, No. 6, pp. 373-382, (2008).
Ma, L. et al., "Gene-Targeted Microfluidic Cultivation Validated by Isolation of a Gut Bacterium Listed in Human Microbiome Project's Most Wanted Taxa", PNAS, 111(27), pp. 9768-9773, (2014).
Ma, L. et al., "Individually Addressable Arrays of Replica Microbial Cultures Enabled by Splitting SlipChips", Integr. Biol. (Camb.), 6(8). pp. 796-805, (2014) . 23 pages.
Motyan, J.A. et al., "Research Applications of Proteolytic Enzymes in Molecular Biology", Biomolecules, 3, pp. 923-942, (2013).
Nagano, T. et al., "Comparison of Hi-C Results using In-Solution Versus In-Nucleus Ligation", Genome Biology, 16, p. 175, (2015). 13 pages.
Nagano, T. et al., "Single Cell Hi-C Reveals Cell-to-Call Variability in Chromosome Structure", Nature, 502(7469), pp. 59-64, (2013). 14 pages.
Nagano, T et al., "Single-Cell Hi-C for Genome-Wide Detection of Chromatin Interactions that Occur Simultaneously in a Single Cell", Nature Protocols, vol. 10, No. 12, pp. 1986-2003, (2015).
Neugebauer, J.M., "Detergents: An Overview", Methods in Enzymology, vol. 182, pp. 239-253, (1990).
New England Biolabs. "Restriction Endonucleases" Available from: https://www.neb.com/products/restriction-endonucleases. Accessed on Sep. 18, 2019.
New England Biolabs. "Types of Restriction Endonucleases"; Available from: https//www.neb.com/products/restriction-endonucleases/restriction-endonucleases/types-of-restriction . . . Accessed on Sep. 18, 2019.
Nilsson, J., et al., "Review of cell and particle trapping in microfluidic systems." *Anal Chim Acta*,2009. 649(2): p. 141-57.
Pamme, N., "Magnetism and Microfluidics", Lab Chip, 6, pp. 24-38, (2005).
Pompano et al., "Control of Initiation, Rate, and Routing of Spontaneous Capillary-Driven Flow of Liquid Droplets through Microfluidio Channels on SlipChip", *Langmuir*,2012, 28, 1931-1941.
ProteoChem, DSG Crosslinker Protocol and Product Information Sheet, Loves Park, IL., USA, (2014). 1 page.
Quinodoz, S.A. "Split-Pool Recognition of Interactions by Tag Extension [SPRITE] for DNA: Experimental Protocols" SPRITE Protocol, 2018, 34 pages.
Quinodoz, S.A. et al., "Higher-Order Inter-Chromosomal Hubs Shape 3D Genome Organization in the Nucleus", Cell, 174(3), pp. 744-757, e24, (2018).
Ramani V. et al., "Massively multiplex single-cell Hi-C" *Mature Methods*,2016, 7 pages.
Ramani, V. et al., "High-Throughout Determination of RNA Structure by Proximity Ligation", Nat. Biotechnol., 33(9), pp. 980-984, (2015). 18 pages.
Ramani. V. et al., "Mapping Three-Dimensional Genome Architecture through in situ DNase Hi-C", Nature Protocols, 11(11), pp. 2104-2121, (2016). 32 pages.
Rao. S.S. et al., "A 3D Map of the Human Genome at Kilobase Resolution Reveals Principles of Chromatin Looping", Cell 159, pp. 1665-1680, (2014).
Richards, F.M. et al., "Glutaraldehyde as a Protein Cross-Linking Reagent", Journal of Molecular Biology, 37(1), pp. 231-233, (1968).

(56) References Cited

OTHER PUBLICATIONS

Rotem, A. et al., "Single-Cel ChIP-seq Reveals Cell Subpopulations Defined by Chromatin State", Nat. Biotechnol., 33(11), pp. 1165-1172, (2015). 25 pages.

Schramm, L.L. et al., "Surfactants and Their Applications", Annu. Rep. Prog. Chem., Section C, 99, pp. 3-48, (2003).

Selck, D.A. et al. "Increased Robustness, of Single-Molecule Counting with Microfluidics, Digital Isothermal Amplification, and a Mobile Phone Versus Real-Time Kinetic Measurements", Anal. Chem., 85(22), pp. 11129-11136, (2013). 19 pages.

Shahi P. et al., "Abseq: Ultrahigh-throughput single cell protein profiling with droplet microfluidic barcoding", *Scientific Reports*, 2017, vol. 7, Article No. 4447, pp. 1-12.

Shen, F. et al., "Digital Isothermal Quantification of Nucleic Acids via Simultaneous Chemical Initiation of Recombinase Polymerase Amplification Reactions on SlipChip", Analytical Chemistry, 83(9), pp. 3533-3540, (2011). 17 pages.

Shen, F. et al., "Digital PCR on a SlipChip", Lab on a Chip, 10, pp. 2666-2672, (2010). 15 pages.

Shen, F. et al., "Multiplexed Quantification of Nucleic Acids with Large Dynamic Range Using Multivolume Digital RT-PCR on a Rotational SlipChip Tested with HIV and Hepatitis C Viral Load", Journal of the American Chemical Society, 133(44), pp. 17705-17712, (2011). 17 pages.

Shen, F. et al., "Nanoliter Multiplex PCR Arrays on a SlipChip", Analytical Chemistry, 82(11), pp. 4606-4612, (2010). 16 pages.

Shishkin A.A., et al., "Simultaneous generation of many RNA-seq libraries in a single reaction." *Nature Methods*. 2015, doi. 10.1038/nmeth.3313.

Sigma Aldrich. "Cell Dissociation with Trypsin." Available from: https://www.sigmaaldrich.com/technical-documents/articles/biology/cell-dissociation-with-trypsin.html. Accessed on Sep. 18, 2019.

Sigma Aldrich. "Removal of Adherent Cells from a Culture Surface Using Trypsin." Available from: https://www.sigmaaldrich.com/technical-documents/protocols/biology/removal-of-adherent-cells.html Accessed on Sep. 18, 2019.

Singh, V. et al., "Genetically Encoded Multispectral Labeling of Proteins with Polyfluorophores on a DNA Backbone", J. Am. Chem. Soc., 135(16), pp. 6184-6191, (2013) 19 pages.

Soderberg, O. et al., "Direct Observation of Individual Endogenous Protein Complexes in situ by Proximity Ligation", Nature Methods, vol. 3, No. 12, pp. 995-1000, (2006). 7 pages.

Stone, M P. et al., "Interstrand DNA Cross-Links Induced by Alpha, Beta-Unsaturated Aldehydes Derived From Lipid Peroxidation and Environmental Sources", ACC Chem. Res., 41(7), pp. 793-804, (2008). 28 pages.

Strauss, J.H. et al., "Denaturation of RNA with DimethylSulfoxide", *Biopolymers*, 6(6), pp. 793-807,(1968).

Sun, B. et al., "Measuring Fate and Rate of Single-Molecule Competition of Amplification and Restriction Digestion, and Its Use for Rapid Genotyping Tested with Hepatitis C Viral RNA", Agnew Chem. Int Ed. Engl., 53(31), pp. 8088-8092, (2014). 11 pages.

Sun, B. et al., "Mechanistic Evaluation of the Pros and Cons of Digital RT-LAMP for HIV-1 Viral Load Quantification on a Microfluidic Device and Improved Efficiency via a Two-Step Digital Protocol", Analytical Chemistry, 85(3), pp. 1540-1546, (2013). 14 pages.

Taanman, J.W. "The Mitochondrial Genome: Structure, Transcription, Translation, and Replication", Biochimica et Biophysica Acta, 1410(2), pp. 103-123, (1998).

Thermo Fisher Scientific Inc., Instructions: Imidoester Crosslinkers: DMA, DMP, DMS, DTBP, Rockford, IL, USA, (2012). 2 pages.

Tian, B. et al., "Two-Step Cross-Linking for Analysis of Protein-Chromatin Interactions", Methods in Molecular Biology, vol. 809, pp. 105-120, (2012). 17 pages.

Weibrecht, I. et al., "Proximity Ligation Assays: A Recent Addition to the Proteomics Toolbox", Expert Review of Proteomics, 7(3), pp. 401-409, (2814). 10 pages.

Wikipedia. "Crosslinking of DNA." 2018; Available from: https://en.wikipedia.org/wiki/Crosslinking_of_DNA. Accessed on Sep. 18, 2019.

Written Opinion for International Application No. PCT/US2018/052676 filed on Sep. 25, 2018 on behalf of California Institute of Technology dated Jan. 23, 2019 10 pages.

Written Opinion for International Application No. PCT/US2018/052733 filed on Sep. 25, 2018 on behalf of California Institute of Technology dated Apr. 18, 2019 8 pages.

Xin, Y. et al., "Use of the Fluidigm C1 Platform for RNA Sequencing of Single Mouse Pancreatic Islet Cells", PNAS, vol. 113, No. 12. pp. 3293-3298, (2016).

Yin, H. et al., "Microfluidios for Single Cell Analysis", Current Opin. Blotechnol., 23(1), pp. 110-119, (2011).

Restriction Requirement for U.S. Appl. No. 16/141,707, filed Sep. 25, 2018 on behalf of California Institute of Technology dated Nov. 27, 2019 6 pages.

Non-Final Office Action for U.S. Appl. No. 16/141,707, filed Sep. 25, 2018 on behalf of California Institute of Technology, dated Jun. 4, 2020. 17 Pages.

Clancy S. "Chemical Structure of RNA" *Nature Education*, vol. 7(1), 2008, 4 pages.

Clancy S. "RNA Functions" Nature Education, vol. 1(1), 2008, 4 pages.

Final Office Action for U.S. Appl. No. 16/141,707, filed Sep. 25, 2018 on behalf of California Institute of Technology, dated Dec. 23, 2020. 12 Pages.

Non-Final Office Action for U.S. Appl. No. 16/141,707, filed Sep. 25, 2018 on behalf of California Institute of Technology, dated Sep. 7, 2021. 16 pages.

Final Office Action for U.S. Appl. No. 16/141,707, filed Sep. 25, 2018 on behalf of California Institute of Technology dated Apr. 18, 2022 17 pages.

Non-Final Office Action for U.S. Appl. No. 16/141,707, filed Sep. 25, 2018 on behalf of California Institute of Technology dated Oct. 5, 2022 13 pages.

* cited by examiner

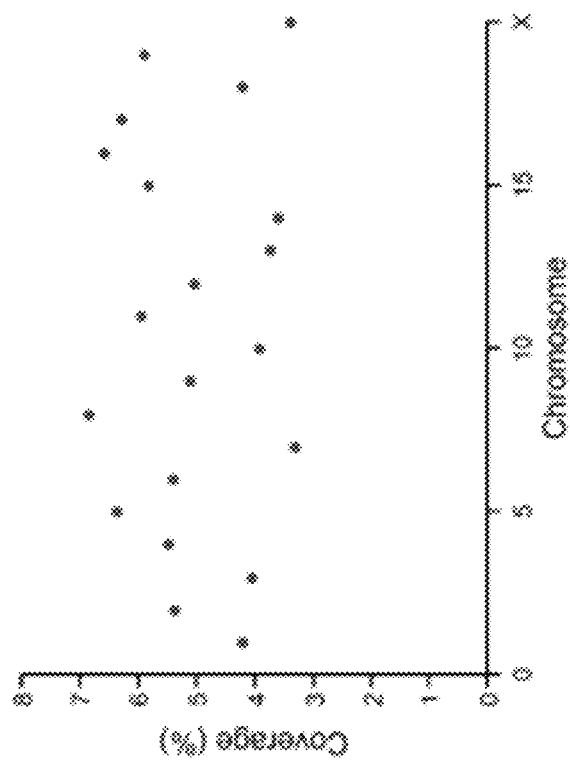
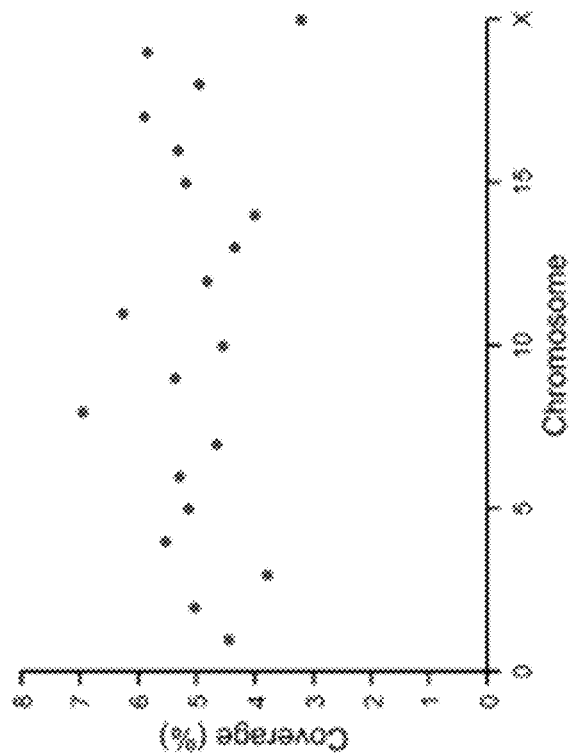
FIG. 7

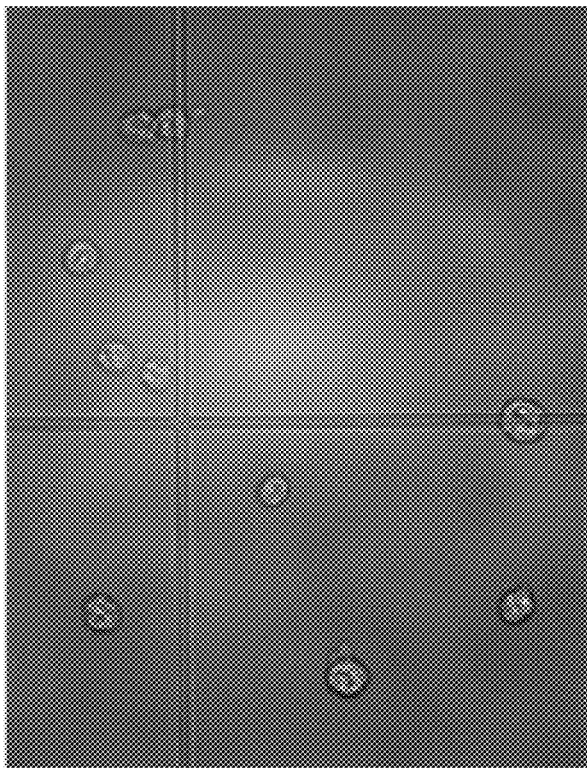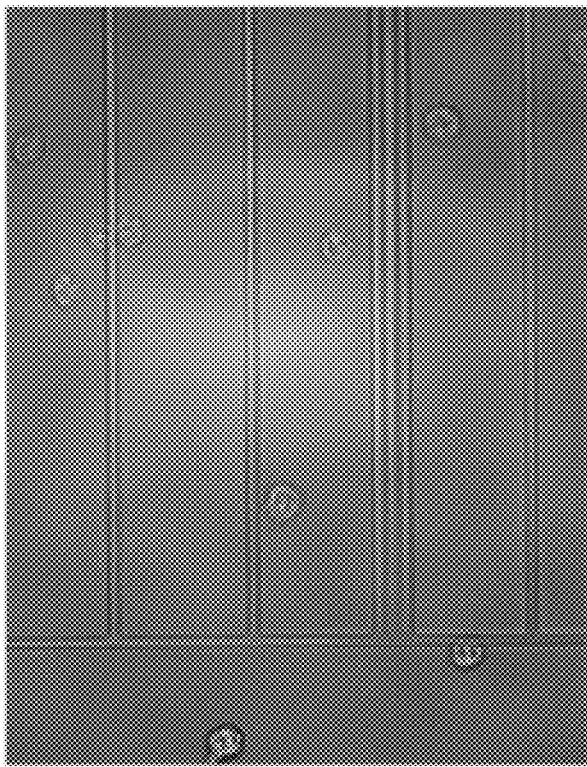
FIG. 9

DPM adaptor sequence example:

```
5'  TA××××××××AGATCGGAAGAGCGTCGTGTA      3'
    ××××××××||||||||||||
3'  T××××××××TCTAGCCTTCTGTACTGTTCAGT  5'
```

| DPM tags | SEQ ID | DPM tags | SEQ ID | DPM tags | SEQ ID |
|---|---|---|---|---|---|
| CGGTATTT | 1 | TTTTATAA | 33 | GTTGAGGA | 65 |
| GGTGGTCT | 2 | ACTCATTT | 34 | CGCAATAA | 66 |
| GCCTCTTG | 3 | CGCGCCCT | 35 | GGATTCTT | 67 |
| GTTTTTCG | 4 | TGACCTTG | 36 | AATTTACT | 68 |
| GGCAGTTC | 5 | GGAACGCG | 37 | TTTGTGTG | 69 |
| TTAAGTCC | 6 | AGTTTGTC | 38 | GCGGACCG | 70 |
| CACTCGTA | 7 | CGACATCC | 39 | GTACGGTC | 71 |
| TGGTCTCA | 8 | TCTACGTA | 40 | CCGTCACC | 72 |
| CTCCTTGT | 9 | GAAGTGCA | 41 | AAGTACTA | 73 |
| AGACTTAT | 10 | AAGCCTGT | 42 | AGATGCCA | 74 |
| GAATATGG | 11 | GTAACTAT | 43 | TTACCGGT | 75 |
| GGGTGTAG | 12 | AACTGGGG | 44 | CAGACGAT | 76 |
| TACGTTGC | 13 | TAAGAGAG | 45 | GCTAGGGG | 77 |
| TGTGCTAC | 14 | CATCGGGC | 46 | TGCTTAAG | 78 |
| TCCTGTGA | 15 | TCACCAAC | 47 | CTAGGCGC | 79 |
| TTCCGTAA | 16 | GGACGTGA | 48 | GGAGAAAC | 80 |
| GACGATTT | 17 | GAGCATAA | 49 | TAGAAGGA | 81 |
| GTGTGGCT | 18 | CTCAGGTT | 50 | TGAAGGAA | 82 |
| CTGGCTTG | 19 | TTGAACCT | 51 | TAGGCATT | 83 |
| TCCGCGCG | 20 | AATACTTG | 52 | GCACGACT | 84 |
| TCGAATTC | 21 | CTCTACCG | 53 | CCAACCTG | 85 |
| ACAGCTCC | 22 | CCGCTGTC | 54 | AAACACCG | 86 |
| GGGGCGTA | 23 | AAGAGGCC | 55 | TTCTCCTC | 87 |
| GCTCCTCA | 24 | TGGCTCTA | 56 | GTCGCACC | 88 |
| GCGATTGT | 25 | TTCATGCA | 57 | CTTCACTA | 89 |
| CCAGGTAT | 26 | CGAATGGT | 58 | TATGGCCA | 90 |
| CGTGATGG | 27 | GGCCCGAT | 59 | AGTAGCGT | 91 |
| TCTCGTAG | 28 | GCTACGCC | 60 | ACCACAAT | 92 |
| TCATTGGC | 29 | GACATCAG | 61 | TCTTACGG | 93 |
| AGCGGCAC | 30 | ATCACGGC | 62 | CTTATAAG | 94 |
| ATGGGTGA | 31 | CATTAAAC | 63 | AATGACGC | 95 |
| ATGCAAAC | 32 | ACCCTCGA | 64 | CCTGCAAA | 96 |

FIG. 25

Odd adaptor sequence example:

5'   CAAGTCAA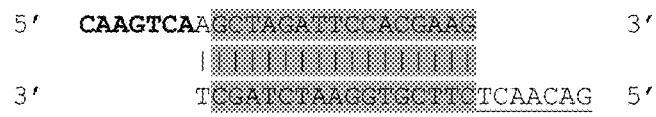                    3'

3'           T          TCAACAG   5'

| Odd Adaptor tags | SEQ ID | Odd Adaptor tags | SEQ ID |
|---|---|---|---|
| TTCGTGGAATCTAGC | 97 | CACACGTCGAGCGAT | 145 |
| CCTCTAACTAAGGAT | 98 | ACGCCGATAAGGACT | 146 |
| CCTACAGAAGTATCT | 99 | GCTCTTCATAAGCCT | 147 |
| GTGTCAAGCACCGCT | 100 | TCCTGGACAGTGAGC | 148 |
| GTATTACTCATAGGC | 101 | GTCACCAAGAGACGC | 149 |
| ACCGCAATATAATTG | 102 | TTCTTGTCTTGGAGC | 150 |
| GACAAGCCACCTTAT | 103 | TGTGTAGGAGCAAGT | 151 |
| CTGTGTCTGTCACCT | 104 | GTTCATTACGTCAGT | 152 |
| CCTGTGCGTTAGAGT | 105 | CTCAATCTGGATCGC | 153 |
| ATCAATCGCAGCGGT | 106 | CTGGAAGCCTCTAGC | 154 |
| TCGGCAACAGACCAT | 107 | GAATATAGGCACTTG | 155 |
| CTAGGTCGAATGCCT | 108 | GTTCTCCTTAGAGAT | 156 |
| CGGTCACGCCTGAGC | 109 | CCTTCCGCCTCGTAT | 157 |
| ATCAATGAACGAGGC | 110 | TCAAGGTGTCCGAGT | 158 |
| GCCGTGCCTCTAACT | 111 | TTGCTTAACGGATTG | 159 |
| TGGCTAGGTTGTGTG | 112 | TATGAATATGTGGCT | 160 |
| ACTAGAGGTGTCCGT | 113 | TTCCAACACACGGAT | 161 |
| GCCATGCAGTTACGC | 114 | CGTGAGGATCAACGC | 162 |
| GTGCTATAATCTTGT | 115 | TATCTGTGAGCCGAT | 163 |
| AGTTCGTCACCGTGT | 116 | CGTTCCATGCTATCT | 164 |
| TCGAGTGGAGCAATT | 117 | AGACAGACGGTCTAT | 165 |
| GCGTCATCGGACTCT | 118 | TCTCTTGCATCACGC | 166 |

FIG. 26

Odd adaptor sequence example:

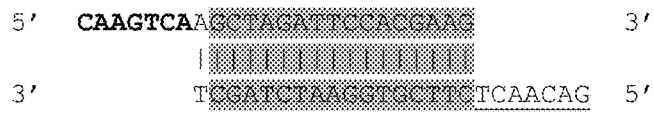

```
5'  CAAGTCAAGCTAGATTCACGAA              3'
                ||||||||||||||||
3'           TCGATCTAAGTGCTTTCAACAG     5'
```

| Odd Adaptor tags | SEQ ID | Odd Adaptor tags | SEQ ID |
|---|---|---|---|
| GGTTGCTTGCATTGT | 119 | TATCGCACTCATTGT | 167 |
| CGGTTCGTTAGGCGT | 120 | TCACTCGGTGCGACT | 168 |
| TACTCGGTTAGTCCT | 121 | CTACATCTGTCGAGT | 169 |
| TGCCTACGACGTAGC | 122 | GATACCGTAGCAGAT | 170 |
| GTAGAACGCTAGGTT | 123 | AATTGAATACACCGT | 171 |
| GTCACACGTTGAACT | 124 | GATAGCACCGTTCAT | 172 |
| CCGCCTAGTGAGGCT | 125 | GCCATTCCACTTAGC | 173 |
| AGGACGCAGTGAGAT | 126 | TGAGTGCCGCAGACT | 174 |
| AGCAACGTCCTATTG | 127 | CTCCAGTGTCGTCGC | 175 |
| ATACGGCACCTACTT | 128 | CCTAGTAGAAGACGT | 176 |
| TCGTTCTCATTCTGT | 129 | GAGTGCGTGTTAGCT | 177 |
| ACAATCACCGTGTAT | 130 | TCTAACACACAGCCT | 178 |
| ATCATACCACGCCGC | 131 | ATATCTCGAATAGGC | 179 |
| ATACTCTGGTGCCAT | 132 | ACCAAGCACCAGACT | 180 |
| TGATGTGATAAGGCT | 133 | ACGAACTCCATGCGT | 181 |
| TTGAACACTTCCGTT | 134 | CTATTGCATCTTCAT | 182 |
| GGTTGCAGCCTCCGC | 135 | TCCGATGGACGCCGT | 183 |
| TGCTAACCTACACAT | 136 | CTCTTGGAGGTATCT | 184 |
| AACGAGGTCAGTCGC | 137 | GAAGTGGTTCGGTCT | 185 |
| AGTGGCACTTCACCT | 138 | GAGAGGATGAATGCT | 186 |
| GGCAACGGCTCATGT | 139 | TAACGCTGTGAAGGC | 187 |
| CCTTCCTATGCTACT | 140 | AGACTCAATTAGGCT | 188 |
| GGCAAGACTGCCTAT | 141 | TCCGAGATGATGTGT | 189 |
| TCGAGGATAGCCTGT | 142 | CGTGTCATCGCTAGT | 190 |
| AACGCAGGATACTAT | 143 | GCTGACATAAGACCT | 191 |
| CTCAGGAAGGCTGAT | 144 | GAAGCCTCGGATTGT | 192 |

FIG. 26 (Continued)

Even adaptor sequence example:

```
5'   AGTTGTCA                        3'
         |
3'              GTTCAGT  5'
```
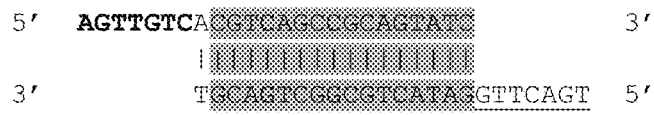

| Even Adaptor tags | SEQ ID | Even Adaptor tags | SEQ ID |
|---|---|---|---|
| ATACTGCGGCTGACG | 193 | CGCTTGGCTAATAGG | 241 |
| CTAGGTGGCGGTCTG | 194 | GAAGATCGCAATTAG | 242 |
| GTGACATTAAGGTTG | 195 | TCTACACCGCTGAAG | 243 |
| TATCAATGATGGTGC | 196 | CGCTCCTAGATGTTC | 244 |
| CCTCACGTCTAGGCG | 197 | TCCGTGGCTTACTGG | 245 |
| ATTCCTCTGCGATGC | 198 | GACTACTGCTCACCG | 246 |
| GATTACGTTCCACGG | 199 | GTGAAGTGACTGAGG | 247 |
| GTAGCTTACGTCATC | 200 | TAGATTGTTGCGTGC | 248 |
| GTAGGTTCTGGAATC | 201 | CCGACATCCGCTGTG | 249 |
| AATCACGAGTTCGTC | 202 | TCAAGCCTTGCGGAG | 250 |
| CAAGCTAGACGGTTC | 203 | CCTGCTTCCGTGATG | 251 |
| TAACCATATTGCCGT | 204 | TTATTGCCACCAGTG | 252 |
| AGTCCTGCCACTACG | 205 | CACGTTCAACTGGCG | 253 |
| GAGGATTGGAGAATC | 206 | CCAGTTAGCAAGACG | 254 |
| CCAACAAGATAGTGC | 207 | GCTGGAACTCATAAG | 255 |
| AATGCGTGTGTTCGG | 208 | TGCTCGTTGGTCCAG | 256 |
| TGCCGTGACTCCATC | 209 | AGTCTTCGGATACCG | 257 |
| CCTTCGTTAAGGCT | 210 | TGGACCTCTAATTGC | 258 |
| AGAAGTGCTCCAGGT | 211 | CATCGACTCACCTTC | 259 |
| CGGAGGATCTAGTGG | 212 | GCGGATTCTCAGTGG | 260 |
| GCTGAGCTGGTCTAG | 213 | GAACACGCACATGGC | 261 |
| GCTTCATTAACTAGG | 214 | GTTGCTGTGTGGATC | 262 |
| GATTAGTGCGAGAGG | 215 | CCAGCAATCCTACAG | 263 |

FIG. 27

Even adaptor sequence example:

```
5'  AGTTGTCA
                                          3'

3'             
                     GTTCAGT  5'
```
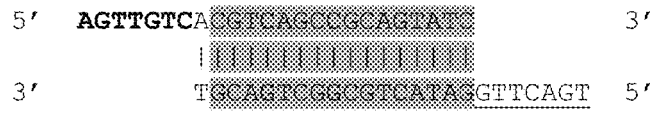

| Even Adaptor tags | SEQ ID | Even Adaptor tags | SEQ ID |
|---|---|---|---|
| ACGCTCTATACACCG | 216 | ACCGCAGAGAGGTAG | 264 |
| GTAGTCCAGGTCGTC | 217 | ACGCTTATGGCAGTG | 265 |
| GACGACTGACTAGGT | 218 | GTTGCGTAGTGATGC | 266 |
| GCATAGGACAGGCAG | 219 | TGATTCCTGAGTCCG | 267 |
| TCGCACCACAACCAT | 220 | GCACGAGATCCTTGC | 268 |
| ACTCAAGCACCTCTC | 221 | CTAGCACCTCGTAAT | 269 |
| GGTCGCATGATAAGG | 222 | TCAATGGACGGATGC | 270 |
| GTATCGTATAGGTCG | 223 | CGTATACCGAGTTGG | 271 |
| TCCGTTGCTATAATC | 224 | GCCTATTGTACTGCG | 272 |
| GGTTGATTCAAGAAT | 225 | CACACCATCGTATTC | 273 |
| GCATGGATACCAGCG | 226 | TATCCTGTCAACGGC | 274 |
| GTCCAGGCATTCGTC | 227 | ATGCTTCACACGGTG | 275 |
| TCGTGTGAGTCTCGT | 228 | GCTTGCCGTAGCGTG | 276 |
| ACAACGGTGCGACTG | 229 | TGTCCGCCTGCATGG | 277 |
| ATTCTCTGCCGAGAG | 230 | GTCGATATTGATCCG | 278 |
| CGTATCGAGGTGCCG | 231 | GGAACACTCTACTGC | 279 |
| GTTGTTCGTGTGTCG | 232 | AAGCGGAAGGTATAG | 280 |
| GTCCTGTCTAGTCCG | 233 | CTACTTCCGAATCAG | 281 |
| GATGACCTGTCCATG | 234 | CCACGGAGCCTTCTC | 282 |
| AGCGTGCAGTGGAAG | 235 | GCACACGATCATCTG | 283 |
| GGCTCTGAACCTATC | 236 | CTGTTACGTCCGCTG | 284 |
| GAGCTGGACAGGTGG | 237 | CTGGTGTCACGTCTC | 285 |
| CACAGTCCTCCATGC | 238 | ACGCTGTGGCGATTC | 286 |
| CCGCACTCTGATAAT | 239 | ACTGTTCGACACGTC | 287 |
| TTGATAAGCCGACGG | 240 | GCTCCAGTCGTAATC | 288 |

FIG. 27 (Continued)

Y-end adaptor sequence example:

Y-Shape (Lig to Even, Position A1)
```
5'  CAAGTCAA░░░░░░░░AGATCGGAAGA                              3'
            ░░░░░░░░|||||||||||
3'          ░░░░░░░░TCTAGCCTTCTCGTGTGCAGACTTGAGGTC  5'
```

| Y-end Adaptor tags | SEQ ID | Y-end Adaptor tags | SEQ ID | Y-end Adaptor tags | SEQ ID |
|---|---|---|---|---|---|
| TATTATGGT | 289 | CTGCATTAT | 321 | TTCCAAGGC | 353 |
| TAGCTACCT | 290 | TTGTAGCTG | 322 | GTAGCATCC | 354 |
| ATTGTTCAT | 291 | GCCGTTATC | 323 | CCTACGGCC | 355 |
| CCACCGAAT | 292 | GAATACAAC | 324 | TACGCTTGA | 356 |
| CATCAGTTG | 293 | AGGAGAATA | 325 | CTTGGCGAC | 357 |
| CCTTGAGAG | 294 | CATCTAAGA | 326 | CTTAAACCG | 358 |
| ATCAGGAAG | 295 | TCAATACAA | 327 | CTCTGTTGT | 359 |
| CGAAGTAGC | 296 | CGATAAGTT | 328 | CTCTGTTGT | 360 |
| TTAACCGAC | 297 | TTGACAAGT | 329 | CGTTTCACA | 361 |
| GTTCATACA | 298 | TGTAGTTCT | 330 | CGCTTCTAA | 362 |
| GACGAAGAA | 299 | GCCTATCCT | 331 | CCGACTGCT | 363 |
| TGCCTCTGT | 300 | GGCGGCAAT | 332 | CATCCAGTC | 364 |
| GAGATGGAT | 301 | TTACGGCCA | 333 | CAGCTCCGA | 365 |
| ACCATAGTG | 302 | GGAATCCTC | 334 | CAACAACGT | 366 |
| GTACGAATG | 303 | CTCATGTTA | 335 | CATTAGACT | 367 |
| AAGGAGACG | 304 | GATTGATTA | 336 | CCAGCACTT | 368 |
| CCATTAACC | 305 | ATATACTGA | 337 | GTGATGTAC | 369 |
| TCTCCTTAC | 306 | CGCTCCTTC | 338 | GTAGTCGTC | 370 |
| ATCTCACCA | 307 | AGTACGCGA | 339 | GGTCCAACT | 371 |
| CGTAACTAA | 308 | CACGGATCT | 340 | GGCGCCATA | 372 |
| AGACTGGCT | 309 | TCCTGGTAT | 341 | GGAGAGCAC | 373 |
| AATACCACT | 310 | AGGTCTTCG | 342 | GCTCTGCAA | 374 |
| GCGAACGTT | 311 | TGGATGCTC | 343 | ATTACACGC | 375 |
| GCATCGAGT | 312 | TGAGTAATT | 344 | AGTTGAAAT | 376 |
| GATGACGTA | 313 | TCTCATATT | 345 | AGGCCCTTT | 377 |
| GAGCAGAAC | 314 | TCGAACATA | 346 | AGATGAGCG | 378 |
| GACACCCCG | 315 | TCATACTAC | 347 | ACTCTTCTT | 379 |
| GTTGTTCGA | 316 | TATCGACGT | 348 | ACCATTATT | 380 |
| TTTATATGT | 317 | TAGACCAGG | 349 | ACAGACTCA | 381 |
| TTGACATCA | 318 | TAATGTGGA | 350 | AATTGTCTG | 382 |
| TTATCCCCC | 319 | ATTAGTATG | 351 | AAGGCCTCA | 383 |
| TGTGACCAG | 320 | ATCCTATCC | 352 | AACGAACAG | 384 |

FIG. 28

SEQUENCE LISTING

<160> NUMBER OF SEQ ID NOS: 384

<210> SEQ ID NO 1
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 1 cggtattt                                                                8

<210> SEQ ID NO 2
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 2 ggtggtct                                                                8

<210> SEQ ID NO 3
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 3 gcctcttg                                                                8

<210> SEQ ID NO 4
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 4 gttttcg                                                                 8

<210> SEQ ID NO 5
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 5 ggcagttc                                                                8

<210> SEQ ID NO 6
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 6 ttaagtcc                                                                8

<210> SEQ ID NO 7
<211> LENGTH: 8
<212> TYPE: DNA
<213> ORGANISM: Artificial Sequence

```
<220> FEATURE:
<223> OTHER INFORMATION: Synthetic polynucleotide

<400> SEQUENCE: 7 cactcgta                                                                        8

<210> SEQ ID NO 8
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 8 tggtctca                                                                        8

<210> SEQ ID NO 9
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 9 ctccttgt                                                                        8

<210> SEQ ID NO 10
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 10 agacttat                                                                        8

<210> SEQ ID NO 11
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 11 gaatatgg                                                                        8

<210> SEQ ID NO 12
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 12 gggtgtag                                                                        8

<210> SEQ ID NO 13
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 13 tacgttgc                                                                        8
```

```
<210> SEQ ID NO 14
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 14 tgtgctac                                                                 8

<210> SEQ ID NO 15
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 15 tcctgtga                                                                 8

<210> SEQ ID NO 16
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 16 ttccgtaa                                                                 8

<210> SEQ ID NO 17
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 17 gacgattt                                                                 8

<210> SEQ ID NO 18
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 18 gtgtggct                                                                 8

<210> SEQ ID NO 19
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 19 ctggcttg                                                                 8

<210> SEQ ID NO 20
<211> LENGTH: 8
<212> TYPE: DNA
<213> ORGANISM: Artificial Sequence
<220> FEATURE:
<223> OTHER INFORMATION: Synthetic polynucleotide
```

```
<400> SEQUENCE: 20 tccgcgcg                                                          8

<210> SEQ ID NO 21
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 21 tcgaattc                                                          8

<210> SEQ ID NO 22
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 22 acagctcc                                                          8

<210> SEQ ID NO 23
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 23 ggggcgta                                                          8

<210> SEQ ID NO 24
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 24 gctcctca                                                          8

<210> SEQ ID NO 25
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 25 gcgattgt                                                          8

<210> SEQ ID NO 26
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 26 ccaggtat                                                          8

<210> SEQ ID NO 27
```

```
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 27 cgtgatgg                                                                 8

<210> SEQ ID NO 28
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 28 tctcgtag                                                                 8

<210> SEQ ID NO 29
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 29 tcattggc                                                                 8

<210> SEQ ID NO 30
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 30 agcggcac                                                                 8

<210> SEQ ID NO 31
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 31 atgggtga                                                                 8

<210> SEQ ID NO 32
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 32 atgcaaac                                                                 8

<210> SEQ ID NO 33
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 33
``` tttttataa                                                         8

<210> SEQ ID NO 34
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 34 actcattt                                                          8

<210> SEQ ID NO 35
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 35 cgcgccct                                                          8

<210> SEQ ID NO 36
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 36 tgaccttg                                                          8

<210> SEQ ID NO 37
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 37 ggaacgcg                                                          8

<210> SEQ ID NO 38
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 38 agtttgtc                                                          8

<210> SEQ ID NO 39
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 39 cgacatcc                                                          8

<210> SEQ ID NO 40
<211> LENGTH: 8
<212> TYPE: DNA

```
<213> ORGANISM: Artificial Sequence
<220> FEATURE:
<223> OTHER INFORMATION: Synthetic polynucleotide

<400> SEQUENCE: 40 tctacgta                                                               8

<210> SEQ ID NO 41
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 41 gaagtgca                                                               8

<210> SEQ ID NO 42
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 42 aagcctgt                                                               8

<210> SEQ ID NO 43
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 43 gtaactat                                                               8

<210> SEQ ID NO 44
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 44 aactgggg                                                               8

<210> SEQ ID NO 45
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 45 taagagag                                                               8

<210> SEQ ID NO 46
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 46 catcgggc                                                               8
```

```
<210> SEQ ID NO 47
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 47 tcaccaac                                                                   8

<210> SEQ ID NO 48
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 48 ggacgtga                                                                   8

<210> SEQ ID NO 49
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 49 gagcataa                                                                   8

<210> SEQ ID NO 50
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 50 ctcaggtt                                                                   8

<210> SEQ ID NO 51
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 51 ttgaacct                                                                   8

<210> SEQ ID NO 52
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 52 aatacttg                                                                   8

<210> SEQ ID NO 53
<211> LENGTH: 8
<212> TYPE: DNA
<213> ORGANISM: Artificial Sequence
<220> FEATURE:
```

<223> OTHER INFORMATION: Synthetic polynucleotide

<400> SEQUENCE: 53 ctctaccg                                                                 8

<210> SEQ ID NO 54
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 54 ccgctgtc                                                                 8

<210> SEQ ID NO 55
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 55 aagaggcc                                                                 8

<210> SEQ ID NO 56
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 56 tggctcta                                                                 8

<210> SEQ ID NO 57
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 57 ttcatgca                                                                 8

<210> SEQ ID NO 58
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 58 cgaatggt                                                                 8

<210> SEQ ID NO 59
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 59 ggcccgat                                                                 8

```
<210> SEQ ID NO 60
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 60 gctacgcc                                                                 8

<210> SEQ ID NO 61
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 61 gacatcag                                                                 8

<210> SEQ ID NO 62
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 62 atcacggc                                                                 8

<210> SEQ ID NO 63
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 63 cattaaac                                                                 8

<210> SEQ ID NO 64
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 64 accctcga                                                                 8

<210> SEQ ID NO 65
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 65 gttgagga                                                                 8

<210> SEQ ID NO 66
<211> LENGTH: 8
<212> TYPE: DNA
<213> ORGANISM: Artificial Sequence
<220> FEATURE:
<223> OTHER INFORMATION: Synthetic polynucleotide
```

```
<400> SEQUENCE: 66 cgcaataa                                                                    8

<210> SEQ ID NO 67
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 67 ggattctt                                                                    8

<210> SEQ ID NO 68
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 68 aatttact                                                                    8

<210> SEQ ID NO 69
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 69 tttgtgtg                                                                    8

<210> SEQ ID NO 70
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 70 gcggaccg                                                                    8

<210> SEQ ID NO 71
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 71 gtacggtc                                                                    8

<210> SEQ ID NO 72
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 72 ccgtcacc                                                                    8

<210> SEQ ID NO 73
<211> LENGTH: 8
```

```
<212> TYPE: DNA
<213> ORGANISM: Artificial Sequence
<220> FEATURE:
<223> OTHER INFORMATION: Synthetic polynucleotide

<400> SEQUENCE: 73 aagtacta                                                                  8

<210> SEQ ID NO 74
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 74 agatgcca                                                                  8

<210> SEQ ID NO 75
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 75 ttaccggt                                                                  8

<210> SEQ ID NO 76
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 76 cagacgat                                                                  8

<210> SEQ ID NO 77
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 77 gctagggg                                                                  8

<210> SEQ ID NO 78
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 78 tgcttaag                                                                  8

<210> SEQ ID NO 79
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 79
``` ctaggcgc                                                                    8

<210> SEQ ID NO 80
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 80 ggagaaac                                                                    8

<210> SEQ ID NO 81
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 81 tagaagga                                                                    8

<210> SEQ ID NO 82
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 82 tgaaggaa                                                                    8

<210> SEQ ID NO 83
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 83 taggcatt                                                                    8

<210> SEQ ID NO 84
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 84 gcacgact                                                                    8

<210> SEQ ID NO 85
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 85 ccaacctg                                                                    8

<210> SEQ ID NO 86
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 86 aaacaccg                                                                    8

<210> SEQ ID NO 87
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 87 ttctcctc                                                                    8

<210> SEQ ID NO 88
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 88 gtcgcacc                                                                    8

<210> SEQ ID NO 89
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 89 cttcacta                                                                    8

<210> SEQ ID NO 90
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 90 tatggcca                                                                    8

<210> SEQ ID NO 91
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 91 agtagcgt                                                                    8

<210> SEQ ID NO 92
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 92 accacaat                                                                    8

<210> SEQ ID NO 93
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 93 tcttacgg                                                                 8

<210> SEQ ID NO 94
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 94 cttataag                                                                 8

<210> SEQ ID NO 95
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 95 aatgacgc                                                                 8

<210> SEQ ID NO 96
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 96 cctgcaaa                                                                 8

<210> SEQ ID NO 97
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 97
ttcgtggaat ctagc                                                        15

<210> SEQ ID NO 98
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 98
cctctaacta aggat                                                        15

<210> SEQ ID NO 99
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 99
cctacagaag tatct                                                        15

<210> SEQ ID NO 100
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 100
gtgtcaagca ccgct                                                        15

<210> SEQ ID NO 101
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 101
gtattactca taggc                                                        15

<210> SEQ ID NO 102
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 102
accgcaatat aattg                                                        15

<210> SEQ ID NO 103
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 103
gacaagccac cttat                                                        15

<210> SEQ ID NO 104
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 104
ctgtgtctgt cacct                                                        15

<210> SEQ ID NO 105
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 105
cctgtgcgtt agagt                                                        15

<210> SEQ ID NO 106

```
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 106
atcaatcgca gcggt                                                          15

<210> SEQ ID NO 107
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 107
tcggcaacag accat                                                          15

<210> SEQ ID NO 108
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 108
ctaggtcgaa tgcct                                                          15

<210> SEQ ID NO 109
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 109
cggtcacgcc tgagc                                                          15

<210> SEQ ID NO 110
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 110
atcaatgaac gaggc                                                          15

<210> SEQ ID NO 111
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 111
gccgtgcctc taact                                                          15

<210> SEQ ID NO 112
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 112
```
tggctaggtt gtgtg                                                      15

<210> SEQ ID NO 113
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 113
actagaggtg tccgt                                                      15

<210> SEQ ID NO 114
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 114
gccatgcagt tacgc                                                      15

<210> SEQ ID NO 115
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 115
gtgctataat cttgt                                                      15

<210> SEQ ID NO 116
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 116
agttcgtcac cgtgt                                                      15

<210> SEQ ID NO 117
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 117
tcgagtggag caatt                                                      15

<210> SEQ ID NO 118
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 118
gcgtcatcgg actct                                                      15

<210> SEQ ID NO 119
<211> LENGTH: 15
<212> TYPE: DNA

<213> ORGANISM: Artificial Sequence
<220> FEATURE:
<223> OTHER INFORMATION: Synthetic polynucleotide

<400> SEQUENCE: 119
ggttgcttgc attgt                                                        15

<210> SEQ ID NO 120
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 120
cggttcgtta ggcgt                                                        15

<210> SEQ ID NO 121
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 121
tactcggtta gtcct                                                        15

<210> SEQ ID NO 122
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 122
tgcctacgac gtagc                                                        15

<210> SEQ ID NO 123
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 123
gtagaacgct aggtt                                                        15

<210> SEQ ID NO 124
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 124
gtcacacgtt gaact                                                        15

<210> SEQ ID NO 125
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 125
ccgcctagtg aggct                                                        15

<210> SEQ ID NO 126
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 126
aggacgcagt gagat                                                    15

<210> SEQ ID NO 127
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 127
agcaacgtcc tattg                                                    15

<210> SEQ ID NO 128
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 128
atacggcacc tactt                                                    15

<210> SEQ ID NO 129
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 129
tcgttctcat tctgt                                                    15

<210> SEQ ID NO 130
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 130
acaatcaccg tgtat                                                    15

<210> SEQ ID NO 131
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 131
atcataccac gccgc                                                    15

<210> SEQ ID NO 132
<211> LENGTH: 15
<212> TYPE: DNA
<213> ORGANISM: Artificial Sequence
<220> FEATURE:

<223> OTHER INFORMATION: Synthetic polynucleotide

<400> SEQUENCE: 132
atactctggt gccat                                                        15

<210> SEQ ID NO 133
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 133
tgatgtgata aggct                                                        15

<210> SEQ ID NO 134
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 134
ttgaacactt ccgtt                                                        15

<210> SEQ ID NO 135
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 135
ggttgcagcc tccgc                                                        15

<210> SEQ ID NO 136
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 136
tgctaaccta cacat                                                        15

<210> SEQ ID NO 137
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 137
aacgaggtca gtcgc                                                        15

<210> SEQ ID NO 138
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 138
agtggcactt cacct                                                        15

```
<210> SEQ ID NO 139
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 139
ggcaacggct catgt                                                15

<210> SEQ ID NO 140
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 140
ccttcctatg ctact                                                15

<210> SEQ ID NO 141
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 141
ggcaagactg cctat                                                15

<210> SEQ ID NO 142
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 142
tcgaggatag cctgt                                                15

<210> SEQ ID NO 143
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 143
aacgcaggat actat                                                15

<210> SEQ ID NO 144
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 144
ctcaggaagg ctgat                                                15

<210> SEQ ID NO 145
<211> LENGTH: 15
<212> TYPE: DNA
<213> ORGANISM: Artificial Sequence
<220> FEATURE:
<223> OTHER INFORMATION: Synthetic polynucleotide
```

```
<400> SEQUENCE: 145
cacacgtcga gcgat                                                         15

<210> SEQ ID NO 146
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 146
acgccgataa ggact                                                         15

<210> SEQ ID NO 147
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 147
gctcttcata agcct                                                         15

<210> SEQ ID NO 148
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 148
tcctggacag tgagc                                                         15

<210> SEQ ID NO 149
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 149
gtcaccaaga gacgc                                                         15

<210> SEQ ID NO 150
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 150
ttcttgtctt ggagc                                                         15

<210> SEQ ID NO 151
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 151
tgtgtaggag caagt                                                         15

<210> SEQ ID NO 152
<211> LENGTH: 15
```

```
<212> TYPE: DNA
<213> ORGANISM: Artificial Sequence
<220> FEATURE:
<223> OTHER INFORMATION: Synthetic polynucleotide

<400> SEQUENCE: 152
gttcattacg tcagt                                                       15

<210> SEQ ID NO 153
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 153
ctcaatctgg atcgc                                                       15

<210> SEQ ID NO 154
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 154
ctggaagcct ctagc                                                       15

<210> SEQ ID NO 155
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 155
gaatataggc acttg                                                       15

<210> SEQ ID NO 156
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 156
gttctcctta gagat                                                       15

<210> SEQ ID NO 157
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 157
ccttccgcct cgtat                                                       15

<210> SEQ ID NO 158
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 158
```

-continued tcaaggtgtc cgagt                                                    15

<210> SEQ ID NO 159
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 159
ttgcttaacg gattg                                                    15

<210> SEQ ID NO 160
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 160
tatgaatatg tggct                                                    15

<210> SEQ ID NO 161
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 161
ttccaacaca cggat                                                    15

<210> SEQ ID NO 162
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 162
cgtgaggatc aacgc                                                    15

<210> SEQ ID NO 163
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 163
tatctgtgag ccgat                                                    15

<210> SEQ ID NO 164
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 164
cgttccatgc tatct                                                    15

<210> SEQ ID NO 165
<211> LENGTH: 15
<212> TYPE: DNA
<213> ORGANISM: Artificial Sequence

```
<220> FEATURE:
<223> OTHER INFORMATION: Synthetic polynucleotide

<400> SEQUENCE: 165
agacagacgg tctat                                                    15

<210> SEQ ID NO 166
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 166
tctcttgcat cacgc                                                    15

<210> SEQ ID NO 167
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 167
tatcgcactc attgt                                                    15

<210> SEQ ID NO 168
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 168
tcactcggtg cgact                                                    15

<210> SEQ ID NO 169
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 169
ctacatctgt cgagt                                                    15

<210> SEQ ID NO 170
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 170
gataccgtag cagat                                                    15

<210> SEQ ID NO 171
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 171
aattgaatac accgt                                                    15
```

```
<210> SEQ ID NO 172
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 172
gatagcaccg ttcat                                                    15

<210> SEQ ID NO 173
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 173
gccattccac ttagc                                                    15

<210> SEQ ID NO 174
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 174
tgagtgccgc agact                                                    15

<210> SEQ ID NO 175
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 175
ctccagtgtc gtcgc                                                    15

<210> SEQ ID NO 176
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 176
cctagtagaa gacgt                                                    15

<210> SEQ ID NO 177
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 177
gagtgcgtgt tagct                                                    15

<210> SEQ ID NO 178
<211> LENGTH: 15
<212> TYPE: DNA
<213> ORGANISM: Artificial Sequence
<220> FEATURE:
<223> OTHER INFORMATION: Synthetic polynucleotide
```

<400> SEQUENCE: 178
tctaacacac agcct                                                    15

<210> SEQ ID NO 179
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 179
atatctcgaa taggc                                                    15

<210> SEQ ID NO 180
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 180
accaagcacc agact                                                    15

<210> SEQ ID NO 181
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 181
acgaactcca tgcgt                                                    15

<210> SEQ ID NO 182
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 182
ctattgcatc ttcat                                                    15

<210> SEQ ID NO 183
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 183
tccgatggac gccgt                                                    15

<210> SEQ ID NO 184
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 184
ctcttggagg tatct                                                    15

<210> SEQ ID NO 185

```
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 185
gaagtggttc ggtct                                                     15

<210> SEQ ID NO 186
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 186
gagaggatga atgct                                                     15

<210> SEQ ID NO 187
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 187
taacgctgtg aaggc                                                     15

<210> SEQ ID NO 188
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 188
agactcaatt aggct                                                     15

<210> SEQ ID NO 189
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 189
tccgagatga tgtgt                                                     15

<210> SEQ ID NO 190
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 190
cgtgtcatcg ctagt                                                     15

<210> SEQ ID NO 191
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 191
```
gctgacataa gacct                                             15

<210> SEQ ID NO 192
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 192
gaagcctcgg attgt                                             15

<210> SEQ ID NO 193
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 193
atactgcggc tgacg                                             15

<210> SEQ ID NO 194
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 194
ctaggtggcg gtctg                                             15

<210> SEQ ID NO 195
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 195
gtgacattaa ggttg                                             15

<210> SEQ ID NO 196
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 196
tatcaatgat ggtgc                                             15

<210> SEQ ID NO 197
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 197
cctcacgtct aggcg                                             15

<210> SEQ ID NO 198
<211> LENGTH: 15
<212> TYPE: DNA

<213> ORGANISM: Artificial Sequence
<220> FEATURE:
<223> OTHER INFORMATION: Synthetic polynucleotide

<400> SEQUENCE: 198
attcctctgc gatgc                                                          15

<210> SEQ ID NO 199
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 199
gattacgttc cacgg                                                          15

<210> SEQ ID NO 200
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 200
gtagcttacg tcatc                                                          15

<210> SEQ ID NO 201
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 201
gtaggttctg gaatc                                                          15

<210> SEQ ID NO 202
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 202
aatcacgagt tcgtc                                                          15

<210> SEQ ID NO 203
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 203
caagctagac ggttc                                                          15

<210> SEQ ID NO 204
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 204
taaccatatt gccgt                                                          15

<210> SEQ ID NO 205
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 205
agtcctgcca ctacg                                                      15

<210> SEQ ID NO 206
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 206
gaggattgga gaatc                                                      15

<210> SEQ ID NO 207
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 207
ccaacaagat agtgc                                                      15

<210> SEQ ID NO 208
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 208
aatgcgtgtg ttcgg                                                      15

<210> SEQ ID NO 209
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 209
tgccgtgact ccatc                                                      15

<210> SEQ ID NO 210
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 210
ccttcgttaa ggctg                                                      15

<210> SEQ ID NO 211
<211> LENGTH: 15
<212> TYPE: DNA
<213> ORGANISM: Artificial Sequence
<220> FEATURE:

<223> OTHER INFORMATION: Synthetic polynucleotide

<400> SEQUENCE: 211
agaagtgctc caggt                                                    15

<210> SEQ ID NO 212
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 212
cggaggatct agtgg                                                    15

<210> SEQ ID NO 213
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 213
gctgagctgg tctag                                                    15

<210> SEQ ID NO 214
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 214
gcttcattaa ctagg                                                    15

<210> SEQ ID NO 215
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 215
gattagtgcg agagg                                                    15

<210> SEQ ID NO 216
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 216
acgctctata caccg                                                    15

<210> SEQ ID NO 217
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 217
gtagtccagg tcgtc                                                    15

```
<210> SEQ ID NO 218
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 218
gacgactgac taggt                                                     15

<210> SEQ ID NO 219
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 219
gcataggaca ggcag                                                     15

<210> SEQ ID NO 220
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 220
tcgcaccaca accat                                                     15

<210> SEQ ID NO 221
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 221
actcaagcac ctctc                                                     15

<210> SEQ ID NO 222
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 222
ggtcgcatga taagg                                                     15

<210> SEQ ID NO 223
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 223
gtatcgtata ggtcg                                                     15

<210> SEQ ID NO 224
<211> LENGTH: 15
<212> TYPE: DNA
<213> ORGANISM: Artificial Sequence
<220> FEATURE:
<223> OTHER INFORMATION: Synthetic polynucleotide
```

```
<400> SEQUENCE: 224
tccgttgcta taatc                                                    15

<210> SEQ ID NO 225
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 225
ggttgattca agaat                                                    15

<210> SEQ ID NO 226
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 226
gcatggatac cagcg                                                    15

<210> SEQ ID NO 227
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 227
gtccaggcat tcgtc                                                    15

<210> SEQ ID NO 228
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 228
tcgtgtgagt ctcgt                                                    15

<210> SEQ ID NO 229
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 229
acaacggtgc gactg                                                    15

<210> SEQ ID NO 230
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 230
attctctgcc gagag                                                    15

<210> SEQ ID NO 231
<211> LENGTH: 15
```

```
<212> TYPE: DNA
<213> ORGANISM: Artificial Sequence
<220> FEATURE:
<223> OTHER INFORMATION: Synthetic polynucleotide

<400> SEQUENCE: 231
cgtatcgagg tgccg                                                      15

<210> SEQ ID NO 232
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 232
gttgttcgtg tgtcg                                                      15

<210> SEQ ID NO 233
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 233
gtcctgtcta gtccg                                                      15

<210> SEQ ID NO 234
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 234
gatgacctgt ccatg                                                      15

<210> SEQ ID NO 235
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 235
agcgtgcagt ggaag                                                      15

<210> SEQ ID NO 236
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 236
ggctctgaac ctatc                                                      15

<210> SEQ ID NO 237
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 237
```
gagctggaca ggtgg                                                      15

<210> SEQ ID NO 238
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 238
cacagtcctc catgc                                                      15

<210> SEQ ID NO 239
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 239
ccgcactctg ataat                                                      15

<210> SEQ ID NO 240
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 240
ttgataagcc gacgg                                                      15

<210> SEQ ID NO 241
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 241
cgcttggcta atagg                                                      15

<210> SEQ ID NO 242
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 242
gaagatcgca attag                                                      15

<210> SEQ ID NO 243
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 243
tctacaccgc tgaag                                                      15

<210> SEQ ID NO 244
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 244
cgctcctaga tgttc					15

<210> SEQ ID NO 245
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 245
tccgtggctt actgg					15

<210> SEQ ID NO 246
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 246
gactactgct caccg					15

<210> SEQ ID NO 247
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 247
gtgaagtgac tgagg					15

<210> SEQ ID NO 248
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 248
tagattgttg cgtgc					15

<210> SEQ ID NO 249
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 249
ccgacatccg ctgtg					15

<210> SEQ ID NO 250
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 250
tcaagccttg cggag					15

```
<210> SEQ ID NO 251
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 251
cctgcttccg tgatg                                            15

<210> SEQ ID NO 252
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 252
ttattgccac cagtg                                            15

<210> SEQ ID NO 253
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 253
cacgttcaac tggcg                                            15

<210> SEQ ID NO 254
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 254
ccagttagca agacg                                            15

<210> SEQ ID NO 255
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 255
gctggaactc ataag                                            15

<210> SEQ ID NO 256
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 256
tgctcgttgg tccag                                            15

<210> SEQ ID NO 257
<211> LENGTH: 15
<212> TYPE: DNA
<213> ORGANISM: Artificial Sequence
<220> FEATURE:
<223> OTHER INFORMATION: Synthetic polynucleotide
```

<400> SEQUENCE: 257
agtcttcgga taccg                                               15

<210> SEQ ID NO 258
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 258
tggacctcta attgc                                               15

<210> SEQ ID NO 259
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 259
catcgactca ccttc                                               15

<210> SEQ ID NO 260
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 260
gcggattctc agtgg                                               15

<210> SEQ ID NO 261
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 261
gaacacgcac atggc                                               15

<210> SEQ ID NO 262
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 262
gttgctgtgt ggatc                                               15

<210> SEQ ID NO 263
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 263
ccagcaatcc tacag                                               15

<210> SEQ ID NO 264

```
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 264
accgcagaga ggtag                                                    15

<210> SEQ ID NO 265
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 265
acgcttatgg cagtg                                                    15

<210> SEQ ID NO 266
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 266
gttgcgtagt gatgc                                                    15

<210> SEQ ID NO 267
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 267
tgattcctga gtccg                                                    15

<210> SEQ ID NO 268
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 268
gcacgagatc cttgc                                                    15

<210> SEQ ID NO 269
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 269
ctagcacctc gtaat                                                    15

<210> SEQ ID NO 270
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 270
```
tcaatggacg gatgc                                                15

<210> SEQ ID NO 271
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 271
cgtataccga gttgg                                                15

<210> SEQ ID NO 272
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 272
gcctattgta ctgcg                                                15

<210> SEQ ID NO 273
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 273
cacaccatcg tattc                                                15

<210> SEQ ID NO 274
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 274
tatcctgtca acggc                                                15

<210> SEQ ID NO 275
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 275
atgcttcaca cggtg                                                15

<210> SEQ ID NO 276
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 276
gcttgccgta gcgtg                                                15

<210> SEQ ID NO 277
<211> LENGTH: 15
<212> TYPE: DNA

```
<213> ORGANISM: Artificial Sequence
<220> FEATURE:
<223> OTHER INFORMATION: Synthetic polynucleotide

<400> SEQUENCE: 277
tgtccgcctg catgg                                                    15

<210> SEQ ID NO 278
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 278
gtcgatattg atccg                                                    15

<210> SEQ ID NO 279
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 279
ggaacactct actgc                                                    15

<210> SEQ ID NO 280
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 280
aagcggaagg tatag                                                    15

<210> SEQ ID NO 281
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 281
ctacttccga atcag                                                    15

<210> SEQ ID NO 282
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 282
ccacggagcc ttctc                                                    15

<210> SEQ ID NO 283
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 283
gcacacgatc atctg                                                    15
```

<210> SEQ ID NO 284
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 284
ctgttacgtc cgctg                                                         15

<210> SEQ ID NO 285
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 285
ctggtgtcac gtctc                                                         15

<210> SEQ ID NO 286
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 286
acgctgtggc gattc                                                         15

<210> SEQ ID NO 287
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 287
actgttcgac acgtc                                                         15

<210> SEQ ID NO 288
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 288
gctccagtcg taatc                                                         15

<210> SEQ ID NO 289
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 289 tattatggt                                                                 9

<210> SEQ ID NO 290
<211> LENGTH: 9
<212> TYPE: DNA
<213> ORGANISM: Artificial Sequence
<220> FEATURE:

-continued

<223> OTHER INFORMATION: Synthetic polynucleotide

<400> SEQUENCE: 290 tagctacct                                                                  9

<210> SEQ ID NO 291
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 291 attgttcat                                                                  9

<210> SEQ ID NO 292
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 292 ccaccgaat                                                                  9

<210> SEQ ID NO 293
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 293 catcagttg                                                                  9

<210> SEQ ID NO 294
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 294 ccttgagag                                                                  9

<210> SEQ ID NO 295
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 295 atcaggaag                                                                  9

<210> SEQ ID NO 296
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 296 cgaagtagc                                                                  9

```
<210> SEQ ID NO 297
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 297 ttaaccgac                                                                  9

<210> SEQ ID NO 298
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 298 gttcataca                                                                  9

<210> SEQ ID NO 299
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 299 gacgaagaa                                                                  9

<210> SEQ ID NO 300
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 300 tgcctctgt                                                                  9

<210> SEQ ID NO 301
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 301 gagatggat                                                                  9

<210> SEQ ID NO 302
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 302 accatagtg                                                                  9

<210> SEQ ID NO 303
<211> LENGTH: 9
<212> TYPE: DNA
<213> ORGANISM: Artificial Sequence
<220> FEATURE:
<223> OTHER INFORMATION: Synthetic polynucleotide
```

```
<400> SEQUENCE: 303 gtacgaatg                                                                9

<210> SEQ ID NO 304
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 304 aaggagacg                                                                9

<210> SEQ ID NO 305
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 305 ccattaacc                                                                9

<210> SEQ ID NO 306
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 306 tctccttac                                                                9

<210> SEQ ID NO 307
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 307 atctcacca                                                                9

<210> SEQ ID NO 308
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 308 cgtaactaa                                                                9

<210> SEQ ID NO 309
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 309 agactggct                                                                9

<210> SEQ ID NO 310
<211> LENGTH: 9
```

```
<212> TYPE: DNA
<213> ORGANISM: Artificial Sequence
<220> FEATURE:
<223> OTHER INFORMATION: Synthetic polynucleotide

<400> SEQUENCE: 310 aataccact                                                                  9

<210> SEQ ID NO 311
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 311 gcgaacgtt                                                                  9

<210> SEQ ID NO 312
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 312 gcatcgagt                                                                  9

<210> SEQ ID NO 313
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 313 gatgacgta                                                                  9

<210> SEQ ID NO 314
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 314 gagcagaac                                                                  9

<210> SEQ ID NO 315
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 315 gacaccccg                                                                  9

<210> SEQ ID NO 316
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 316
``` gttgttcga                                                                        9

<210> SEQ ID NO 317
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 317 tttatatgt                                                                        9

<210> SEQ ID NO 318
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 318 ttgacatca                                                                        9

<210> SEQ ID NO 319
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 319 ttatccccc                                                                        9

<210> SEQ ID NO 320
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 320 tgtgaccag                                                                        9

<210> SEQ ID NO 321
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 321 ctgcattat                                                                        9

<210> SEQ ID NO 322
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 322 ttgtagctg                                                                        9

<210> SEQ ID NO 323
<211> LENGTH: 9
<212> TYPE: DNA
<213> ORGANISM: Artificial Sequence

```
<220> FEATURE:
<223> OTHER INFORMATION: Synthetic polynucleotide

<400> SEQUENCE: 323 gccgttatc                                                                    9

<210> SEQ ID NO 324
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 324 gaatacaac                                                                    9

<210> SEQ ID NO 325
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 325 aggagaata                                                                    9

<210> SEQ ID NO 326
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 326 catctaaga                                                                    9

<210> SEQ ID NO 327
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 327 tcaatacaa                                                                    9

<210> SEQ ID NO 328
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 328 cgataagtt                                                                    9

<210> SEQ ID NO 329
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 329 ttgacaagt                                                                    9
```

<210> SEQ ID NO 330
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 330 tgtagttct                                                                 9

<210> SEQ ID NO 331
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 331 gcctatcct                                                                 9

<210> SEQ ID NO 332
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 332 ggcggcaat                                                                 9

<210> SEQ ID NO 333
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 333 ttacggcca                                                                 9

<210> SEQ ID NO 334
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 334 ggaatcctc                                                                 9

<210> SEQ ID NO 335
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 335 ctcatgtta                                                                 9

<210> SEQ ID NO 336
<211> LENGTH: 9
<212> TYPE: DNA
<213> ORGANISM: Artificial Sequence
<220> FEATURE:
<223> OTHER INFORMATION: Synthetic polynucleotide

```
<400> SEQUENCE: 336 gattgatta                                                                9

<210> SEQ ID NO 337
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 337 atatactga                                                                9

<210> SEQ ID NO 338
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 338 cgctccttc                                                                9

<210> SEQ ID NO 339
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 339 agtacgcga                                                                9

<210> SEQ ID NO 340
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 340 cacggatct                                                                9

<210> SEQ ID NO 341
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 341 tcctggtat                                                                9

<210> SEQ ID NO 342
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 342 aggtcttcg                                                                9

<210> SEQ ID NO 343
```

```
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 343 tggatgctc                                                                  9

<210> SEQ ID NO 344
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 344 tgagtaatt                                                                  9

<210> SEQ ID NO 345
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 345 tctcatatt                                                                  9

<210> SEQ ID NO 346
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 346 tcgaacata                                                                  9

<210> SEQ ID NO 347
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 347 tcatactac                                                                  9

<210> SEQ ID NO 348
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 348 tatcgacgt                                                                  9

<210> SEQ ID NO 349
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 349
``` tagaccagg                                                                9

<210> SEQ ID NO 350
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 350 taatgtgga                                                                9

<210> SEQ ID NO 351
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 351 attagtatg                                                                9

<210> SEQ ID NO 352
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 352 atcctatcc                                                                9

<210> SEQ ID NO 353
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 353 ttccaaggc                                                                9

<210> SEQ ID NO 354
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 354 gtagcatcc                                                                9

<210> SEQ ID NO 355
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 355 cctacggcc                                                                9

<210> SEQ ID NO 356
<211> LENGTH: 9
<212> TYPE: DNA

<213> ORGANISM: Artificial Sequence
<220> FEATURE:
<223> OTHER INFORMATION: Synthetic polynucleotide

<400> SEQUENCE: 356 tacgcttga                                                                9

<210> SEQ ID NO 357
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 357 cttggcgac                                                                9

<210> SEQ ID NO 358
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 358 cttaaaccg                                                                9

<210> SEQ ID NO 359
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 359 ctctgttgt                                                                9

<210> SEQ ID NO 360
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 360 ctctgttgt                                                                9

<210> SEQ ID NO 361
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 361 cgtttcaca                                                                9

<210> SEQ ID NO 362
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 362 cgcttctaa                                                                9

<210> SEQ ID NO 363
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 363 ccgactgct                                                                  9

<210> SEQ ID NO 364
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 364 catccagtc                                                                  9

<210> SEQ ID NO 365
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 365 cagctccga                                                                  9

<210> SEQ ID NO 366
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 366 caacaacgt                                                                  9

<210> SEQ ID NO 367
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 367 cattagact                                                                  9

<210> SEQ ID NO 368
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 368 ccagcactt                                                                  9

<210> SEQ ID NO 369
<211> LENGTH: 9
<212> TYPE: DNA
<213> ORGANISM: Artificial Sequence
<220> FEATURE:

<223> OTHER INFORMATION: Synthetic polynucleotide

<400> SEQUENCE: 369 gtgatgtac                                                                9

<210> SEQ ID NO 370
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 370 gtagtcgtc                                                                9

<210> SEQ ID NO 371
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 371 ggtccaact                                                                9

<210> SEQ ID NO 372
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 372 ggcgccata                                                                9

<210> SEQ ID NO 373
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 373 ggagagcac                                                                9

<210> SEQ ID NO 374
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 374 gctctgcaa                                                                9

<210> SEQ ID NO 375
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 375 attacacgc                                                                9

```
<210> SEQ ID NO 376
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 376 agttgaaat                                                                9

<210> SEQ ID NO 377
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 377 aggcccttt                                                                9

<210> SEQ ID NO 378
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 378 agatgagcg                                                                9

<210> SEQ ID NO 379
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 379 actcttctt                                                                9

<210> SEQ ID NO 380
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 380 accattatt                                                                9

<210> SEQ ID NO 381
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 381 acagactca                                                                9

<210> SEQ ID NO 382
<211> LENGTH: 9
<212> TYPE: DNA
<213> ORGANISM: Artificial Sequence
<220> FEATURE:
<223> OTHER INFORMATION: Synthetic polynucleotide
```

```
<400> SEQUENCE: 382 aattgtctg                                                                9

<210> SEQ ID NO 383
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 383 aaggcctca                                                                9

<210> SEQ ID NO 384
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 384 aacgaacag                                                                9
```

METHODS AND SYSTEMS FOR PERFORMING SINGLE CELL ANALYSIS OF MOLECULES AND MOLECULAR COMPLEXES

CROSS-REFERENCE TO RELATED APPLICATIONS

The present application claims priority to U.S. Provisional Application No. 62/562,684, entitled "Methods and Devices for Studying Single Cell Dynamics and Interactions of Nucleic Acids", filed on Sep. 25, 2017 and to U.S. Provisional Application No. 62/562,894 entitled "Methods and Devices for Single-Cell Sequencing and Analysis of Nucleic Acids" filed on Sep. 25, 2017, the entire disclosure of each of which is incorporated herein by reference. This application may be also be related to U.S. application Ser. No. 16/141,707 entitled "Device for Additive Delivery of Reagents and Related Methods and Systems" filed on Sep. 25, 2018, and to U.S. application Ser. No. 15/466,861 entitled "Methods for Identifying Macromolecule Interactions" filed on Mar. 22, 2017, the entire disclosure of each of which is herein incorporated by reference in its entirety.

STATEMENT OF GOVERNMENT GRANT

This invention was made with government support under Grant No. HL130007 and under Grant No. EB012946 awarded by the National Institutes of Health. The government has certain rights in the invention.

FIELD

The present disclosure generally relates to biochemistry, cellular biology and molecular biology, and more specifically to methods and systems for performing single-cell analysis of molecules and molecular complexes.

BACKGROUND

Recent developments in biology have highlighted the importance of the correlation between genetic and biochemical characteristics of single cells and corresponding cellular phenotype.

Those characteristics however are not seen when studying a bulk population of cells in view of the heterogeneity seen in both eukaryotic and prokaryotic cell populations.

As a consequence, it's becoming increasingly important to identify techniques allowing detection at a single-cell level of cellular features which are currently detected only for bulk samples, as well as other features impacting the physiology of the cell.

Despite the advancement of the technology, developing effective techniques which allow detection genomic or expression characteristics of individual cells themselves currently effectively detected in averaged data from a bulk sample, is still challenging.

SUMMARY

Provided herein are methods and systems for single cell marking of molecular complexes comprising cell specific or organelle specific tags which in several embodiment enable detection and analysis of molecules and/or molecular complexes at a single cell level.

According to a first aspect, a method is described to perform single-cell marking of a nucleic acid and/or protein in a sample comprising a plurality of cells. The method comprises:

permeabilizing a cell from the plurality of cells or an organelle thereof, to provide a permeabilized cell or organelle thereof; and in-cell or in-organelle barcoding nucleic acid and/or protein complexes of the permeabilized cell or organelle thereof, to provide in-cell or in-organelle single-cell marked nucleic acid and/or protein complexes comprising a single-cell specific marker.

According to a second aspect, a system is described to perform single-cell marking of nucleic acid and/or protein complexes in a sample comprising a plurality of cells. The system comprises permeabilization reagents and reagents for tagging molecular complexes for simultaneous combined or sequential use in any one of the methods to perform single-cell marking of nucleic acid and/or protein complexes herein described.

The methods and systems and related compositions, herein described in several embodiments allow study at a single cell level, of the organization and structure/function relationships, and in particular of the three-dimensional organization of the nucleus or other organelles (e.g. in different cellular states).

In particular by achieving compartmentalization of both the cell and related organelles such as the nucleus, methods and systems and related compositions, herein described allow in several embodiments to simultaneously map mRNA levels in the cell in correlation with the genomic configuration in the nucleus.

Additionally, with respect to mapping chromatin organization, methods and systems and related compositions, herein described allow attaining more contacts in a single cell compared to previous methods as it sets up the user to move away from proximity ligation to measure complex contacts in-nucleus.

The methods and systems and related compositions herein described further allow in several embodiments, single cell detection and/or analysis of different genetic and/or or expression characteristics commonly seen in averaged data from a bulk sample.

The methods and systems and related compositions herein described in several embodiments allow single cell analysis of nucleic acid and/or protein molecules which can be used to directly link genotype and expression data that occur simultaneously in a cell.

The methods and systems and related compositions, herein described allow for increased throughput, further allowing addition of more than two barcoded oligos to nucleic acids in-nuclei with respect with conventional approaches only relying on combined use of transposase (barcode 1) and PCR primers (barcode 2).

The methods and systems and related compositions herein described can be used in connection with various applications wherein single cell analysis is desired, in particular in connection with single cell detection, identification and/or analysis of molecules or molecular complexes, organization of nucleic acid and/or protein and related structure/function relationships. For example, the methods and systems and related compositions, herein described can be used in RNA-seq, rare cell identification from a population of cells, de novo genome assembly and to develop diagnostic and therapeutic approaches and tools to allow for rapid screening of diseased cells at an early stage (e.g. leukemia, tumor cells), rapid environmental screening of rare microbes in a community, find early stages of neurological disorders (e.g. Parkinsons, Huntingtons), and determine antibiotic resistance of bacterial organisms (e.g. to detect which bacterial cells in a population start becoming resistant to an antibiotic). Additional exemplary applications include uses of the methods and systems and related compositions, herein described in several fields including basic biology research, applied biology, bio-engineering, aetiology, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 7 shows the normalized percent coverage as a function of chromosome on different clusters. Panel (A): An analysis of percent coverage as a function of chromosome on all clusters having greater than 10,000 fragments. Panel (B): An analysis of percent coverage as a function of chromosome on the largest barcoded cluster (65,523 fragments).

FIG. 9 shows microscopic images of exemplary isolated crosslinked cells provided in accordance with an embodiment of the disclosure.

FIG. 10 Panel B shows a gel of libraries from single cells that were loaded at 30% occupancy on a SlipChip device containing 48 wells, barcoded in their own respective well, pooled together and amplified.

(FIG. 2 from Le et al. [3])

FIG. 25 shows a list of exemplary DPM tags. Format and DNA sequences of barcodes are derived from Quinodoz et al. [1]. Shaded region contains regions of DNA tags, which can be switched out for other tag sequences. The following sequences for the shaded regions correspond to one strand of the DNA sequence, but the complementary sequence can be inferred from the sequence provided. Overhangs are indicated with sequences in bold or in underlined fonts.

FIG. 26 shows a list of exemplary odd adaptor sequences. Format and DNA sequences of barcodes are derived from Quinodoz et al. [1]. Shaded region contains regions of DNA tags, which can be switched out for other tag sequences. The following sequences for the shaded regions correspond to one strand of the DNA sequence, but the complementary sequence can be inferred from the sequence provided. Overhangs are indicated with sequences in bold or in underlined fonts.

FIG. 27 shows a list of exemplary even adaptor sequences. Format and DNA sequences of barcodes are derived from Quinodoz et al. [1]. Shaded region contains regions of DNA tags, which can be switched out for other tag sequences. The following sequences for the shaded regions correspond to one strand of the DNA sequence, but the complementary sequence can be inferred from the sequence provided. Overhangs are indicated with sequences in bold or in underlined fonts.

FIG. 28 shows a list of exemplary Y-end adaptor sequences. Format and DNA sequences of barcodes are derived from Quinodoz et al. [1]. Shaded region contains regions of DNA tags, which can be switched out for other tag sequences. The following sequences for the shaded regions correspond to one strand of the DNA sequence, but the complementary sequence can be inferred from the sequence provided. Overhangs are indicated with sequences in bold or in underlined fonts.

DETAILED DESCRIPTION

Figure 1:
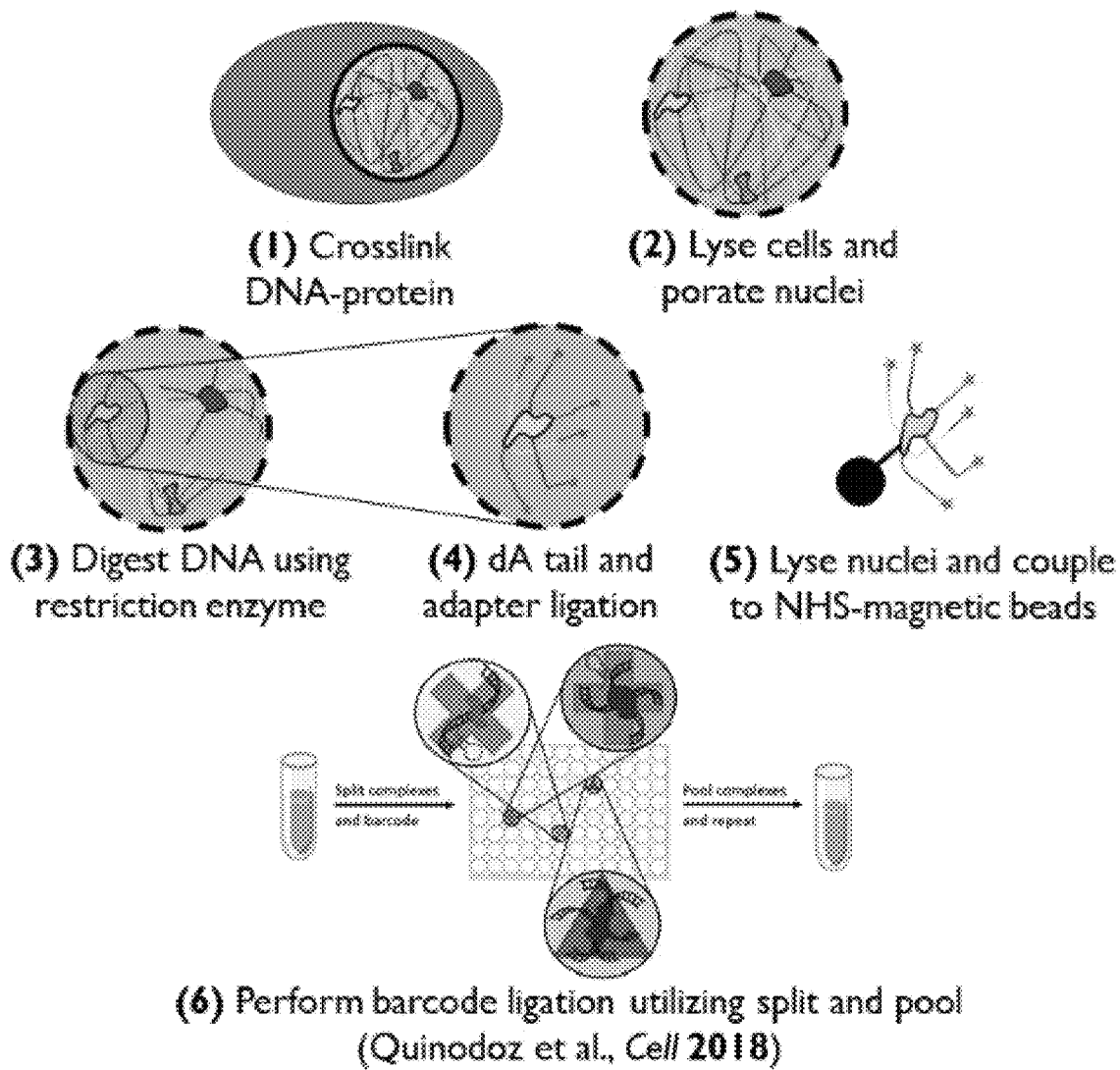
FIG. 1 shows a schematic illustrating an exemplary workflow in which methods and systems of the instant disclosure are used to select and validate RNA markers which can be used for single cell phenotypic measurements of antibiotic susceptibility and resistance.

Provided herein are methods and systems for performing single cell marking of molecules and/or molecular complexes inside individual cells which enables related processing and/or analysis at a single cell level.

The wording "cell" as used herein indicates a basic membrane-bound structural, functional, and biological unit of all known living organisms. Cells typically consist of cytoplasm enclosed within a membrane, which contains many biomolecules such as proteins and nucleic acids and possibly organelles such as nuclei, and mitochondria. Cells can form unicellular organism (consisting of a single cell; including bacteria) or multicellular organism (consisting of a plurality of cells including plants and animals). Most plant and animal cells are visible only under a microscope, with dimensions between 1 and 100 micrometres. A single cell is often a complete organism in itself, such as a bacterium or yeast. Other cells acquire specialized functions as they mature.

The wording "single cell" as used herein indicates a referenced activity or event occurring at the single cell level. Referenced activities comprises qualitative or quantitative detection of molecules, biochemical reactions, cell type, cell states, and additional events identifiable by a skilled person.

In particular, "single cell analysis" indicates an analysis performed at the single cell level, such as examination of nature, features and/or relations of molecules, complexes and/or organelles. Exemplary analyses comprise the study of genetics genomics, transcriptomics, proteomics and/or metabolomics as well rare cells/events from a population of cells, unique responses to cells in response to stimuli (e.g. specific differentiated cells, response to drugs/antibiotics), and other "omics" studies (e.g. epigenomics) and additional analysis identifiable by a skilled person.

In embodiments herein described, methods and systems are described which allow single cell marking nucleic acid and/or protein in a sample comprising a plurality of cells.

The term "mark" "marking" and "marker as used herein, indicate compounds or molecule which provide a reference item with a characteristic enabling the related identification and detection.

Accordingly, markers in the sense of the disclosure comprise any compounds or molecule (such as a metabolite) which is a distinctive biological or biologically derived indicator of a biological process, event, condition or feature such as a genetic or cellular feature. In particular, markers in the sense of the disclosure can be indicators of cellular, biochemical or molecular state of a cell and related physiology.

Exemplary markers in the sense of the disclosure comprise barcodes. The term "barcode" when used as a noun with reference to a marker, indicates a series of one or more tags configured to provide a substrate attaching the barcode with a unique marker enabling the related identification and detection. The term "tags" indicate a compound configured to be attached to a reference substrate such as a compound, molecule or cell to allow identification of the substrate. Exemplary tags comprise protein tags such as peptide sequences configured to be grafted onto a recombinant protein (e.g. antibodies), and nucleic acid tags such as oligonucleotide configured to be grafted to a recombinant protein or nucleic acid. In preferred embodiments, a barcode is either formed by one tag, or comprises a series of two or more tags directly attached one to another to form the barcode.

The terms "detect" or "detection" as used herein indicates the determination of the existence, presence or fact of a referenced target in a limited portion of space, including but not limited to a sample, a reaction mixture, a molecular complex and a substrate. The "detect" or "detection" as used herein can comprise determination of chemical and/or biological properties of the referenced target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In methods and systems of the disclosure barcodes are used for single-cell marking of nucleic acid and/or protein of a sample comprising a plurality of cells.

The term "nucleic acid" as used herein indicates a polymeric form of nucleotides of any length, either ribonucleotides or deoxyribonucleotides, that comprise purine and pyrimidine bases, or other natural, chemically or biochemically modified, non-natural, or derivatized nucleotide bases. Nucleic acids of the embodiments of the current disclosure include Deoxyribonucleic acid (DNA), ribonucleic acid (RNA), or DNA copies of RNA (complementary DNA or cDNA), which may be isolated from natural sources, recombinantly produced, or artificially synthesized. The nucleic acids can exist as single-stranded or double-stranded and any chemical and biochemical modifications thereof, provided only that the modification does not interfere with amplification of the resulting nucleic acids. For example, the backbone of the nucleic acid can comprise sugars and phosphate groups or modified or substituted sugar or phosphate groups, and a nucleic acid may comprise modified nucleotides, such as methylated nucleotides and nucleotide analogs. A polynucleotide of 5 to 50 nucleotide is also called a protein oligomer, peptide, or oligopeptide. In particular, the term oligonucleotide usually indicates a polynucleotide with less than 30 nucleotides.

The term "protein" as used herein indicates a polypeptide with a particular secondary, tertiary and quaternary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. As used herein the term "amino acid", "amino acid monomer", or "amino acid residue" refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to forma polymer through peptide bonds by reactions between the amine group of a first amino acid and the carboxylic acid group of a second amino acid. A polypeptide of three or more amino acids is also called a protein oligomer, peptide, or oligopeptide. In particular, the terms "peptide" and "oligopeptide" usually indicate a polypeptide with less than 100 amino acid monomers.

The term "sample" as used herein indicates a limited quantity of something that is indicative of a larger quantity of that something, including but not limited to fluids from an isolate or a specimen such as biological environment, cultures, tissues, commercial recombinant proteins, synthetic compounds or portions thereof. In particular, biological sample can comprise one or more cells of any biological lineage, as being representative of the total population of similar cells in the sampled individual. Individuals biological organism that can be sampled comprise any single multicellular organism, such as plants or animals and in particular higher animals more particularly vertebrates such as mammals and in particular human beings. Exemplary biological samples comprise the following: adherent or suspension cell lines (and in particular embryonic stem cells or differentiated pluripotent stem cells), cheek tissue, whole blood, dried blood spots, organ tissue, plasma, urine, mucus, mucosal secretions, vaginal fluids and secretions, urethral fluids and secretions, feces, skin, hair, or tumor cells, among others identifiable by a skilled person. Biological samples can be obtained using sterile techniques or non-sterile techniques, as appropriate for the sample type, as identifiable by persons skilled in the art. Some biological samples can be obtained by contacting a swab with a surface on a human body and removing some material from said surface, examples include throat swab, urethral swab, oropharyngeal swab, cervical swab, vaginal swab, genital swab, anal swab. Depending on the type of biological sample and the intended analysis, biological samples can be used freshly for sample preparation and analysis or can be fixed using fixative. Preferably, in methods and systems herein described the sample comprises live cells.

In embodiments of methods and systems, single cell marking is obtained by performing in-cell or in-organelle barcoding of nucleic acid and/or protein complexes.

The term "in-cell" as used herein indicates any reference item, typically a compound molecule or reaction, performed within an individual cell without lysis of the individual cell, wherein the term "lysis" as used herein indicates the full breaking down of a cell membrane resulting in a complete breaking open of the cell or other compartment. Lysis according to the disclosure can be the result of osmotic imbalance that has caused excess water to diffuse into the cell as well as viral, enzymic, or osmotic mechanisms that compromise its integrity. A fluid containing the contents of lysed cells is called a "lysate".

The term "in-organelle" as used herein indicates any reference item, typically a compound molecule or reaction, performed within an individual organelle without lysis of the individual organelle in the sense of the disclosure. An "organelle" as used herein indicates any of structure within a cell encircled by a membrane and configured to that perform a specific function (e.g., nucleus, mitochondria, or chloroplasts). Organelle comprise closed parts within the cytosol of a cell surrounded by a double lipid layer membrane. Individual organelles are therefore separately enclosed within their own lipid membrane. Exemplary organelles comprise, nucleus, mitochondrion, and chloroplasts.

The term "barcode" or "barcoding" when used as a verb with reference to a reaction, indicates a reaction performed to covalently attach a barcode in the sense of the disclosure to the reference item, in a configuration allowing detection of the barcode. Accordingly, barcoding in the sense of the disclosure refers to coupling a unique set of tags or identifiers in order to mark molecules for downstream detection and identification. In particular, in embodiments herein described barcoding in particular refer to a coupling reaction of molecules within a same compartment such as a cell or nucleus in order to label these molecules for downstream detection and identification. In some embodiments, suitable tags or identifiers for barcoding can be oligonucleotide label. As used herein, "unique" means different from any other. Exemplary reactions that can be used to barcode a molecule in the sense of the disclosure comprise ligation binding of antibody covalently attaching an oligonucleotide, addition of DNA by transposase and additional reactions identifiable by a skilled person.

In embodiments herein described, methods and systems are directed to directly barcode nucleic acid and/or protein of the cell of the sample, rather than molecules derived therefrom (such as a complementary nucleic acid, and in particular a cDNA prepared from an RNA of the cell).

In some embodiments, a barcode can be obtained by sequential direct covalent linkage of a tag with another tag until formation of a barcode comprising a series of two or more tags directly attached one to another through covalent linkage. In those embodiments barcoding allows marking of more than two nucleic acids and/or proteins of complexes comprising more than two nucleic acid and/or proteins, thus improving detectability of the molecules in the complex, as well as allowing a more detailed analysis of complexes related contacts and components, compared with methods relying on proximity ligation.

In preferred embodiments, the methods and systems herein described are performed without performing a enzymatic intracomplex ligation step directed to include a covalent linkage between two nucleic acids and/or proteins which are attached to one another within a complex. In those enzymatic intracomplex ligation procedures, an enzymatic ligation agent is contacted with the complex after chemical modification of the ends of the nucleic acids and/or proteins of the complex to make the ends unsuitable for the reactions with the enzymatic ligation agent introducing covalent linkage in nucleic acid and/or proteins of the complex. The term "intracomplex ligation" as used herein in connection with nucleic acids and/or protein complexes, indicates a ligation of two nucleic acids and/or proteins which are attached to one another within a complex.

An exemplary enzymatic intracomplex ligation is proximity ligation. The term "proximity ligation" as used herein indicates stochastic ligation of two proximal molecules within the same complex under low DNA or protein concentrations, where an intracomplex ligation between two molecules in a complex is strongly favored to an intercomplex ligation between two molecules from different complexes. Proximity ligation is a technique that has been used to measure local protein-protein, RNA-RNA, and DNA-DNA interactions [4-6]. This ligation is performed on complexes using nucleic acid strands. In the case of protein-only complexes, antibodies conjugated to an oligonucleotide are added to bind to the proteins in solution [7, 8]. At this point, if the nucleic acids are not primed to ligate to each other, DNA modifications are performed to the end of the nucleic acid, which include 5'-phosphorylation or blunting of DNA ends—the two most common end-repair modifications. With the primed nucleic acids, ligase is then added to perform ligation of the proximal nucleic acid molecules indicating the spatial positioning of the initial target molecules.

The term "nucleic acid and/or protein complex" in the sense of the disclosure indicates nucleic acids and/or proteins attached one to the other to provide a stable molecular complex under physiological condition at a temperature between 4° C. and 37° C. Exemplary complexes sufficiently stable so the protocols described herein can be performed while at least 1% of the complex remains attached to form the complex. In some embodiments, complexes have a half live of at least 1 minute, 5 minutes, 10 minutes, 20 minutes, 60 minutes under at least one of these conditions (physiological condition at a temperature between 4° C. and 37° C.). Exemplary attachments allowing formation of a complex in the sense of the disclosure comprise stable charged interactions (e.g. positively charged histones interacting with the negatively-charged backbone of DNA) and interactions between DNA-binding domains (e.g. zinc fingers, helix-turn-helix, etc.) In particular, in complexes in the sense of the invention the nucleic acid and/or protein are attached through covalent linkage (including covalent linkage introduced by cross linking) and/or other linkages such as ionic and metallic bonds, hydrophobic interactions, as well dipole-dipole interactions, the London dispersion force and hydrogen bonding. The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material.

In embodiments, herein described, reagents to barcode nucleic acid and/or protein complexes are introduced in the cell or in the organelle following permeabilization of the cell or the organelle.

The term "permeabilize" as used herein means to render permeable a substance, substrate, enzymes, tags or other material. The term "permeable" or "penetrable" as used herein refers to the ability of a substance, substrate, enzymes, tags or other material to pass through a lipid bilayer membrane such as a cell membrane or a nuclear envelope, which is the membrane that encloses the nucleus. The term "permeable" or "penetrable" can be a relative term to indicate permeability to specific reagents (e.g. of a particular size) with respect to other reagents.

In embodiments herein described during the permeabilizing, the cell or the organelle remain structurally intact.

In particular, in embodiments herein described permeabilization can be performed by contacting the cell or organelle with a chemical agent capable of porating a cell and/or an organelle membrane at a condition while the related addition preserves the compartmentalization of crosslinked protein and nucleic acids.

In some embodiments, the chemical agent is a detergent and permeabilization can be performed by contacting the cell or organelle Pe with a buffer comprising one or more detergents.

The term "detergent" as used herein refers to an amphiphilic (partly hydrophilic/polar and partly hydrophobic/nonpolar) surfactant or a mixture of amphiphilic surfactants. Detergents can be broadly categorized according to the charge of their polar portion as "anionic" (negative charge; examples including, but not limited to alkylbenzenesulfonates and bile acids, such as deoxycholic acid), "cationic" (positive charge; examples including, but not limited to, quaternary ammonium and pyridinium-based detergents), "nonionic" (no charge; examples including, but not limited to, polyoxyethylene/PEG-based detergents such as Tween and Triton, and glycosidebased detergents such as HEGA and MEGA), and "zwitterionic" (no charge due to equal numbers of positive and negative charges on the detergent molecules; examples including, but not limited to, CHAPS and amidosulfobetaine-type detergents).

In some embodiments, suitable detergents for permeabilizing the cell, comprise Sodium Dodedcyl Sulfate (SDS), digitonin, leucoperm, saponin, and tween 20.

In some embodiments, suitable detergents for permeabilizing the organelle, and in particular the nuclear comprise nonionic detergents, Triton X-100, Nonidet-P40, Ionic detergents, Sodium Dodedcyl Sulfate (SDS), deoxycholate, sarkosyl and additional detergents identifiable by a skilled person.

Additional information on common detergents with CMCs and other properties can be found in "Detergents: Handbook & Selection Guide to Detergents & Detergent Removal" available from G-Biosciences [9]Conditions for applying detergents for permeabilization can be found for example Neugebauer 1990 [10] and Schramm et al. 2003 [11], both yielding properties, related Critical Micelle Concentrations (CMCs), and applications of detergents, and in additional reference identifiable by a skilled person.

In particular, suitable concentration of detergents for permeabilizing cells and organelle such as nuclei comprise various concentrations depending on the detergent (see e.g. sodium dodecyl sulfate at a final concentration up to 1% (see e.g. Bindu et al. 1998 [12] Additional information allowing a skilled person to identify the proper concentration and can be found in in "Detergents: Handbook & Selection Guide to Detergents & Detergent Removal" available from G-Biosciences [9] should provide all suitable detergents and their CMCs. This would allow the skilled user to fine-turn their detergent's concentrations to make sure it doesn't exceed the CMC and cause full lysis of the cell/organelle.

In embodiments herein described permeabilization allows for enzymes and other reagents to passively enter the cell membrane and perform enzymatic reactions in-cell or in-organelle as will be understood by a skilled person.

In particular, in embodiments of methods and systems herein described, following permeabilization, the cell or organelle is contacted with reagents capable of barcoding in-cell or in-organelle nucleic acid and/or protein complexes, to obtain nucleic acid and/or protein complexes comprising a single-cell specific marker, which can be cell specific or organelle specific.

In some embodiments, the in-cell or in-organelle barcoding can be performed by adding a barcode formed by a unique single tag to a single cell or a single organelle together with reagents capable of tagging the unique single tag forming the barcode to the nucleic acid and/or protein complexes of the single cell or the single organelle respectively.

As used herein, the terms "tagging" refers to the attachment of a tag to DNA, RNA, and/or protein molecules in order to mark components of nucleic acid and/or protein complex.

In some of these embodiments the tagging can be performed by direct attachment of the tag.

In some of these embodiments, reagents for in cell or in organelle tagging of nucleic acid and/or protein complexes are selected to attach a nucleic acid of the in-cell or in organelle nucleic acid/protein complexes. Generally, suitable reagents comprise a ligase, crowding agent (optional, but would help facilitate the ligation process), oligos containing tag in DNA sequence, and compatible reaction buffer for ligase (e.g. ATP, divalent cation (usually magnesium, sometimes calcium), DTT (for stability), and physiological pH conditions). An example would be NEB's T4 DNA Ligase Reaction Buffer—when used at a 1× concentration, the buffer components contain a final concentration of 50 mM Tris-HCl, 10 mM $MgCl_2$, 1 mM ATP and 10 mM DTT at pH 7.5). Additional reagents are identifiable by a skilled person upon reading of the instant disclosure.

In some of these embodiments, reagents for in cell or in organelle tagging of nucleic acid and/or protein complexes are selected to attach a protein of the in-cell or in organelle nucleic acid/protein complexes. Generally, these reagents include an antibody-bound oligo containing a specific-binding epitope, antibodies (e.g. ~150-170 kDa such as IgG), aptamers (e.g. ~12-30 kDa), Affibodies (e.g. ~6 kDa), anti-calins (e.g. ~20 kDa), monobodies (e.g. ~10 kDa), DARPins (Designed ankyrin-repeat proteins) (e.g. ~14-18 kDa), ubiquitin (e.g. ~8.5 kDa), nanobodies (single-domain antibody) (e.g. ~12-15 kDa). Additional reagents can comprise a crowding agent which can be used to facilitate the binding process, and additional reagents identifiable by a skilled person. Typically, these reagents are used at physiological pH conditions).

Additional reagents are identifiable by a skilled person upon reading of the instant disclosure.

For example, the reagents can comprise an oligonucleotide together with suitable enzymes to couple the oligonucleotide to a protein of the nucleic acid/protein complex. Oligonucleotides enable attachment of a nucleotide tag or indirectly through attachment of a protein phosphate modified (PPM) adaptor configured to ligate a nucleotide tag. The attachment of oligonucleotides to proteins can be performed as described in Los et al. [13], Singh et al. [14], Blackstock et al. [15], Kozlov et al. [16], and Solulink, the entire contents of each of which is incorporated herein by reference.

In some embodiments, the tagging can be performed by indirect attachment of the tag through intermediate molecules called "adaptor" which once coupled to a component of the in-cell or in organelle nucleic acid/protein complexes allow subsequent attachment of tags to the component.

As used herein, the term "adaptor" refers to a molecule configured to be attached to a target nucleic acid and/or protein to enable or facilitate tagging, elongation, amplification, and/or sequencing of the target nucleic acid and/or protein. Adaptors in the sense of the disclosure comprise: i) a DNA phosphate modified (DPM) adaptor which indicates a molecule configured to couple to the 5' and 3' end of a DNA molecule allowing for the DNA molecule to be effectively ligated with a subsequent nucleotide tag; ii) an RNA phosphate modified (RPM) adaptor which indicates a molecule configured to couple to the 3' end of an RNA molecule allowing for the RNA molecule to be effectively ligated with a subsequent nucleotide tag; and iii) a protein phosphate modified (PPM) adaptor which indicates a molecule configured to couple to a target protein or to an antibody of a target protein, allowing for the protein to be effectively modified for subsequent nucleotide tagging. In some embodiments, the DPM, RPM, and/or PPM adaptor molecules can include a unique nucleotide sequence thereby also serving as a nucleotide tag. DPM, RPM and PPM adaptors can be used for tagging. DPM and RPM can also be used for elongation. In addition to the adaptors, a 5' single stranded RNA (ssRNA) adaptor, for example, be used, for elongation amplification and/or sequencing of a tag or barcode. Additional elongation adapters comprise ssRNA oligonucleotide configured to attach to an RPM adaptor or an RNA tag to allow RNA molecule for amplification and sequencing after 3' nucleotide tagging of the RNA molecule.

In some embodiment, a tag or adapter can be designed to comprise overhangs specific to the complementary sequence of the target molecule of interest. The overhang can be used for subsequent processing of the nucleic acid and/or protein complex for tagging, ligation, elongation, and additional downstream analysis as will be understood by a skilled person. The overhang sequence can be at least 1 bp in length. In particular, an adapter can be an oligonucleotide configured to be coupled to nucleic acids or protein molecules. In some embodiments, the barcode is ligated onto nucleic acids with a DNA or RNA ligase via an adapter as will be understood by a person skilled in the art. Overhangs can be generated by restriction digestion as will be understood by a skilled person.

In some embodiments, the tagging is performed after additional in-cell or in organelle modifications of the nucleic acid and/or protein complexes such as tailing and in particular dA tailing, to ease tagging and/or attachment of an adaptor to the nucleic acid and/or protein complexes (see Example 6). Additional modifications comprise 5'-phosphorylation, DNA end-repair, 3C spacers to prevent ligation on a particular strand and additional modifications identifiable by a skilled person upon reading of the present disclosure.

In some embodiments of the in cell or in-organelle barcoding performed on a single cell or a single organelle the method can comprise adding a ligation adapter molecule to the single cell or the single organelle. In those embodiments, the ligation adaptor molecule configured to modify at least one end of each of the DNA, RNA, and/or protein molecules and capable of ligating to the unique barcode.

In some embodiments, the in-cell or in-organelle barcoding can be performed by split and pool tagging directed to barcode a plurality of cells or organelles.

In those embodiments, the method can comprise
a) distributing the cells or organelles into a plurality of initial suspensions;
b) adding a unique initial nucleotide tag to each of the initial suspensions to perform in cell or in organelle tagging of the in cell or in organelle nucleic acid and/or protein complexes in the respective initial suspension and thereby form a plurality of tagged initial suspensions; and
c) pooling the plurality of tagged initial suspensions to form an initial tagged pool.

The method further comprises
d) distributing the initial tagged pool into a plurality of additional suspensions;
e) adding a unique additional nucleotide tag to each of the plurality of additional suspensions to perform in cell or in organelle tagging of the in cell or in organelle nucleic acid and/or protein complexes in the respective additional suspension and thereby form a plurality of tagged additional suspensions; and
f) pooling the plurality of tagged additional suspensions to form an additional tagged pool.

The method also comprises
g) repeating steps d) to f) replacing the initial tagged pool with the additional tagged pool, to tag the nucleic acid and/or protein complexes of the cell or organelle with a cell specific or an organelle specific barcode respectively, thereby obtaining a barcoded cell or organelle pool.

As used herein, "distributing" and "sorting" are used interchangeably to refer to the division of a whole quantity into a plurality of parts. For example, distributing or sorting a suspension involves the division of the whole suspension into multiple smaller suspensions. As used herein, suspension refers to a liquid heterogeneous mixture. A suspension can refer to a liquid mixture comprising isolated and permeabilized cells or organelles. A suspension can refer to a cell lystate having all of its cellular molecules in a liquid mixture.

Distribution or sorting of the cells or organelles can be performed using any suitable approach identifiable to a skilled person. The suspension can be distributed or sorted into any number of sorted suspensions as will be understood by a skilled person. An increase in the number of sorted suspensions will increase the probability of sorting individual cells or organelles thereof apart from each other.

For example, the distribution or sorting can be accomplished using 96-well plate, thereby resulting in 96 suspensions and 96 unique nucleotide tags. As used herein, a "well" refers to the well of a 96-plate, however, any number of wells or plates may be used. A well may also refer to the well of a tube or any similar vessel capable of holding the sorted suspension separate from other sorted suspensions. For example, a well may also include a flat surface.

In some embodiments, after the distributing of step a) or d) and before the tagging of step b) and/or e) the method can further comprise adding an adaptor and/or performing in-cell or in organelle modifications of the nucleic acid and o/r protein complexes such as tailing and in particular dA tailing. Additional modifications comprise 5'-phosphorylation, DNA end-repair, 3C spacers to prevent ligation on a particular strand and additional modifications identifiable by a skilled person upon reading of the present disclosure In some embodiments the method can comprise adding an adaptor and/or reagent to perform the additional modifications to the initial suspension and/or the additional suspension of steps a) or d). in particular in some of these embodiments the adaptor can be a ligation adaptor molecule configured to modify at least one end of each of the DNA, RNA, and/or protein molecules in the respective suspension and capable of ligating to the unique initial and/or additional nucleotide tag.

Following the tagging of step b) and e) the method comprises the pooling steps c) and f) As used herein, "pooling" refers to collecting and mixing together a plurality of components. For example, pooling of suspensions includes mixing multiple suspensions into one larger, pooled suspension.

In some embodiments, the initial tagged pool and/or the additional tagged pool can be mixed thoroughly prior to redistribution to ensure a separation of individual cell or organelle.

In some embodiments, the additional nucleotide tags are capable of ligating to any of the previously ligated nucleotide tags.

In embodiments of split and pool barcoding, the pooling, distributing (sorting), and tagging is performed until the number of unique tags attached to the nucleic acid and/or protein complexes forms a barcode.

In some embodiments, in-cell or in-organelle barcoding comprises a series of tagging, pooling, and sorting of nuclei such that molecular complexes within a single cell or an organelle thereof sort together and thereby receive the same set of nucleotide tags, and therefore receive the same barcode, and molecule complexes that do not belong to the same nucleus receive a different set of nucleotide tags, and therefore receive different barcodes. Using the split-and-pool method, the probability that two cells or organelles thereof including the molecules therein receive the same tags decreases exponentially with each addition round of tagging and sorting. Molecules having the same barcode can then be identified by sequencing and matching identical barcodes.

In some embodiments, after the last nucleotide tag forming the barcode is added, the barcoded cell or organelle pool can be redistributed again into a plurality of barcoded cell or organelle pool suspensions for the addition of a terminal nucleotide tag. A terminal tag can provide an additional unique sequence and may also provide a primer site for amplification. In those embodiments the method further comprises h) distributing the barcoded cell or organelle pool into a plurality of barcoded suspensions;
i) adding a unique terminal nucleotide tag to each of the plurality of barcoded suspensions to perform in cell or in organelle terminal tagging of the in cell or in organelle nucleic acid and/or protein complexes in the respective barcoded suspension and thereby form a plurality of terminally tagged barcoded suspensions; and
j) pooling the plurality of terminally tagged barcoded suspensions to form a terminally tagged barcoded pool.

In some embodiments, after the barcoding the method can further comprise lysing the barcoded cells or the organelle pool of step g) or the terminally tagged barcoded pool of step j) to provide a barcoded complex pool or a terminally tagged barcoded pool.

In some embodiments, the barcoded complex pool or the terminally tagged barcoded pool can be processed for further analysis.

For example, in some embodiments the method can further comprise sequencing each barcode of the barcoded complex pool or the terminally tagged barcoded pool; and detecting the nucleic acid and/or protein molecules tagged with a same barcode in a barcoded complex pool or the terminally tagged barcoded pool.

In some embodiments of the disclosure wherein the barcoding is performed by a method comprising steps a) to g) and optionally steps h) to J), a barcode is obtained by sequentially attaching a series of tags one to another to provide a barcode formed by a series of two or more tags directly attached one to another through covalent linkage. In those embodiments, the barcode is provided to a complex formed in the sample without performing any intracomplex ligation, such as a proximity ligation or further ligation among nucleic acid and/or protein within a same complexes.

In these embodiments, barcoding allows marking of more than two nucleic acids and/or proteins of complexes comprising more than two nucleic acid and/or proteins thus improving detectability of the molecules in the complex, as well as allowing a more detailed analysis of complexes related contacts and components, compared with methods solely relying on proximity ligation.

In these embodiments, the methods herein described provide nucleic acid and/or protein complexes resulting in fewer than 20%, 10%, 5%, 2%, 1% of the nucleic acid from the complexes, that contains two or more unique sequences (excluding repeat sequences that occur multiple times in the genome/transcriptome) that align to two or more unique regions of a reference genome (for DNA), transcriptome (for RNA), or the reference oligonucleotide sequence (for proteins). During downstream sequence alignment, the percentage is calculated with respect to the total number of detected nucleic acid aligned.

In these embodiments, the barcoded complexes are configured to allow downstream detection of nucleic acid and/or proteins from said complexes at at least 0.01% of analyzed reads, at least 0.1%, at least 1%, at least 3%, at least 10% of analyzed reads.

In some embodiments, the method can further comprise amplifying a barcode of the of the barcoded complex pool or the terminally tagged barcoded pool e.g. to make a library and then sequence the amplified tags.

In some embodiments, the sequencing can be performed by any next-generation sequencing techniques identifiable to a skilled person. In some embodiments, the sequencing can be performed by paired-end sequencing. Paired-end sequencing allows one to sequence both ends of a fragment and generate high-quality alignable sequence data. Additional exemplary sequencing comprises single-end sequencing, Sanger sequencing, pyrosequencing, shotgun sequencing and additional sequencing identifiable by a skilled person.

In some embodiments, barcoded complexes of the barcoded complex pool can be isolated from the barcoded complex pool, for example on magnetic beads or other suitable support having a surface presenting a reactive group specific, yet general enough, (e.g. an ester group on the solid surface to react with all primary amine groups on protein-based complexes) to immobilize complexes over multiple rounds of split-and-pool.

In some embodiments, the method further comprises lysing the barcoded cell or organelle pool to provide a barcoded cell or organelle lysate comprising a mixture of barcoded nucleic acids and/or protein complexes. The nucleic acids and/or protein complexes are each barcoded with a single-cell specific barcode, which is cell specific or organelle specific.

The lysing can be performed by viral, enzymatic, and/or osmotic mechanisms that compromise the integrity of the cell, to form a cell or organelle lysate. In some embodiments, lysing can be performed with a lytic reagent such as detergent.

In some embodiments of the methods herein described, following the lysing, the mixture of barcoded nucleic acids and/or protein complexes are further barcoded to obtain a plurality of nucleic acid and/or protein complexes each barcoded with a complex-specific barcode, i.e. a barcode specific for each nucleic acid and/or protein complex. By performing the second barcoding, molecules forming a complex receive the same barcode, while molecules from different complexes receive different barcodes.

In some embodiments, adding a complex-specific barcode to the nucleic acid and/or protein complexes already barcoded with a single-cell specific barcode can be performed using split-and-pool approach described above.

In particular, the method further comprises:
i) distributing the barcoded cell or organelle lysate into a plurality of initial complexes suspensions, the barcoded cell or organelle lysate comprising barcoded nucleic acids and/or protein complexes;
ii) adding a unique initial nucleotide tag to each of the initial complexes suspensions to perform tagging of the barcoded nucleic acid and/or protein complexes in the respective initial complexes suspension and thereby form a plurality of tagged initial complexes suspensions; and
iii) pooling the plurality of tagged initial complexes suspensions to form an initial tagged complexes pool.

As used herein, the term "complexes suspension" refers to a liquid heterogeneous mixture of nucleic acid and/or protein complexes already barcoded with a single-cell or single-organelle specific barcode.

The initial nucleotide tag can be referred to as an "odd" nucleotide tag (see exemplary odd nucleotide tags in FIG. 27)

The method further comprises
iv) distributing the initial tagged complexes pool into a plurality of additional complexes suspensions;
v) adding a unique additional nucleotide tag to each of the plurality of additional complexes suspensions to perform tagging of the barcoded nucleic acid and/or protein complexes in the respective additional complexes suspension and thereby form a plurality of tagged additional complexes suspensions; and
vi) pooling the plurality of tagged additional complexes suspensions to form an additional tagged complexes pool.

The additional nucleotide tag can be referred to as an "even" nucleotide tag (see exemplary even nucleotide tags in FIG. 28).

The method also comprises
vii) repeating steps iv) to vi) replacing the initial tagged complexes pool with the additional tagged complexes pool, to tag the nucleic acid and/or protein complexes with a complex-specific barcode respectively, thereby obtaining a double-barcoded pool of nucleic acids and/or protein complexes.

In some embodiments, the first tagged complexes pool is mixed thoroughly prior to step iv) to ensure separation of molecules from different complexes.

In some embodiments, after the distributing of step i) or iv) and before the tagging of step ii) and/or v) the method can further comprise adding an adaptor and/or performing modifications of the nucleic acid and/or protein complexes such as tailing and in particular dA tailing. Additional modifications comprise 5'-phosphorylation, DNA end-repair, 3C spacers to prevent ligation on a particular strand and additional modifications identifiable by a skilled person upon reading of the present disclosure In some embodiments, the method can comprise adding an adaptor and/or reagent to perform additional modifications to the initial complex suspension and/or the additional complex suspension of steps i) or iv). In particular, in some of these embodiments the adaptor can be a ligation adaptor molecule configured to modify at least one end of each of the DNA, RNA, and/or protein molecules in the respective suspension and capable of ligating to the unique initial and/or additional nucleotide tag.

Following the tagging of step ii) and v) the method comprises the pooling steps iii) and vi). As used herein, "pooling" refers to collecting and mixing together a plurality of components. For example, pooling of suspensions includes mixing multiple suspensions into one larger, pooled suspension.

In embodiments of split and pool barcoding, the pooling, distributing (sorting), and tagging is performed until the number of unique tags attached to each nucleic acid and/or protein complex forms a barcode specific for that nucleic acid and/or protein complex, thus providing a complex barcoded with a cell-specific or organelle-specific barcode and with a complex-specific barcode as will be understood by a skilled person.

In some embodiments, the pooling, distributing (sorting), and tagging are repeated for at least three times.

In some embodiments, after the last nucleotide tag forming the complex-specific barcode is added, the double-barcoded pool of nucleic acid and/or protein complexes can be redistributed again into a plurality of double-barcoded pool suspensions for the addition of a terminal nucleotide tag. A terminal tag can provide an additional unique sequence and may also provide a primer site for amplification. In those embodiments the method further comprises
viii) distributing the double-barcoded pool of nucleic acid and/or protein complexes into a plurality of double-barcoded suspensions;
ix) adding a unique terminal nucleotide tag to each of the plurality of double-barcoded suspensions to perform terminal tagging of the double-barcoded nucleic acid and/or protein complexes in the respective double-barcoded suspension and thereby form a plurality of terminally tagged double-barcoded suspensions; and
x) pooling the plurality of terminally tagged double-barcoded suspensions to form a terminally tagged double-barcoded pool.

A detailed description of split-and-pool barcoding is provided in the U.S. patent application Ser. No. 15/466,861, entitled "Methods for identifying Macomolecule Interaction" filed on Mar. 22, 2017, the entire disclosure of which is herein incorporated by reference in its entirety. In particular, the Split-Pool Recognition of Interactions by Tag Extension (SPRITE), method described in the U.S. patent application Ser. No. 15/466,861, can be performed to add a complex-specific barcode to nucleic acid and/or protein complexes barcoded with a single-cell specific barcode (cell specific or organelle specific) in accordance with the present disclosure.

In some embodiments herein described in-cell or in-organelle nucleic acid and/or protein complexes comprise complexes naturally presenting in the cell and/or in the organelle before the permeabilizing, in view of the state of the cell and naturally occurring reactions under the related culture conditions.

In some embodiments the in-cell or in-organelle nucleic acid and/or protein complexes comprise complexes provided in the cell or in the organelle following crosslinking of the cell and/or the organelle.

The term "crosslink" as used herein refers to the formation of a covalent linkage between two molecules such as DNA, RNA and/or proteins in the cell and/or the organelle. Crosslinking can be performed by crosslinkers which comprise any agent that can react with one or more nucleic acid and/or protein to provide a nucleic acid and/or protein complex in the sense of the disclosure where the molecules bound one to another via covalent linkage of corresponding functional groups. Typically, crosslinkers in the sense of the disclosure can react with at least one of the functional groups of a nucleic acid or protein to provide an activated nucleic acid or protein presenting a free radical on the at least one functional group. Reaction of one or more activated nucleic acid or protein with another nucleic acid or protein typically starts a chain of reaction resulting in formation of a nucleic acid and/or protein complex in the sense of the disclosure. Exemplary crosslinkers comprise photons (e.g. provided by UV light or other light source) and chemical species (e.g. enzymes photoinitiators and thermal initiators) that can provide free radicals under appropriate conditions)

Accordingly, in some embodiments of the methods to perform single-cell marking of a nucleic acid and/or protein in a sample, the method further comprises: crosslinking the cell to provide a crosslinked cell comprising a crosslinked nucleic acid and/or protein material of the organelle, before permeabilizing the cell.

In some of those embodiments, crosslinking can be performed by contacting a cell from the plurality of cells of the sample, or an organelle from the cell with a crosslinker targeting functional groups of the protein to form molecular complex informative of the in-cell protein-nucleic acid interactions.

In some of these embodiments, protein crosslinkers can target functional groups such as primary amines (—NH$_2$), carboxyls (—COOH), thiols (—SH), and carbonyls (—CHO).

In some of these embodiments, protein crosslinkers contain aldehyde functional groups, including glutaraldehyde [17].

In some of these embodiments, protein crosslinkers contain imidoester functional groups, which include dimethyl adipimidate (DMA), dimethyl pimelimidate (DMP), dimethyl suberimidate (DMS), dimethyl 3,3'-dithiobispropionimidate (DTBP), and additional crosslinker containing imidoester functional groups identifiable by a skilled person [18].

In some of these embodiments, protein crosslinkers contain N-hydroxysuccinimide (NHS) ester functional groups, which include disuccinimidyl suberate (DSS), dithiobis(succinimidyl propionate) (DSP), ethylene glycol bis(succinimidyl succinate) (EGS), and tris-(succinimidyl)aminotriacetate (TSAT) [19]. In particular, a representative example of this protein crosslinkers is disuccinimidyl glutarate (DSG), which is a 7.7 Å, homobifunctional crosslinker capable of capturing long-range protein-protein interactions by covalent interactions between its ester group (specifically) and primary amines present in all proteins. DSG crosslinking is typically used for capturing/preserving configurations with higher-order structure. DSG is water insoluble, but can be dissolved in polar organic solvents including DMF and DMSO. In some embodiments, DSG can be provided at various concentration, with the most common final concentration of DSG in a given cell solution is between 0.5-5 mM typically 2 mM. Crosslinking with DSG is typically performed at room temperature for 45 minutes, but DSG can be used for as long as an hour [20].

In some embodiments, wherein the method comprises a crosslinking, the crosslinking can be performed by contacting a cell from the plurality of cell or an organelle from the cell with a crosslinker comprising chemical species targeting a strong nucleophile in the protein (such as an ε-amine on a lysine amino acid) to form an intermediate Schiff base. The Schiff base is then able to crosslink with another nucleophile, which can come from an amino group on a DNA or RNA base [21] [22].

In some of these embodiments, the crosslinker can comprise paraformaldehyde, formaldehyde, formalin. An exemplary example of this class of crosslinkers is formaldehyde, which crosslinks at close proximity, linking groups that are about 2 Å apart. At the single-cell level, formaldehyde is generally used at a final concentration of 1-2%, but can be extended as high as 4% or below 1% for other applications [21]. Reactions with formaldehyde can be performed within 30 minutes for chromatin studies, with most reactions allowing for 10-15 minutes of formaldehyde exposure. Formaldehyde's rate of reverse crosslinking is demonstrated as an exponential function with respect to temperature, so crosslinked pellets are usually kept cold or at RT afterwards [22].

In some embodiments, wherein the method comprises a crosslinking, the crosslinking can be performed by contacting a cell from the plurality of cell or an organelle from the cell with a crosslinker targeting functional groups of a nucleic acid to form molecular complex in the sense of the disclosure which are informative of the in-cell-nucleic acid/nucleic acid and/or nucleic acid/protein interactions.

In some of those embodiments, the crosslinker can target functional groups within nucleotide bases in DNA and/or RNA, including uracil, adenine, guanine, cytosine, and thymine.

In some embodiments, DNA crosslinking agents comprise exogenous crosslinking agents containing both natural and synthetic chemical compounds, such as nitrogen mustards, cisplatin, chloroethyl niroso urea (CENU), psoralens, mitomycin C, etc. [23-25].

In some embodiments, DNA crosslinking agents comprise endogenous crosslinking agents that derive naturally from cellular and biochemical pathways, such as nitrous acid, bifunctional aldehydes, and reactive oxygen species [23, 26-28].

In some embodiments, crosslinking can be performed by crosslinkers forming complexes without requiring concurrent use of UV light, to form RNA-RN. An example of this type of crosslinkers is 4' aminomethyl trioxsalen [29].

In some embodiments, crosslinkers forming complexes requiring concurrent use of UV light are used for crosslinking to form RNA-RNA linkers (classified as photoagents), such as azidophenacyl derivatives and thionucleotide photoagents (such as 6-thioguanosine and 4-thiouridine) and additional crosslinkers identifiable by a skilled person [30].

In some embodiments, the crosslinking of the isolated cell can be terminated by addition of quenchers such as glycine which can inhibit further reaction of the crosslinker and terminate the crosslinking of the isolated cell. In particular, for the crosslinkers that target primary amine groups on nucleic acids and proteins (e.g. formaldhehyde, DSG), small molecule quenchers containing primary amine groups can be added in excess relative to the crosslinker. The two most common quenchers comprise tris and glycine, although others, although other small molecules containing primary amines can be used.

In embodiments wherein crosslinking is performed, crosslinking the cell provides a crosslinked cell comprising a crosslinked nucleic acid and/or protein material of the cell or the organelle thereof.

In some embodiments, the crosslinked nucleic acids and/or proteins material comprises crosslinked nucleic acids and/or proteins complexes naturally presenting in a cell and/or an organelle thereof in a stable conformation, the complexes further crosslinked to comprise covalent linkages.

In embodiments herein described wherein the method comprises a crosslinking, the crosslinking, the methods can further comprise in-cell or in-organelle fragmenting crosslinked nucleic acids and/or proteins material to generate fragmented crosslinked nucleic acids and/or proteins material and therefore cross-linked molecular complexes such as crosslinked DNA, RNA, and/or proteins.

The term "fragmenting" as used herein refer chemically breaking or fragmenting macromolcular complexes into small or separate parts. For example, fragmenting chromosomal DNA can be carried out using or chemical reactions such as enzymatic treatment into assemblies of small, separated DNA, RNA with or without proteins. The term "fragmenting" as used herein does not comprise mechanical fragmentation to the extent that the related application to the cell or organelle result in lysis of the cell or the organelle.

In particular, in embodiments herein described the fragmenting is an in-cell or an in-organelle fragmenting wherein crosslinked nucleic acids and/or proteins material are fragmented by enzymes such as restriction enzymes into crosslinked nucleic acid and/or protein complexes in reduced sizes capable of being tagged or barcoded.

In some embodiments, the in-cell fragmenting can be performed by chemically fragmenting the in cell nucleic acid and/or protein complexes e.g. by restriction enzyme treatment, DNase treatment, sonication, CRISPER/CAS9 and/or additional treatments identifiable by a skilled person.

In some of those embodiments, the in-cell or in nucleus fragmenting can be performed by contacting the isolated cell or the isolated nucleus with fragmentation enzymes or DNA modification enzymes following permeabilization of the isolated fixated cell. Exemplary restriction enzymes suitable for fragmentation comprise type I, type II, type III, type IV [31]. Exemplary restriction enzymes derived from type II restriction enzymes, comprise HpyCH4V, MboII, HindIII, EcoRI [32].

In some embodiments, in cell or in-organelle fragmenting cross-linked chromatin is performed using restriction enzyme treatment (see Examples 4 and 5). Proper restriction enzyme or mixture of enzymes are selected to fragment the chromatin into about 300-700 bp fragments. 4-base cutter would be preferable because given a random genome the enzyme would cut the DNA on average every $4^4$ or 256 bases. Suitable enzyme includes HpyCH4V enzyme, which cuts on the recognition sequence TGCA. Other suitable enzymes would be identifiable to a person skilled in the art.

In some embodiments, in-cell or in organelle chemically fragmenting the nucleic acid and/or protein complexes can be performed with an enzyme selected to obtain a set size of restriction enzyme digests. In those embodiments, the enzyme is typically selected depending on what resolution of the contacts are desired. 6-bp cutters (e.g. NcoI, NehI, PmII, SpeI) are generally used to establish long-range DNA contacts, such as the interaction between promoters-enhancers. 4-bp cutters (e.g. HpyCH4V, MboI, NedII, DpnII) are generally used to establish short-range DNA contacts.

In some embodiments, where the method is performed in connection with applications such as in situ DNase Hi-C, DNase is the primary choice of fragmentase to fragment DNA in regions of open chromatin, usually sites containing gene promoters, enhancers, silencers—essentially pieces necessary for gene regulation. DNase is generally used as low as 1.5-2 U [33] for digestion, but can be as high as 40-60 U [34]. Depending on the fragment size, incubation with DNase can range between 4-10 min [33], with incubations happening at 37° C.

In some embodiments, restriction enzymes are prepared in a buffer condition for optimal performance. These buffer conditions are not stressful enough to lyse the cell/nucleus fully as will be understood by a person skilled in the art. In some embodiments, restriction enzymes are about 400-650 amino acids in length, and with an average amino acid size of 3.5 Å. The largest size the restriction enzyme would be is 227.5 nm. In some embodiments, the fragmented nucleic acids and/or protein complexes have a size at least 227.5 nm to ensure the fragmented complexes are not over fragmented from digestion.

In some embodiments of the methods herein described, the method further comprises isolating the cell from the sample before permeabilizing a cell from the plurality of cells or an organelle thereof, and/or before crosslinking the cell to provide a crosslinked cell comprising a crosslinked nucleic acid and/or protein material of the organelle.

"Isolating" as used in accordance with the present disclosure indicates a process of separating a first referenced item from a second reference item. For example, isolating a cell from a sample indicates the process of separation of individual living cells from a sample such as a tissue or cell lines where cells are covalently linked one to another typically within an extracellular matrix. In those instances, enzymes can be used to digest proteins that bind cells to be isolated together within the extracellular matrix. After the matrix proteins have been digested, cells remain loosely bound together but can be gently separated e.g. mechanically.

In some embodiments of methods herein described, isolating a cell from a sample can be performed by disrupting covalent linkages of (in particular protein bridges linking) cells to one another, to an extracellular matrix and/or to a surface in the sample prior to passaging or harvesting the cells. In some of those embodiments the disrupting covalent linkage of the cell can be performed by mechanical and/or chemical approaches. In particular, in some of these embodiments, disruption of covalent linkage of the cell can be performed by applying mechanical stress to remove cells from their surfaces, such as a cell scraper). In addition or in the alternative, disruption of covalent linkage of the cell can be performed chemically by proteases target specific peptide bonds to help detach cells from surfaces, such as tryspin, collagenase, elastase, papain, and additional proteases identifiable by a skilled person. to reduce number of cell contacts prior to crosslinking [35].

In some embodiments, isolating a cell from a sample can be performed by triturating the sample e.g. using blunt-end or hypodermic needles to prevent cells from sticking together.

In some embodiments, methods of the disclosure further comprise isolating an organelle from the cell. In those instances, lytic reagents can be used to lyse the cell with suitable lytic reagents.

In some embodiments, isolating the organelle can be performed, by, lysing the isolated cell by viral, chemical, enzymatic, and/or osmotic mechanisms that compromise the integrity of the cell, to form a cell lysate.

In some embodiments, isolating the organelle can be performed by contacting a cell lysis agent to crosslinked cells and incubating the resulting mixture for a time period under a condition to ensure lysis of the crosslinked cell.

In some embodiments, suitable lysis agent to perform isolating the organelle herein described includes a detergent.

In embodiments herein described, detergents used to lyse an isolated cell can be denaturing or non-denaturing such as Nonidet P-40 (octylphenoxypolyethoxyethanol) or CHAPS as will be understood by a person skilled in the art.

In some embodiments, the cell lysis agent can be provided in a lysis buffer that typically contains salts such as Tris-HCL or EDTA to regulate the acidity and osmolarity of the lysate (see Example 3).

In some embodiments, lysing the cell further comprises additional physical processing of a mixture comprising the cell to achieve lysis of the cells. Physical processing can include high-shear conditions such as those in douncing or passing through a high gauge needle.

In some embodiments of isolating nuclei, following cell lysis nuclei aggregates are formed. In those embodiments the nuclei aggregates can be triturated using blunt-end or hypodermic needles to break larger aggregates of nuclei into smaller or single aggregates, and/or be passed through a filter to remove larger aggregates of nuclei. In embodiments where the organelle is a mitochondrion, a smaller gauge needle (e.g. >30 g needles) will be used.

In embodiments herein described where the method comprises isolating the organelle, the isolating can be performed prior to or following the crosslinking the cell and/or the organelle.

In some embodiments, in-cell or in-organelle barcoding the nucleic acid and/or protein complexes can be performed on isolated single-cell or single-organelle. In those embodiments the cells or the organelles thereof are separated into a number of individual cells or individual organelles such that each cell or organelle thereof can be individually tagged with a unique barcode. In these embodiments, only one round of tagging is necessary to provide a barcode formed by one single unique tag to each cell or organelle and the molecular complexes of that cell or organelle.

In some of these embodiments, barcoding nucleic acid and/or protein complexes can be performed on isolated single-cell or single-organelle can be performed in a microfluidic device. In these embodiments, in cell or in-organelle barcoding can be performed by isolating the cells or the organelles thereof into a plurality of single cells or single organelles and barcoding each isolated single-cell or single organelle within a microfluidic device in which a barcode and reagents for the related attachment to a nucleic acid and/or a protein of the nucleic acid and/or protein complex of the single cell or organelle are added to each of the isolated single cell or single organelle.

In some embodiments, the barcoding can be performed on a plurality of isolated cells or organelles by split and pool tagging methods herein described.

In some embodiments, the in cell or in organelle barcoding of nucleic acid and/or protein complexes of single-cell or organelle, or of a plurality of isolated cells or organelles, can be performed in microfluidic devices.

An exemplary microfluidic technology suited for complex manipulations and multiple steps of methods herein described is the SlipChip technology [36-48]. SlipChip microfluidic devices are ideal for complex procedures because they can be "programmed" to include numerous fluid handling steps, and have previously been validated for isolating single cells. [39, 40].

In some embodiments, a SlipChip device suitable for performing methods herein described are described in U.S. application Ser. No. 16/141,707, entitled "Device for Additive Delivery of Reagents and Related Methods and Systems" filed on Sep. 25, 2018, and incorporated herein by reference in its entirety.

In particular, in those embodiments, a microfluidic device is described for isolating cells or organelles thereof into a plurality of single cells or single organelles for in-cell or in-organelle barcoding. In those embodiments device typically comprises: a first plate comprising a first surface; and a second plate with a second surface, the first surface in contact with the second surface; the first plate having on the first surface a loading channel and pooling wells; the second plate having on the second surface loading wells; wherein the loading wells are configured to be aligned in a one-to-one correspondence with the pooling wells, and the loading wells have a smaller volume than the pooling wells.

The device for isolating cells or organelles thereof into a plurality of single cells or single organelles for in-cell or in-organelle barcoding herein described can also comprise: surface energy traps (i.e. deeper portions) in the pooling wells; the loading wells having a greater depth than the loading channel; and/or the channel-loaded loading wells each having a side opposite a direction from the loading channel to the pooling wells the direction perpendicular to the loading channel, the side comprising two walls at equal angles from a bisector of the each channel-loaded loading wells parallel to the direction from the loading channel to the pooling wells, the equal angles each being less than 90 degrees.

FIG. 31 shows an example device for isolating cells or organelles thereof into a plurality of single cells or single organelles for in-cell or in-organelle barcoding (not to scale—the channels and wells would be much smaller). In the illustration of FIG. 31 including two plates (115, 120), shown in cross-sectional side view (105) and top down view (110). To aid understanding of the correspondence between the views, the features of the top plate (115) are shown with solid lines, and the features of the bottom plate (120) are shown in dashed lines.

FIG. 31 shows the exemplary device for isolating cells or organelles thereof into a plurality of single cells or single organelles for in-cell or in-organelle barcoding with plates (115, 120) positioned for loading of the channel-loaded loading wells (116). The loading wells (116) are aligned with the loading channel (121) of the opposite plate. This allows the loading of material from the loading channel (121) to the loading wells (116). Pooling wells (122) are positioned in-line longitudinally with corresponding loading wells (116), so that when the plates (115, 120) are slid together, the loading wells (116) will be over corresponding pooling wells (122) (See FIG. 2). An eluting channel (117) is in the plate (115) that is opposite the pooling wells (122).

FIG. 32 shows the example device of FIG. 31, where the plates (115, 120) have been slid into a different position, as shown in the new cross-sectional side view (205) and the new top view (210). In the different position, the loading wells (116) are over the corresponding pooling wells (122) allowing the contents of the loading wells (116) to drop into the pooling wells (122) in an isolated manner. The transfer from the loading wells (116) to the pooling wells (122) can be due to capillary action, given the relative size difference between the smaller loading wells (116) and the larger pooling wells (122).

FIGS. 33A-33F show an example device for isolating cells or organelles thereof into a plurality of single cells or single organelles for in-cell or in-organelle barcoding (not to scale, for ease of viewing) used for attaching adapters to DNA in individual nuclei, such that the nuclei remain isolated from each-other. In these figures, channels are shown in solid lines while wells are shown in dotted lines, regardless of plate. In FIG. 33A, the loading wells (311) are aligned over the loading channel (321). Note that "over" and "under" (or "top" and "bottom") are used with reference to the drawings, and the actual orientation will typically not matter as the driving forces are microfluidic and typically will not depend on the direction of gravity.

A solution containing individual nuclei is usually injected into the loading channel such that each loading well only has one nucleus. This can be done by Poisson distribution, or any other loading system. There is, of course, a trade-off of probability of having wells with multiple nuclei vs. number of wells effectively loaded. Once loaded, the device plates are slid to FIG. 33B, where the loading wells (311) are positioned over the pooling wells (322), with capillary action dropping the nuclei into the pooling wells.

The device is then slid to a new position, as shown in FIG. 33C, where the adapter wells (312) are positioned over the pooling wells (322). In this case, instead of being loaded via a channel, the adapter wells (312) can be pre-spotted with adapters (optionally uniquely tagged adapters) which are then rehydrated by mixture with the contents of the pooling wells (322). Optionally, the use of adapter wells can be bypassed by pre-spotting the adapters directly into the pooling wells (322) instead. The adapters and the nuclei can be combined in the pooling wells (322) by mixing. Mixing can be performed by repeatedly inverting the device, or by magnetic mixing if the adapters are attached to magnetic beads, or by any standard microfluidic mixing technique.

Once the adapters have been sufficiently mixed with the nuclei, the device is slid back to loading position, as shown in FIG. 33D. The loading wells (311) and loading channel (321) are cleaned, then the loading wells (311) are filled with a ligation mix (331). The ligation mix can be, for example, T4 ligase, Blunt/TA Ligase Master Mix, Instant Sicky-End Ligase Master Mix, RNA-ligase, etc.

The device is slid again, as shown in FIG. 33E, such that the loading wells (311) are again aligned with the pooling wells (322), thereby allowing mixture of the ligation mix and the nuclei-adapter solution. Ligation proceeds as long as need be (e.g. 1, 2, 3, 4, 5, 6, 8, 10, 12, 16, or 20 hours).

The device can be inverted at regular intervals to prevent settling. Once the ligation is complete, the device is slid to a new position, as shown in FIG. 33F, that aligns the pooling wells (322) with the elution channel (315). The elution channel (315) is flushed, thereby eluting the nuclei (now with attached adapters) out of the device, for further processing.

Figure 2:
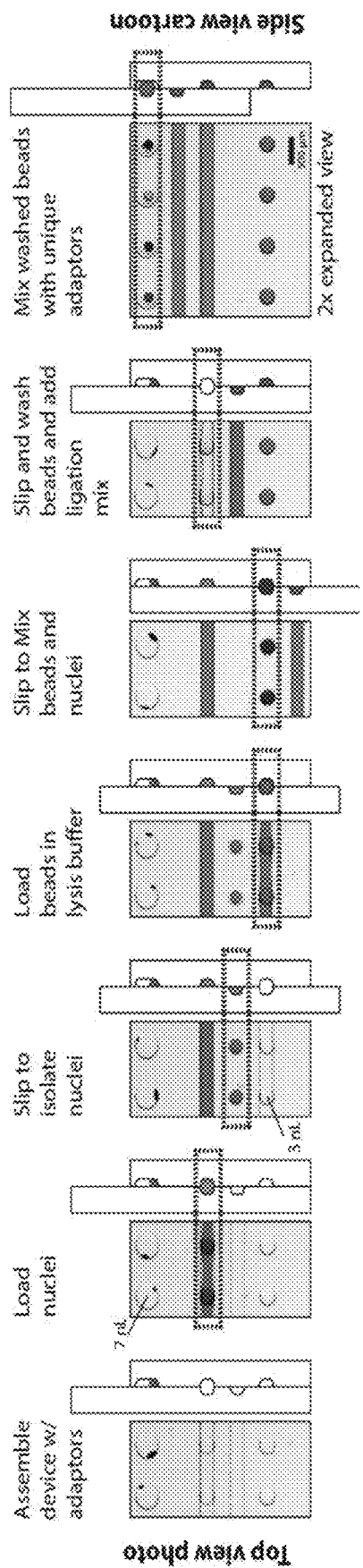
FIG. 2 shows a schematic illustrating an exemplary SlipChip device suitable for performing single cell nucleus specific barcoding. The device shown in the schematic illustration of FIG. 2, has four different programmed positions in which all required procedures can be completed. Unique adapters are spotted deterministically on the device prior to assembly.
Figure 3:
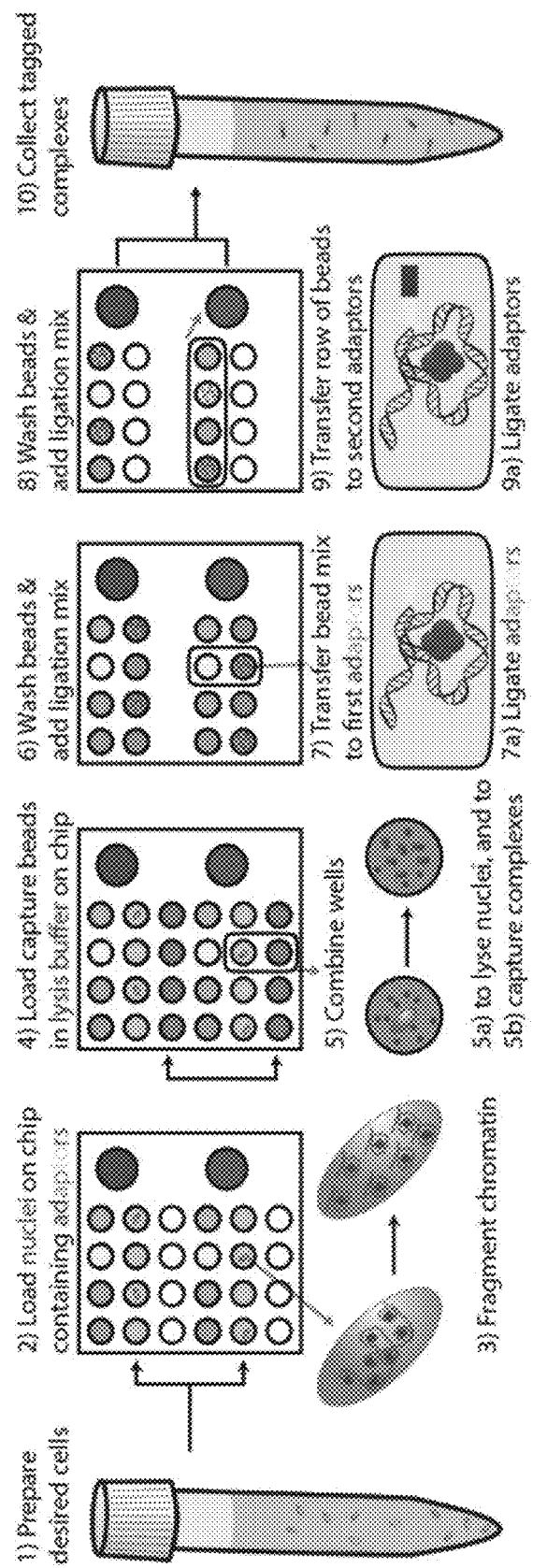
FIG. 3 illustrates a schematic of steps of methods herein described performed on a microfluidic device configured to provide single cell labeled molecular complexes labeled with nucleus specific barcode which can be used for split and pool mapping of individual cells.

An additional exemplary device for additive delivery configured to perform methods herein described wherein the barcoding is performed on isolate single-cells or isolated single organelle, is shown in FIG. 2. The exemplary device of FIG. 2 incorporates four different positions: two are used for loading; two are used for mixing loaded solution. In the exemplary device of FIG. 2, the user is able to visually confirm and image the loading of single nuclei, and relate sequenced results back to a specific device and compartment. The ability to relate sequenced results back to a specific well on a specific device is due to the ability to robustly and deterministically spot a precise amount of adapters onto a SlipChip device prior to assembly. This configuration is therefore advantageous compared with alternative single-cell microfluidic techniques [49-54]. This configuration can also be beneficial when validating a sequencing dataset as cell loading is Poisson based, and results can be confirmed to come from a single cell as opposed to multiple.

In some embodiments, microfluidic devices can be used to perform methods herein described wherein the barcoding is performed by split and pool barcoding. In designing a microfluidic device to prepare cells for split-and-pool barcoding with magnetic beads, a magnetic setup was implemented along the channels of the device to reliably handle magnetic beads. One geometry for magnets would be to have a point source field directly beneath each microfluidic well [55]. With this geometry, magnetics beads would have a force applied drawing them toward the center of the well against fluid flow. Another magnetic setup suitable to achieve this effect can have a line source magnetic field transverse to the flow in the system directly under the wells containing magnetic beads. A geometry with a wide tolerance to misalignment would be to have line sources along the channels of the device. In this geometry, there would be no direct force keeping the beads from flowing through the channel, however, as long as the magnetic force can overcome the force induced by flow the beads would remain in the wells (depressions) on the device.

In those embodiments, the flow in the microfluidic device is controlled to not overpower the magnetic force on the beads. Flow control in SlipChip microfluidic devices can be achieved using a constant pressure source. Constant pressure sources are easy and inexpensive to implement with a simple pipettor, and are ideal for SlipChip devices because the pressure used to drive the flow can be precisely controlled to avoid leakage [38]. For the split-and-pool barcoding method, a constant flow rate source is needed and this can be implemented with a syringe pump. To interface the syringe pump with the microfluidic device, a piece of Teflon tubing can be used to connect the pump's syringe to a 3D-printed gasket. The gasket was designed to have an interference fit for the tubing and is successfully able to withstand flow rates of up to 10 mL/hr with no leakage. The gasket is printed from TangoPlus material on a Connex 3D printer and attached to the SlipChip using UV curable optical adhesive. When combining this pumping strategy with 2"×0.25"×0.1" neodymium magnets aligned to the SlipChip channels using a custom 3d printed holder we were able to maintain the position of the magnetic beads in the wells of the device at flow rates of up to 1 mL/hr which is sufficient for all processing steps.

In those embodiments, in addition to proper loading of the magnetic beads and flow over the beads in SlipChip, the device was configured to have the beads were sufficiently suspended in solution during the enzymatic steps. One option for dispersing the beads on the device would be through magnetic mixing [56]. A alternative option can be that of rotating the microfluidic device at a frequency that would keep the majority of beads in solution based on settling times. The settling time of magnetic beads on device can be estimated based on terminal velocity calculations using Eq. 1 where V is the terminal velocity of the beads, $\rho_p$ is the bead density, $\rho_f$ is the fluid density, $\mu$ is the dynamic viscosity, g is acceleration due to gravity, and R is the hydrodynamic radius of the beads.

$$V = \frac{2}{9} \frac{(\rho_p - \rho_f)}{\mu} g R^2 \qquad \text{(Eq. 1)}$$

Figure 14:
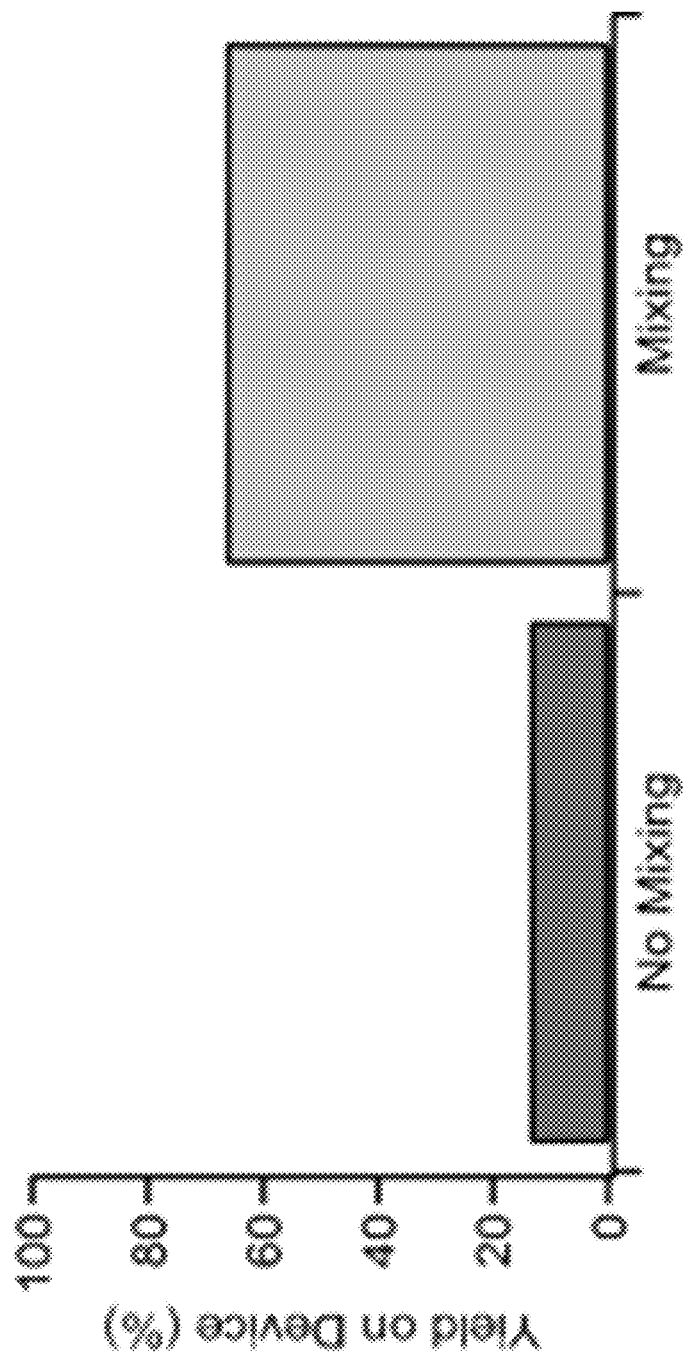
FIG. 14 shows in a plot the percentage difference in yield when ligation is performed on-device versus off-device, separated by whether or not mixing was performed on-device. In all experiments, the number of beads was controlled. The yield for on-device ligation without mixing was 14% as compared to off-device ligation. The yield for on-device ligation with mixing was 66% as compared to off-device ligation. Ligation was measured by qPCR.

Based on this formula, and using parameters of 2 g/mL bead density, 1 g/mL fluid density, 0.001 kg/(m*s) dynamic viscosity, and a bead radius of 50 μm, a terminal velocity of ~0.5 μm/sec was calculated. Because acceleration to terminal velocity is nearly instantaneous and the total depth of the chamber containing the beads is 100 μm, we expect complete settling of the beads in ~3 min. This mixing method was tested by taking controlled amounts of beads that were complexed to nuclear components that were digested, repaired, and dA-tailed and performing ligation of adapters on and off device. When ligation was performed on device without keeping the beads dispersed in solution, the difference in Cq was 2.9 which corresponds to a relative yield of ~14%. When maintaining dispersion of beads on device using a custom rotisserie, the difference in Cq was only 0.6 which corresponds to a yield of ~66% (FIG. 14). This shows that we can keep beads non-motile under changing conditions when required, and that we can disperse those beads when new conditions have been established to significantly increase yield.

In some embodiments herein described, the barcoded nucleic acid and/or protein complexes can be subjected to further analysis.

For example, in some embodiments the method can further comprise sequencing each barcode of the in-cell or in-organelle barcoded nucleic acid and/or protein complexes; and detecting the nucleic acid and/or protein molecules tagged with a same barcode in e barcoded complex pool or the terminally tagged barcoded pool.

In some embodiments, the method can further comprise amplifying a barcode of the of the in-cell or in-organelle barcoded nucleic acid and/or protein complexes e.g. to make a library and then sequence the amplified tags.

In embodiments wherein the barcoded nucleic acid and/or protein complexes comprise nucleic acids, sequencing can be performed by next-generation DNA sequencing techniques as will be understood by a skilled person. In some embodiments, the sequencing is performed by paired-end sequencing. Paired-end sequencing allows one to sequence both ends of a fragment and generate high-quality alignable sequence data.

After paired-end sequencing, interactions can be identified by aligning the genetic sequences from one end of the pair to barcodes on the other end. Once this relationship is established, all aligned sequences resulting from identical barcodes can be grouped together as a higher-order interacting complex.

Additional analysis of the in-cell or in-organelle barcoded nucleic acid and/or protein complexes can comprise quantitative, non-sequencing DNA analysis (e.g. using real-time PCR, droplet-digital PCR) and additional analysis identifiable by a skilled person upon reading of the present disclosure Methods herein described can be performed according to multiple variants in accordance with the disclosure as will be understood by a skilled person.

According to the present disclosure in some embodiments a method to perform single-cell marking of a nucleic acid and/or protein in a sample comprising a plurality of cells, can be performed by:
permeabilizing a cell from the plurality of cells, to provide a permeabilized cell;
in-cell barcoding nucleic acid and/or protein complexes of the permeabilized cell, to provide in-cell single-cell marked nucleic acid and/or protein complexes comprising a single-cell specific marker.

In some embodiments a method to perform single-cell marking of a nucleic acid and/or protein in a sample comprising a plurality of cells, can be performed by: isolating the cell from the plurality of cell;
permeabilizing the isolated cell, to provide a permeabilized cell;
in-cell barcoding nucleic acid and/or protein complexes of the permeabilized cell, to provide in-cell single-cell marked nucleic acid and/or protein complexes comprising a single-cell specific marker.

In some embodiments a method to perform single-cell marking of a nucleic acid and/or protein in a sample comprising a plurality of cells, can be performed by:
crosslinking the cell to provide a crosslinked cell comprising crosslinked nucleic acid and/or protein material of the cell
permeabilizing the crosslinked cell, to provide a permeabilized cell;
in-cell barcoding nucleic acid and/or protein complexes of the permeabilized cell, to provide in-cell single-cell marked nucleic acid and/or protein complexes comprising a single-cell specific marker.

In some embodiments a method to perform single-cell marking of a nucleic acid and/or protein in a sample comprising a plurality of cells, can be performed by:
isolating the cell from the plurality of cell
crosslinking the isolated cell to provide a crosslinked cell comprising crosslinked nucleic acid and/or protein material of the cell and/or crosslinked nucleic acid and/or protein complexes of the cell;
permeabilizing the crosslinked cell, to provide a permeabilized cell;
in-cell barcoding nucleic acid and/or protein complexes of the permeabilized cell, to provide in-cell single-cell marked nucleic acid and/or protein complexes comprising a single-cell specific marker.

In some embodiments a method to perform single-cell marking of a nucleic acid and/or protein in a sample comprising a plurality of cells, can be performed by:
crosslinking the cell to provide a crosslinked cell comprising crosslinked nucleic acid and/or protein material of the cell and/or crosslinked nucleic acid and/or protein complexes;
permeabilizing the crosslinked cell, to provide a permeabilized cell;
in-cell fragmenting the crosslinked nucleic acid and/or protein material of the permeabilized cell, to provide in-cell nucleic acid complexes comprising crosslinked nucleic acid and/or protein complexes of the cell,
in-cell barcoding crosslinked nucleic acid and/or protein complexes of the permeabilized cell, to provide in-cell single-cell marked nucleic acid and/or protein complexes comprising a single-cell specific marker.

In some embodiments a method to perform single-cell marking of a nucleic acid and/or protein in a sample comprising a plurality of cells, can be performed by:
isolating the cell from the sample;
crosslinking the isolated to provide a crosslinked cell comprising crosslinked nucleic acid and/or protein material of the cell and/or crosslinked nucleic acid and/or protein complexes of the cell; permeabilizing the crosslinked cell, to provide a permeabilized cell;
in-cell fragmenting the crosslinked nucleic acid and/or protein material of the permeabilized cell, to provide in-cell nucleic acid complexes comprising crosslinked nucleic acid and/or protein complexes, in-cell barcoding nucleic acid and/or protein complexes of the permeabilized cell, to provide in-cell single-cell marked nucleic acid and/or protein complexes comprising a single-cell specific marker.

In some of these embodiments, the cell is a single cell of the plurality of cells and the in-cell barcoding is performed by attaching a barcode comprising a single unique tag to the nuclei acid and/or protein complexes of the permeabilized cell.

In some of these embodiments, the cell is a plurality of cells and the in-cell barcoding is performed by in-cell split and pool barcoding the nucleic acid and/or protein complexes of each cell.

In some of these embodiments, the method comprises after the in-cell barcoding: lysing the cell to isolate single-cell marked nucleic acid and/or protein complexes comprising a single-cell cell specific tag for the cell.

In some embodiments a method to perform single-cell marking of a nucleic acid and/or protein in a sample comprising a plurality of cells, can be performed by:
permeabilizing an organelle of a cell from the plurality of cells, to provide a permeabilized organelle;
in-organelle barcoding nucleic acid and/or protein complexes of the permeabilized cell, to provide in-organelle single-cell marked nucleic acid and/or protein complexes comprising a single-cell specific marker.

In some embodiments a method to perform single-cell marking of a nucleic acid and/or protein in a sample comprising a plurality of cells, can be performed by:
isolating the organelle of the cell from the plurality of cell.
permeabilizing the isolated organelle, to provide a permeabilized organelle;
in-organelle barcoding nucleic acid and/or protein complexes of the permeabilized cell, to provide in-organelle single-cell marked nucleic acid and/or protein complexes comprising a single-cell specific marker.

In some embodiments a method to perform single-cell marking of a nucleic acid and/or protein in a sample comprising a plurality of cells, can be performed by:
crosslinking the organelle to provide a crosslinked organelle comprising crosslinked nucleic acid and/or protein material of the organelle;
permeabilizing the crosslinked organelle, to provide a permeabilized organelle;
in-organelle barcoding nucleic acid and/or protein complexes of the permeabilized organelle, to provide in-organelle single-cell marked nucleic acid and/or protein complexes comprising a single-cell specific marker.

In some embodiments a method to perform single-cell marking of a nucleic acid and/or protein in a sample comprising a plurality of cells, can be performed by:
isolating the organelle of the cell from the plurality of cell.
crosslinking the isolated organelle to provide a crosslinked organelle comprising crosslinked nucleic acid and/or protein material of the organelle and/or crosslinked nucleic acid and/or protein complexes of the organelle;
permeabilizing the crosslinked organelle, to provide a permeabilized organelle;
in-organelle barcoding nucleic acid and/or protein complexes of the permeabilized organelle, to provide in-organelle single-cell marked nucleic acid and/or protein complexes comprising a single-cell specific marker.

In some embodiments a method to perform single-cell marking of a nucleic acid and/or protein in a sample comprising a plurality of cells, can be performed by:
crosslinking the organelle to provide a crosslinked organelle comprising crosslinked nucleic acid and/or protein material of the organelle and/or crosslinked nucleic acid and/or protein complexes of the organelle;
permeabilizing the crosslinked organelle, to provide a permeabilized organelle;
in-organelle fragmenting the crosslinked nucleic acid and/or protein material of the permeabilized organelle, to provide in cell nucleic acid complexes comprising crosslinked nucleic acid and/or protein complexes of the organelle,
in-organelle barcoding nucleic acid and/or protein complexes of the permeabilized cell, to provide in-organelle single-cell marked nucleic acid and/or protein complexes comprising a single-cell specific marker.

In some embodiments a method to perform single-cell marking of a nucleic acid and/or protein in a sample comprising a plurality of cells, can be performed by:
isolating the cell from the sample;
isolating the organelle from the isolated cell:
crosslinking the isolated organelle to provide a crosslinked organelle comprising crosslinked nucleic acid and/or protein material of the organelle
permeabilizing the crosslinked organelle, to provide a permeabilized organelle;
in-cell fragmenting the crosslinked nucleic acid and/or protein material of the permeabilized organelle, to provide in-organelle nucleic acid complexes comprising crosslinked nucleic acid and/or protein complexes;
in-organelle barcoding nucleic acid and/or protein complexes of the permeabilized cell, to provide in-cell single-cell marked nucleic acid and/or protein complexes comprising a single-cell specific marker.

In some of these embodiments, the organelle is a single organelle of a cell of the plurality of cells and the in-organelle barcoding is performed by attaching a barcode comprising a single unique tag to the nuclei acid and/or protein complexes of the permeabilized organelle.

In some of these embodiments, the organelle is a plurality of organelles and the in-organelle barcoding is performed by in-organelle split and pool barcoding the nucleic acid and/or protein complexes of each cell.

In some of these embodiments, the method comprises after the in-organelle barcoding: lysing the organelle to isolate single-cell marked nucleic acid and/or protein complexes comprising a single-cell cell specific tag for the organelle.

In some embodiments herein described, the organelles herein described comprise nuclei. In these embodiments, the methods herein described can be used to study single-cell dynamics and interactions of molecular complexes as well as the three-dimensional structure of the nucleus. The methods herein described can be used to determine protein-DNA interactions, DNA-DNA interactions, RNA-DNA interactions and interactions among other molecular complexes identifiable to a person skilled in the art over a large number of cells. The methods herein described allow the capture of heterogeneity of a cell population at a single-cell level.

In particular, in some embodiments, the methods herein described wherein the organelle is a nucleus can be used to study chromosomal organization and particularly RNA-DNA interactions. For example, large concentrations of messenger RNA are retained by the nucleus and localized to nuclear speckles and other chromatin-associated regions, disruption of RNA transcription has shown nuclear rearrangement without disrupting protein translation, and the long non-coding RNAs have been shown to exploit three-dimensional organization to silence targets.

In some embodiments of methods herein described the organelle comprise mitochondria.

Figure 22:
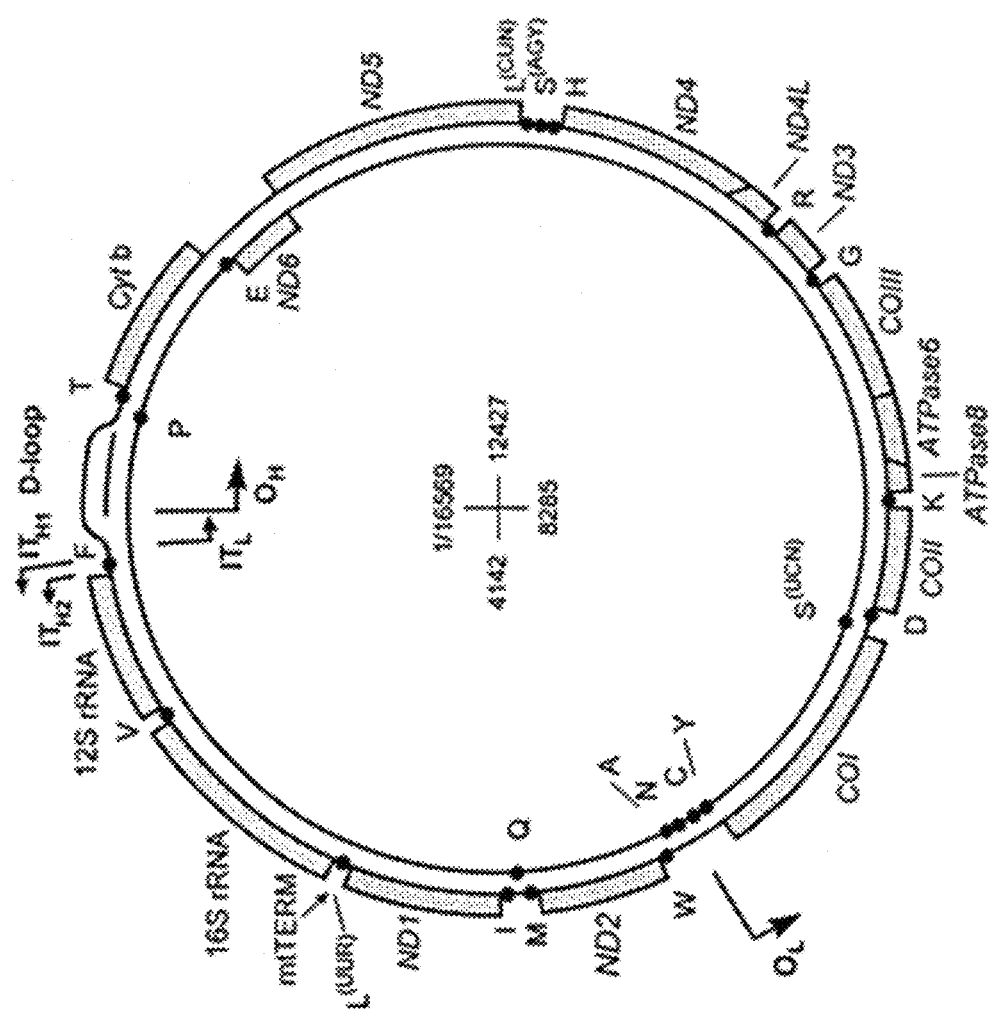
FIG. 22 illustrates an outline of the human mitochondria genome (this figure is taken from Taanman[2]).

A person skilled in the art would understand that mitochondria in mammalian cells contain circular, double-stranded DNA that is roughly 16 kb long. The DNA duplex contains a heavy and light strand, with most of the genes encoded into the heavy strand. Overall, human mitochondria encode for 37 genes, which include 2 rRNAs, 22 tRNAs, and 13 proteins (see schematic illustration of FIG. 22).

In these embodiments, the methods herein described can be used to study mitochondrial genome arrangement and how such arrangement regulate factors related to gene expression.

In some embodiments, the methods herein described can be combined with Hi-C like methods coupled with next-generation sequencing to map the mitochondrial genome.

In-mitochondria barcoding methods herein described can be configured to understand the role mtDNA organization has in mammalian cells. In particular, these methods can be used to understand whether the role of mitochondrial and nuclear interactions in regulating gene expression in mitochondria, whether these regulations are impacted by mtDNA organization Understanding these are important in the grand scheme of addressing the impacts mtDNA has in numerous applications. Indirectly, learning about mitochondrial genome organization could answer some side questions about the symbiotic origins of mitochondria.

In several embodiments of the methods herein described, the methods herein described can be configured to barcode complexes configured for further transcriptome analysis, such as by multiplexed RNA sequencing. The barcoded nucleic acids can be prepared for genome analysis, such as by multiplexed DNA sequencing. The barcoded nucleic acids can be prepared for specific nucleic acids quantification performed by nucleic acid amplification including PCR, or isothermal nucleic acid amplification.

In several embodiments of the methods herein described, the methods herein described can be configured to barcode complexes configured for further nucleic acid sequencing, which can determine the origin of a species in cases of bacteria, fungi, virus or other infectious agents. The barcoded nucleic acids can be analyzed for DNA and RNA mutations including insertions, inversions, deletions, point mutation, copy number variants, duplications, translocations, and many other known genetic events and changes. The barcoded nucleic acids can also be analyzed for RNA sequences, for gene expression profiling, RNA isoforms, and for repeat expansions, In several embodiments of the methods herein described, the methods herein described can be configured to barcode complexes configured for further detecting the changes in DNA and RNA in response to a stimulus of interest, including but not limited to antibiotics.

In several embodiments of the methods herein described, the methods herein described can be configured to determine three-dimensional structure of in-cell or in-organelle complexes. In those embodiments, the method herein described has a number of advantages over existing methods. Specifically, (i) the method of the disclosure provides information about all DNA associated RNA molecules within a genome in a single reaction as opposed to a single species. (ii) The method of the disclosure provides information about chromosome-associated RNA within the context of overall nuclear structure, effectively combining the output of two experiments into one. [57-59] (iii) The method of the disclosure has a higher information content than that of existing experiments, which rely on contact pairs to identify interactions. [57, 58] For example, in a Hi-C experiment, 10 reads have the potential to result in 10 contact pairs. In a split-and-pool experiment, however, the number of contact pairs resulting in a single experiment depends on the number of sequences in a single complex and scales as $\Sigma_1^n n-1$. Therefore, if in a split-and-pool experiment all 10 reads belong to the same complex, that results in 45 contact pairs. In addition to the contact pairs, the split-and-pool method provides higher-order information about the relationships between contact pairs by preserving complexes, which existing methods can only achieve in the ensemble.

Additional advantages of the methods herein described will identifiable by a skilled person upon reading of the present disclosure.

In some embodiments, the cell can be a prokaryotic cell, eukaryotic cell or cells infected by a phage or virus. The analyzed nucleic acids cells can originate from more than one type of cells, including but not limited to host and parasite, immune cell and a pathogen, mammalian cells and co-habiting bacterial or fungal cells.

The methods to perform single-cell marking of a nucleic acid and/or protein in a sample comprising a plurality of cells of the instant disclosure can be performed with a corresponding system to perform single-cell marking of nucleic acid and/or protein complexes in a sample comprising a plurality of cells. The system comprises permeabilization reagents and reagents for tagging molecular complexes for simultaneous combined or sequential use in any one of the methods to perform single-cell marking of nucleic acid and/or protein complexes herein described.

In some embodiments of the system herein described, the system further comprises reagents for isolating cells and/or organelles thereof, reagents for crosslinking cells, and/or reagents for fragmenting the nuclear acid and/or protein material of the permeabilized cells and/or organelles thereof.

In some embodiments of the system herein described, the system further comprises reagents for in-cell or in-organelle barcoding using split-and-pool approach. For example, the system may contain any means for distributing or sorting suspensions, such as a well or plate, and any means for pooling the sorted suspensions into one pooled suspension.

In some embodiments of the system herein described, the system further comprises a microfluidic device and related reagents for isolating cells or organelles thereof into a plurality of single cells or single organelles for in-cell or in-organelle barcoding.

In some embodiments of the system herein described, the system further comprises labels for detection of the barcoded nucleic acid and/or protein complexes and/or related nucleic acid and/or protein components.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

Accordingly, additional components of the system can comprise labeled polynucleotides, labeled antibodies, labels, a microfluidic chip, reference standards, and additional components identifiable by a skilled person upon reading of the present disclosure.

The systems herein disclosed can be provided in the form of kits of parts. In kit of parts for performing any one of the methods herein described, the reagents for the related single-cell marking of a nucleic acid and/or protein can be included in the kit alone or in a pre-mixed reagent mixture as well as with tags for barcoding the nucleic acids and/or proteins.

In a kit of parts, the reagents, tags and additional components required for the related in-cell or in-organelle barcoding identifiable by a skilled person are comprised in the kit independently possibly included in a composition together with suitable vehicle carrier or auxiliary agents. For example, one or more probes can be included in one or more compositions together with reagents for detection also in one or more suitable compositions.

Additional components can include microfluidic chip, reference standards, and additional components identifiable by a skilled person upon reading of the present disclosure.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Further details concerning the identification of the embodiments of methods and systems of the disclosure and related compositions, that can be performed in combination with such devices can be identified by the person skilled in the art upon reading of the present disclosure.

EXAMPLES

The methods and system herein disclosed are further illustrated in the following examples, which are provided by way of illustration and are not intended to be limiting.

The following material and methods were used in performing the experiments reported in the following examples.

Example 1: Isolating Cells from a Sample

Isolation from a sample in accordance with embodiments herein described can be performed by treating the sample with trypsin, which allows for the dissociation of adherent cells and breaks proteins adhering cells together.

Trypsin can be pre-warmed from 4° C./RT to 37° C. to prevent a temperature shock for the cells. Usually, a concentration ranging from 0.025% to 2.5% trypsin (equivalent to 1× to 10× strength) is applied, depending on how adherent the cell line is. Minimal amounts of trypsin is added relative to the area of the plate/flask, usually about 0.5 mL of trypsin per 10 cm$^2$ of surface area. Trypsin is gently rocked against the surface of the container, and the process of trypsinization is done within 10 minutes ([60] and [61]).

Example 2: Harvesting and Crosslinking Cells

F1 2-1 hybrid wild-type mouse embryonic stem cell (mESC) lines were initially cultured in serum-free 2i/LIF medium as described by Engreitz in 2014 [29].

Prior to harvesting the F1 2-1 cell line, TVP solution (1 mM EDTA, 0.025% Trypsin, 1% Chicken Serum (Sigma); prepared in PBS) and wash solution (DMEM/F-12 media containing 0.03% BSA) are pre-warmed at 37° C. Once warmed, 5 mL of TVP solution was added to 15 cm plate containing F1 2-1 mESCs. The plate was gently rocked for 5 mins to lift the adherent cell line off of the plate. Afterwards, 25 mL of wash solution was added to the plate to inactivate TVP, and the resulting cell solution was transferred to a 50 mL conical tube. The cell suspension was then triturated using blunt-tip metal needles (McMaster Carr) to maintain a single cell suspension. The suspension was initially passed through a 20 gauge needle five times, then a 24 gauge needle three times, and a 25 gauge needle once. Cells were then centrifuged at 330 g for 3 mins at room temperature. The supernatant was discarded, and the cells were washed once with 4 mL of 1×PBS for every 10 million (10M) cells.

For the initial crosslinking with disuccinimidyl glutarate (DSG), a desired concentration of 2 mM DSG (Pierce) in PBS will be attained, but DSG and PBS are added separately. After the wash, 3.98 mL of PBS per 10M cells was added to resuspend the pellet. The cell suspension was then passed through a 20 gauge blunt-end needle three times, and a 22 gauge blunt-end needle once. After trituration, 16 μL of 0.5M DSG was added per 10M cells, and the cell suspension was crosslinked while gently rocking in DSG at room temperature for 45 minutes. The resulting solution was then quenched with 200 μL of 2.5M glycine per 1 mL of DSG solution for 5 minutes. Cells were spun down at 1000 g for 4 minutes and washed once with 4 mL of 1×PBS per 10M cells. A second crosslinking was done to achieve a final concentration of 1% formaldehyde (FA). Cells were resuspended in 3.75 mL of pre-warmed (37° C.) 1×PBS and triturated again by passing through a 20 gauge blunt-end needle three times, and a 22 gauge blunt-end needle once. Afterwards, 0.25 mL of 16% FA was added to the cell solution and was rocked gently for 10 mins. The resulting solution was then quenched with 200 μL of 2.5M glycine per 1 mL of FA solution for 5 minutes. Cells were spun down at 1000 g for 4 min at 4° C. The cells were washed twice by adding 4 mL of pre-cooled (4° C.) 0.5% BSA in 1×PBS per 10M cells. The cells were then aliquotted into 5M cell aliquots in 1.5 mL Eppendorf tubes, where they were flash frozen with liquid nitrogen and stored at −80° C.

Example 3: Cell Membrane Lysis and Nuclear Isolation

The 1% FA-2 mM DSG crosslinked cell pellets (5M) were lysed to isolate nuclei for downstream in-nuclei processes. The pellets were first resuspended in lysis buffer 1 (50 mM HEPES pH 7.4, 1 mM EDTA pH 8.0, 1 mM EGTA pH 8.0, 140 mM NaCl, 0.25% Triton-X, 0.5% Nonidet P-40 (synonymous to IGEPAL CA-630), 10% Glycerol) supplemented with 1× Proteinase Inhibitor Cocktail (PIC) and triturated three times with a 20-gauge blunt-end needle, three times with a 24-gauge blunt-end needle, and once with a 30-gauge blunt-end needle. The cell mixture was incubated on ice for 10 minutes before centrifuging down at 900 g for 8 minutes at 4° C. The pellet was next resuspended in lysis buffer 2 (10 mM Tris pH 8.0, 1.5 mM EDTA pH 8.0, 1.5 mM EGTA pH 8.0, 200 mL NaCl) supplemented with 1×PIC.

The same trituration and incubation steps were performed as demonstrated previous for lysis buffer 1, followed by a centrifugation at 900 g for 9 minutes at 4° C. The resulting nuclei pellet is resuspended in 800 μL of nuclei buffer (1×PBS, 1 mM EDTA pH 8.0, 1 mM EGTA pH 8.0, and 0.1% Triton X-100), triturated three times with a 20-gauge blunt-end needle, three times with a 24-gauge blunt-end needle, and once with a 30-gauge needle (blunt-end or hypodermic from this point on), and spin-filtered at 400 g at 1 minute through a 10 μm pore size pluriStrainer (pluriSelect) attached to a 50 mL conical tube. The filter was washed with 500 μL of nuclei buffer before transferring the filtrate to a 1.5 mL Eppendorf tube.

Example 4: Hypotonic Cell Lysis and Restriction Enzyme Digestion in Nuclei

In this example, cell lysis and restriction enzyme digestion are performed according to the following steps as follow.
1) a cell pellet that was previously obtained was resuspended in 1 mL of ice-cold HLB and mixed by pipetting.
2) the cell mixture was then incubated on ice for 10 min.
3) cell suspension was vortexed for 10 s
4) cell suspension was centrifuged for 8 min at 800 g at 4° C.
5) supernatant from centrifugation was discarded
6) nuclei pellet was washed 3 times. For each step 300 μL of HLB buffer was added and the cell suspension was made by pipetting
   cell suspension was centrifuged for 2 min at 400 g
7) following last wash, the pellet was washed twice: first, wash with 800 μL of 1.2×NEB CutSmart buffer
   second, wash with 400 μL of 1.2×NEB CutSmart buffer
   In each of the washes, the pellet was not resuspended. The cells were centrifuged at 400 g for 2 min in between washes, and the supernatant was removed and replaced with the next wash
8) with the cells in 400 μL of 1.2×NEB CutSmart buffer, 6 μL of 20% SDS was added (final conconcentration of SDS—0.3% wt/vol). Cells were resuspended and placed on the thermoshaker for 60 min at 37° C. at 950 rpm
9) adding on to the solution from (8) (nothing was centrifuged or removed), 40 μL of 20% Triton X-100 was added (final conconcentration of Triton X-100-1.8% wt/vol). Cells were resuspended and placed on the thermoshaker for 60 min at 37° C. at 950 rpm
10) adding on to the solution from (9) (nothing was centrifuged or removed), 30 μL of 5000 units/mL HpyCH4V (final—150 units) was added. Cells were resuspended and placed on the thermoshaker for 14.5 hours at 37° C. at 950 rpm.

Table 1 shows the freshly made HLB buffer for cytoplasmic lysis.

TABLE 1

| Reagents | Final Conc | Volume Added |
| --- | --- | --- |
| 1M Tris pH 7.5 | 10 mM Tris pH 7.5 | 0.1 mL (100 μL) |
| 5M NaCl | 10 mM NaCl | 0.02 mL (20 μL) |
| 1M MgCl$_2$ | 3 mM MgCl$_2$ | 0.03 mL (30 μL) |
| 10% NP-40* (v/v) | 0.3% NP-40* (v/v) | 0.3 mL (300 μL) |
|  | 10% glycerol (v/v) | 1 mL (1000 μL) |
|  | H$_2$O | 8.55 mL (8550 μL) |
| Total Volume |  | 10 mL |

*= NP-40 in this case is Nonidet P-40 (also goes by IGEPAL CA-630)

Example 5: Nuclear Membrane Permeabilization and in-Nuclei DNA Digestion

The filtered nuclei solution is centrifuged at 3000 g for 10 min at room temperature and resuspended in 800 μL of 1.2×NEB CutSmart buffer. The nuclei are centrifuged again at 3000 g for 10 min at room temperature and 400 μL of 1.2×NEB CutSmart buffer was gently added to avoid resuspending the pellet. After, 6 μL of 20% SDS was added and the pellet was resuspended and triturated three times with a 20-gauge blunt-end needle, three times with a 24-gauge blunt-end needle, and once with a 30-gauge needle. The nuclei were incubated on Eppendorf ThermomixerC while shaking at 1200 rpm for 60 minutes at 37° C. After 5 minutes of incubation and SDS is fully dissolved, the nuclei were triturated twice more through a 30-gauge needle. Following nuclear membrane permeabilization with SDS, 40 μL of 20% Triton X-100 is added to quench the SDS, and the incubation on Eppendorf ThermomixerC under the same conditions previously described. Lastly, 30 μL of NEB's HpyCH4V is added and allowed to incubate at 19 h while shaking at 1200 rpm at 37° C.

Figure 15:
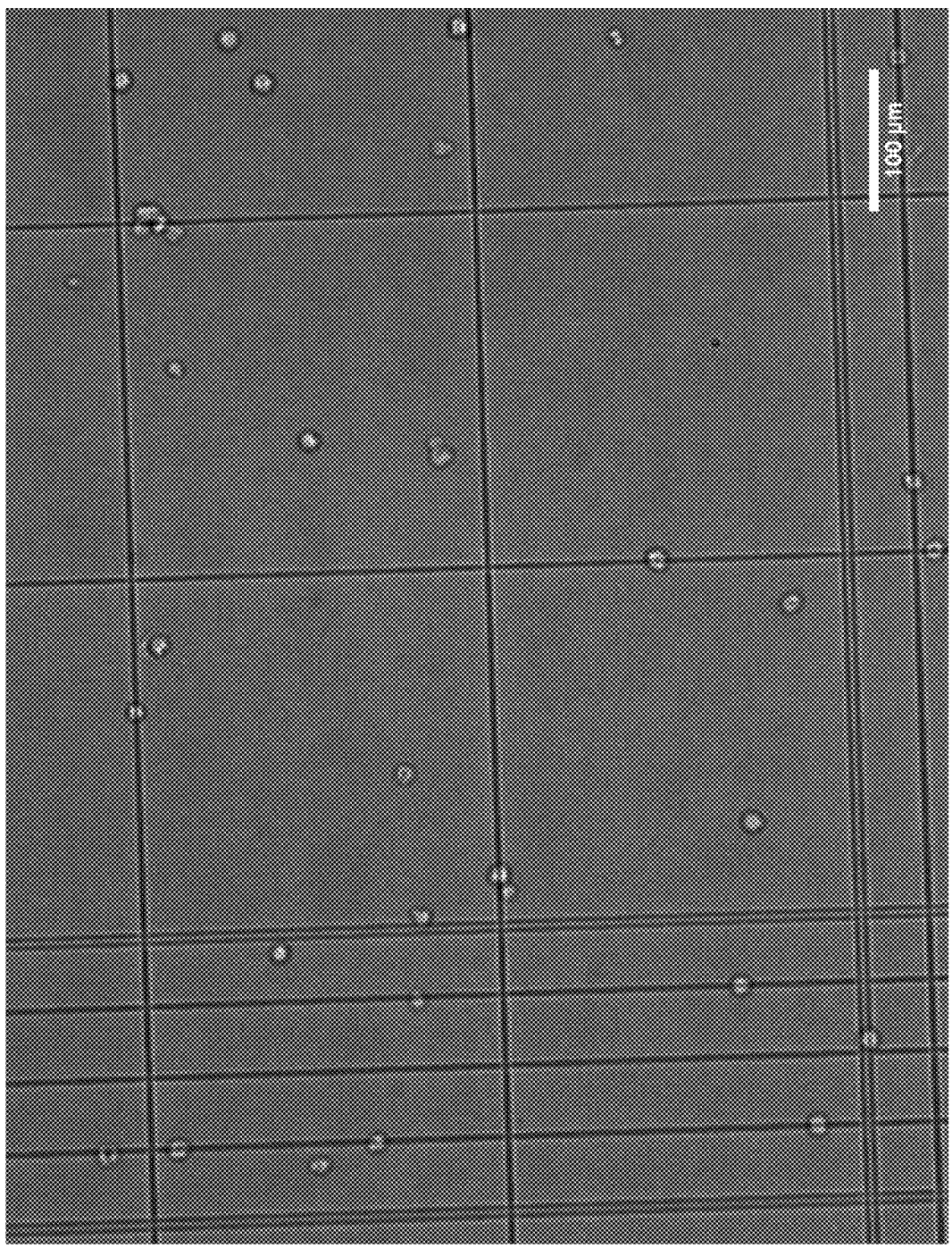
FIG. 15 shows 1% FA-2 mM DSG crosslinked nuclei after 19 h of DNA digestion using the restriction enzyme HpyCH4V and trituration using needles as previously described. Mostly single nuclei are present in solution, consisting between 75-85% of the solution. The remainder of the solution consists of small nuclei clumps, ranging between 2-4 nuclei per clump
Figure 16:
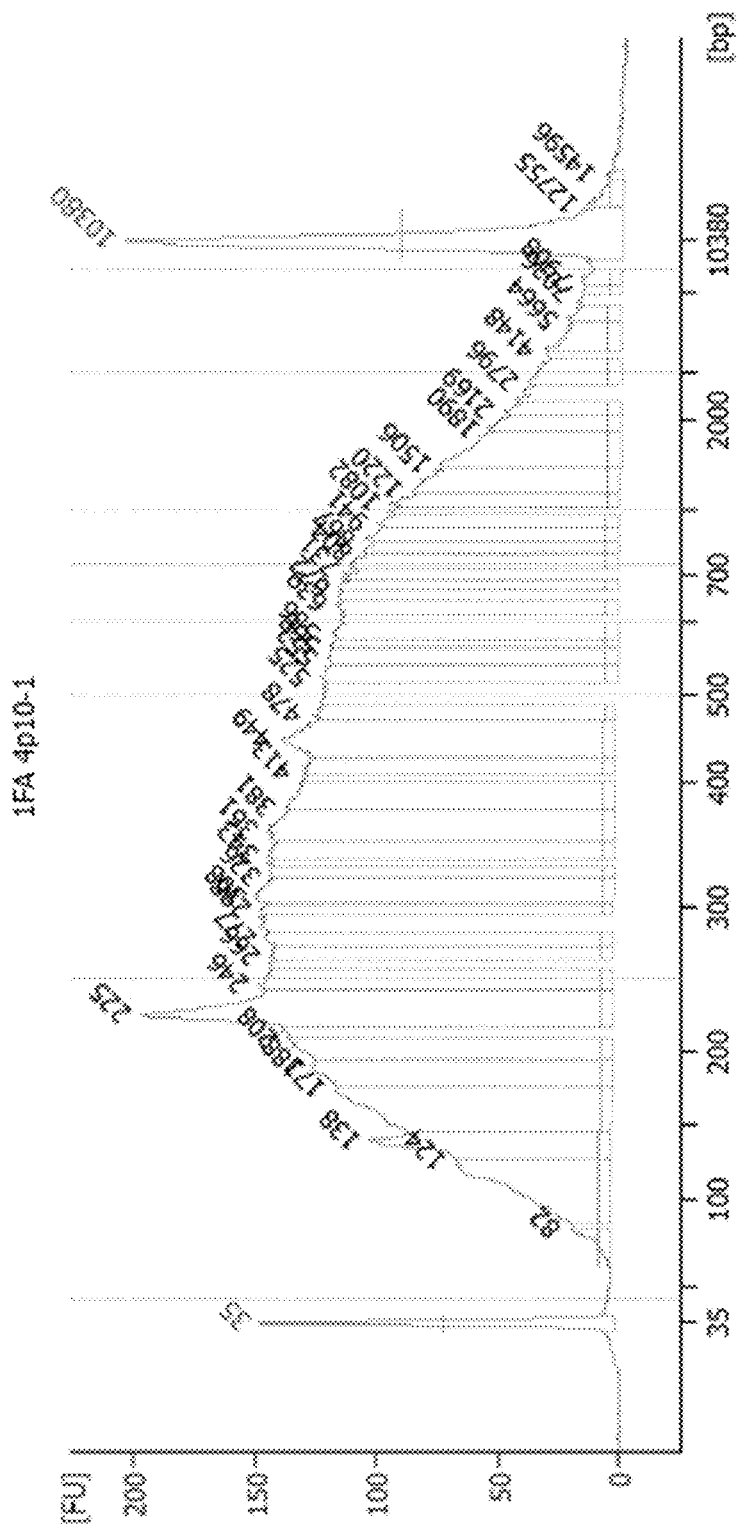
FIG. 16 shows a gray scale version of an electropherogram of DNA sizes and relative concentrations after 19 h of DNA digestion with the restriction enzyme HpyCH4V. With a crosslinking concentration of 1% FA-2 mM DSG, the average digest size is about 600-700 bp, with about 80% of DNA fragments smaller than 600 bp.

Post-digestion, the nuclei were washed twice with nuclei buffer and triturated after the washes by passing the nuclei three times with a 20-gauge blunt-end needle, three times with a 24-gauge blunt-end needle, and three times with a 30-gauge needle (FIG. 15) and DNA fragment size was measured using Agilent Bioanalyzer 2100 (FIG. 16). dA-tailing of the DNA fragments was carried out in-nuclei using NEB's dA-tailing module at 37° C. for 90 minutes followed by washing and trituration as it was just described.

Example 6: DA Tailing in Nuclei

An aliquot of 100 μL was used for dA tailing. The aliquot was originally centrifuged (400 g for 2 min) and the supernatant was extracted. The following reagents shown in Table 2 were then added to the pellet for dA tailing:

TABLE 2

| Exemplary reagents for dA tailing | |
| --- | --- |
| Reagent | Volume Added |
| 10X dA-tail reaction buffer | 25 μL |
| H$_2$O | 215 μL |
| Klenow Fragment (exo−) | 10 μL |
| Total Volume | 250 μL |

The mixture was then incubated on thermoshaker for 90 mins at 37° C. at 1000 rpm. The cells were then centrifuged down (400 g for 2 min) and the supernatant was extracted. Cells were washed twice with a solution containing 1×PBS, 1 mM EDgTA, and 0.1% Triton X-100.

Example 7: Adapter Ligation in Nuclei

After dA tailing, the cells were observed under a C-chip. To isolate single cells and remove all clumps, the cells were sent through a 5 μm cell strainer then centrifuged at 200 g for 2 min to get material through the filter.

Bulk controls were prepared as follows:
Doing both 100 cells (for positive controls) and 5 cell tests in tubes
Duplicate tests for 100 cells, quadruple tests for 5 cells
Quadruple for 5 cells since previous tests with 5 cells have been a hit and miss—if we're really obtaining countable single cells this time, we should be able to accurately perform 5 cell tests each time
Table 3 below shows the reagents used for 100 cells and 5 cells.

TABLE 3

| | Reagents | |
|---|---|---|
| | 100 cells | 5 cells |
| monotemplate dA adapters (500 nM initially-> final conc of 20 nM) | 4 µL | 0.4 µL |
| 2X instant sticky end mix | 50 µL | 5 µL |
| BSA (initial conc: 20 mg/mL-final conc: 1 mg/mL) | 5 µL | 0.5 µL |
| Water | 18.5 µL | 2.97 µL |
| nuclei (stock: 4.44 nuclei/µL) | 22.5 µL | 1.13 µL |
| Total | 100 µL | 10 µL |

Adapter ligation was performed for 6 hours at 25° C.
Afterwards, the tubes were spun down at 400 g for 2 min and the cells were washed 2× with 1×PBS, 1 mM EDgTA, and 0.1% Triton solution
The contents of each tube were then coupled to 100 µL of NHS beads overnight at 6° C. at 1000 rpm
After coupling, the beads were washed once with M2 buffer before being quenched for 3 hours at 12° C. at 1000 rpm using 1M Tris, 0.5 mM EDgTA and 0.1% Triton
After quenching, the beads were washed once with LoTrEe buffer before performing barcode ligation
Single cell controls were prepared as follows:
Doing stochastic loading of single cells across 16 wells at 60% occupancy (cells loaded ideally—9.6) in a lobind 96 well plate
10 µL ligations in each well over 16 wells=160 µL
Aiming for a final concentration of 0.06 cells/µL (=9.6 cells/160 µL).
Table 4 shows the reagents in the final centration.

TABLE 4

| | Reagents | |
|---|---|---|
| | 1 well | 16 wells |
| monotemplate dA adapters (500 nM initially-> final conc of 20 nM) | 0.4 µL | 6.4 µL |
| 2X instant sticky end mix | 5 µL | 80 µL |
| BSA (initial conc: 20 mg/mL-final conc: 1 mg/mL) | 0.5 µL | 8 µL |
| Water | 3.96 µL | 63.44 µL |
| nuclei (stock: 4.44 nuclei/µL-final conc: 0.06 nuc/µL) | 0.14 µL | 2.16 µL |
| Total | 10 µL | 160 µL |

The 80 µL stock was made consisting of adapters, BSA, water, and nuclei—then 5 µL of this stock was deposited in each of the 16 wells. Afterwards, 5 µL of sticky mix was then added to each of the wells
Adapter ligation was performed for 6 hours at 25° C.
Afterwards, the plate was spun down using the mini plate spinner for 2 min and the cells were washed 2× with 1×PBS, 1 mM EDgTA, and 0.1% Triton solution The contents of each well were then coupled to 25 µL of NHS beads overnight at 6° C. at 1000 rpm (the beads were not pooled together). 400 µL of NHS beads were washed 1× with 400 µL of 1M HCl and 2× with each containing 400 µL of 1×PBS. After the PBS wash, the beads were immersed in 400 µL of Urea Lysis Buffer
After coupling, the beads were transferred to individual 1.5 mL tubes (16 tubes in total) and the well in which the beads were was washed once with M2 buffer. The supernatant was removed from the new tube, washed once with M2 buffer before being quenched for 3 hours at 12° C. at 1000 rpm using 1M Tris, 0.5 mM EDgTA and 0.1% Triton
After quenching, the beads were washed once with LoTrEe buffer before performing barcode ligation Example 8: In-Nuclei Combinatorial Barcoding of Molecular Complexes The addition of a unique cell-specific barcode sequence was done through three rounds of combinatorial barcoding, although more may be done if more combinations are needed. Lo-bind 96 well plates were pre-spotted with 2.4 µL of either 45 µM DPM, Odd, or Even barcoded oligonucleotides (see FIGS. 25 to 28). From the previous step, 500,000 nuclei are withdrawn and filled to 1125 µL with 1×PBS+ 0.1% Triton X-100. The nuclei solution is split evenly into the wells of a pre-spotted 96-well plate, and to each well, 6.4 µL of ligation mix (stock batch of 220 µL 2× Instant Sticky-end Ligase Master Mix (NEB), 352 µL of 5×NEB-Next Quick Ligation Reaction Buffer (NEB), and 132 µL of 1,2-Propanediol) is added. The order of barcodes for the cell-specific ligation started with the ligation of DPM barcodes, followed by Odd, and lastly Even.

The ligation was performed at 20° C. on Eppendorf ThermomixerC, where the plate was shaking at 1600 rpm for 30 seconds every 5 minutes. After each ligation round, the 96-well plate was quickly spun down before adding 20 µL of 1×PBS+50 mM EDTA pH 8.0+0.1% Triton X-100 buffer to each well to stop the ligation reaction. The wells were incubation with this solution for 10 mins before pooling the wells together into a 15 mL conical tube. The nuclei solution was centrifuged at 3000 g for 20 mins, followed by removal of supernatant and transferring of the pellet to a 1.5 mL Eppendorf tube.

Figure 17:
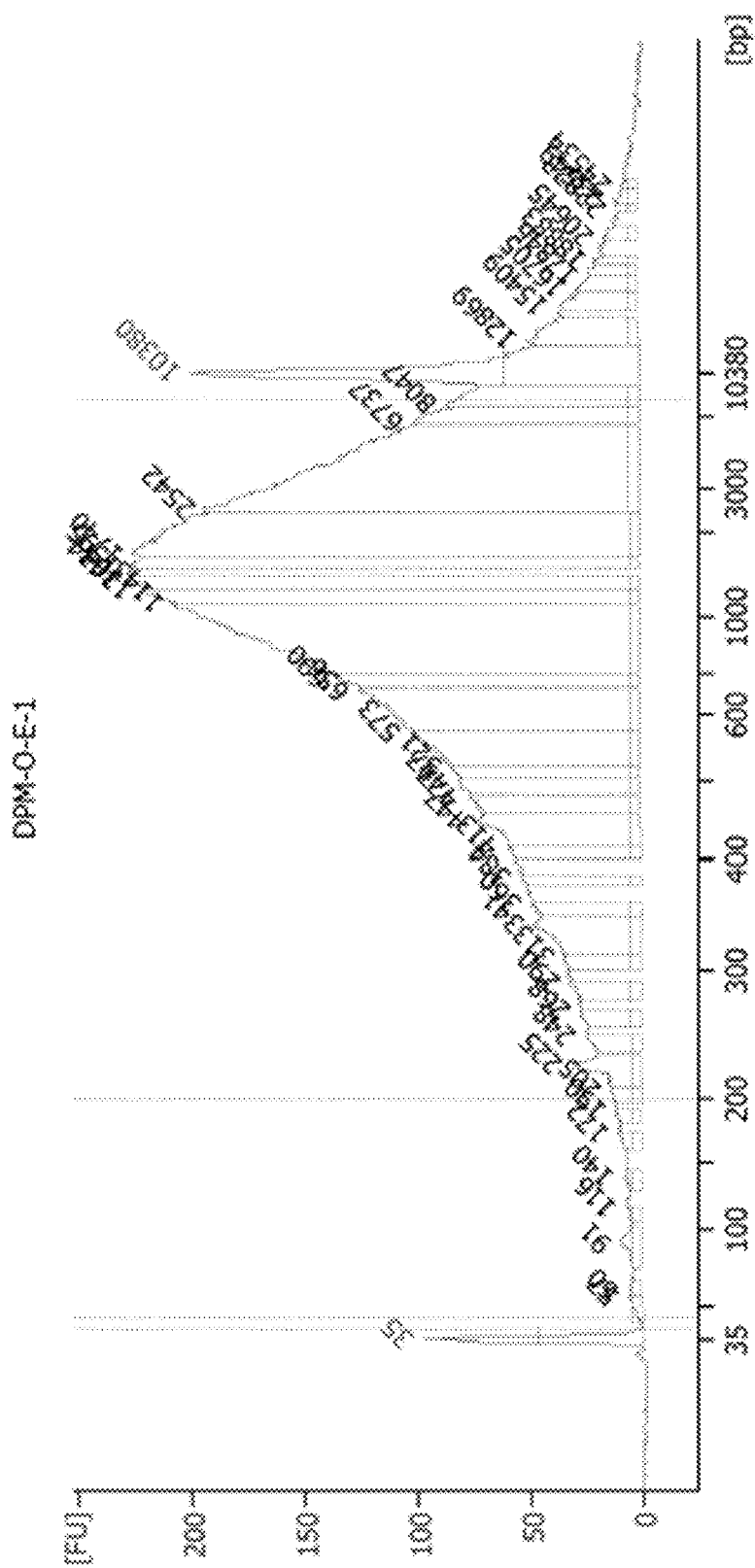
FIG. 17 shows a gray scale version of an electropherogram of DNA sizes and relative concentrations after three rounds of cell-specific combinatorial barcoding.

The nuclei were washed twice more with nuclei buffer (centrifugations of 3000 g for 10 mins) and ending by triturating three times with a 20-gauge needle, three times with a 24-gauge needle, and three times with a 30-gauge needle. The ligation process was repeated twice more for the ligation of the Odd and Even barcodes. After final washes and triturations after the Even barcode addition, the nuclei were resuspended in nuclei buffer and filtered through a 10 µm pluriStrainer (pluriSelect) followed by a 5 µm pluriStrainer (pluriSelect). The resulting nuclei concentration was counted using a 4-Chip Disposable Hemocytomer (Bulldog Bio). DNA fragment size after barcode additions was determined using Agilent Bioanalyzer 2100 (FIG. 17).

Example 9: Barcode Ligation and PCR Setup for Bulk and Single Cell Samples

After LoTrEe wash, beads were washed 1× with RLT2+ buffer and 2× with M2 Buffer (−EDgTA). Barcode ligation mix shown in Table 5 was added. Barcode ligation occurred for 30 mins at 25° C. at 1000 rpm.

TABLE 5

Reagents used in an exemplary barcode ligation mix

| Reagent Added | Volume Added |
|---|---|
| IDT Barcodes - Y-end barcode (stock conc: 45 µM)** | 2.8 µL |
| 2X Instant Sticky End Mix | 20 µL |
| M2 buffer without EDgTA | 10 µL |
| H$_2$O | 7.2 µL |
| Total | 40 µL |

Post barcode ligation, the beads were washed 2× with RLT2+, 2× with PBLSD at 37° C. (3 min for each wash), and 3× with M2 Buffer (−EDgTA). Reverse crosslinking was then done with 93 µL with MyK buffer and 7 µL of Proteinase K at 60° C. for an hour at 1000 rpm. After the hour, supernatant was removed and 20 µL of H$_2$O was added to the beads to remove whatever residual DNA was present. DNA was washed using Zymo's clean-and-concentrator column (5:1 binding buffer to DNA sample, 2× with wash buffer, 6 µL elution buffer).

The following PCR reagents and conditions were used for barcoded material:
  Reagents: 15 µL of Q5 Master Mix, 1.5 µL of 25 µM barcode primers, 1.5 µL of 20× Evagreen (final conc of 1×), 6 µL of sample/template, 6 µL of H$_2$O (split over 3 wells at 9 µL each)
  Conditions: Preincubation at 98° C. for 300 sec with 3 step amplification: 1) 98° C. for 20 sec, 71° C. for 60 sec, 72° C. for 180 sec (for 4 cycles) and then 2) 98° C. for 20 sec, 72° C. for 180 sec (for 26 cycles)
Products were diluted ¼ and run on a 1% agarose gel.

Figure 11:
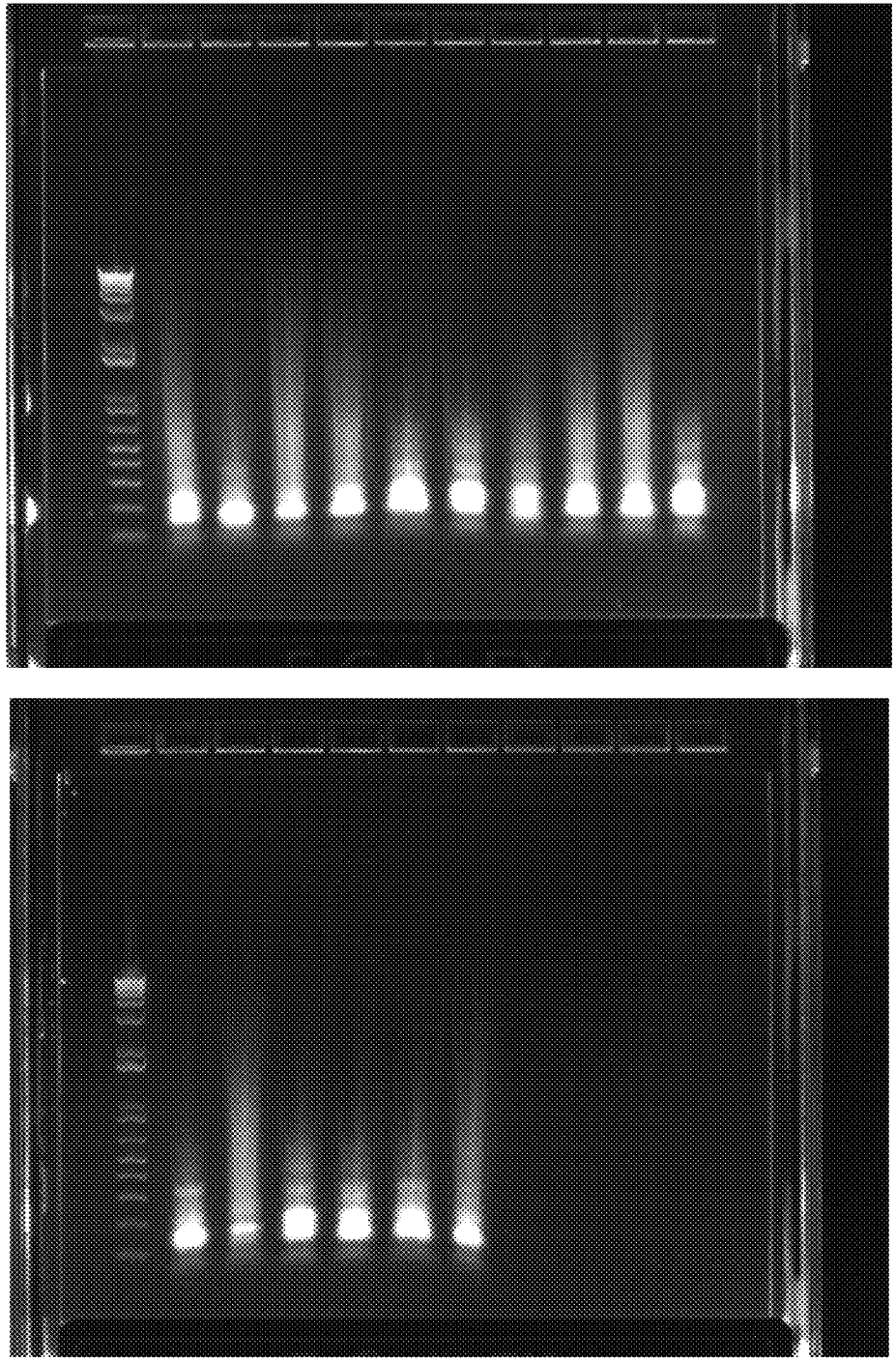
FIG. 11 shows gel electrophoresis of libraries from individual single cells that were Poisson loaded to 60% occupancy on 16 wells of a 96-well plate, barcoded and amplified separately. The left most column shows an E-gel 1 kb Plus DNA ladder. The remaining columns either show a library (indicating a cell was present) or short-fragment amplicons (indicating a cell was not present in that well).

FIG. 11 shows gel electrophoresis of libraries from individual single cells that were Poisson loaded to 60% occupancy on 16 wells of a 96-well plate, barcoded and amplified separately. The left most column shows an E-gel 1 kb Plus DNA ladder. The remaining columns either show a library (indicating a cell was present) or short-fragment amplicons (indicating a cell was not present in that well).

The results illustrated in FIG. 11, shows that in embodiments, where the analysis is directed to analyze a single-cell, the gel demonstrates that it is possible to take the DNA content from a single cell, barcode, amplify, and generate libraries compatible for a sole single-cell analysis.

Figure 12:
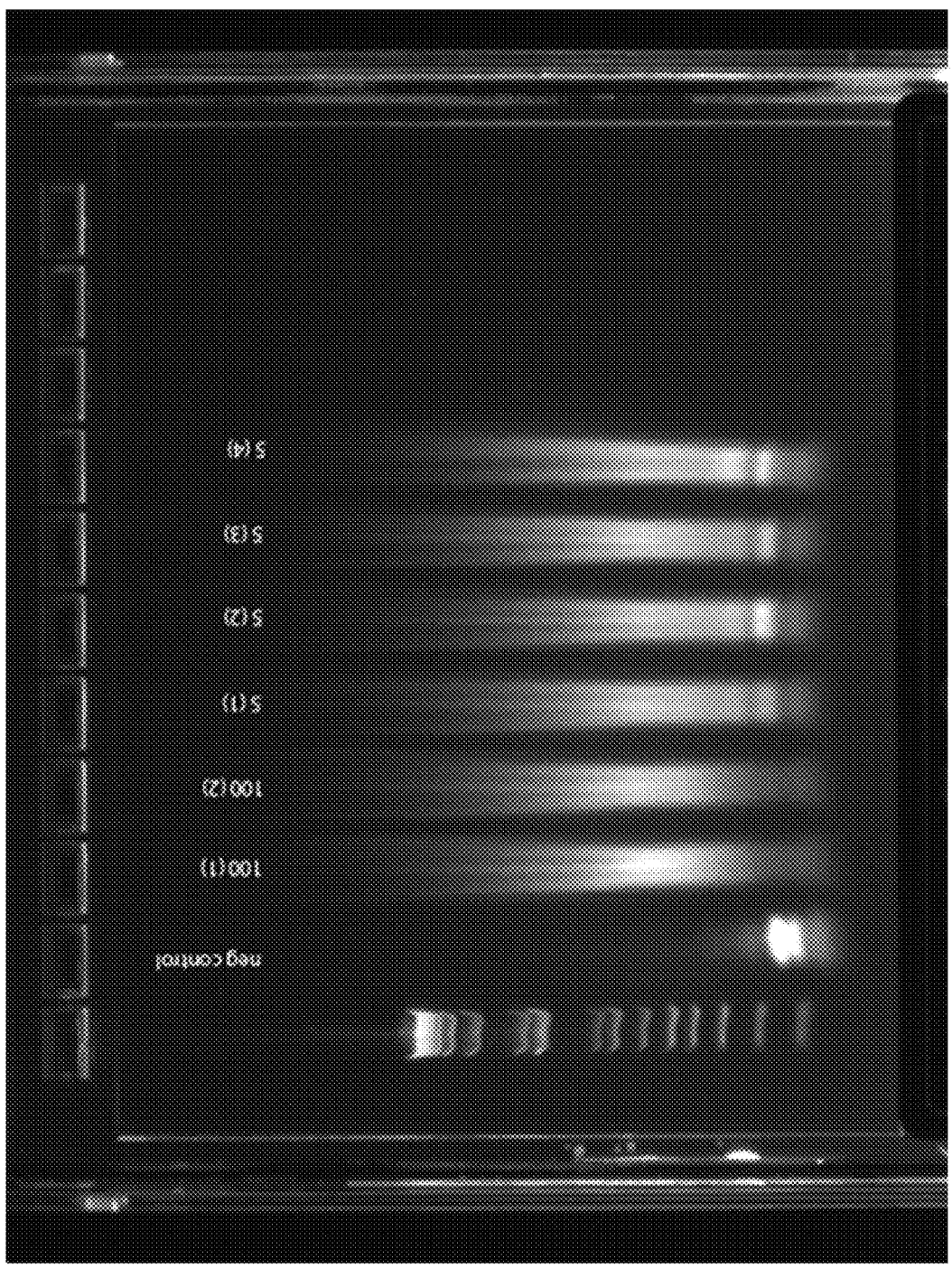
FIG. 12 shows gel electrophoresis demonstrating the ability to generate libraries from few numbers of cells. Column 1 shows an E-gel 1 kb Plus DNA ladder. Column 2 shows a negative control. Columns 3 and 4 are duplicates of demonstrating barcoding of 100 nuclei. Columns 5-8 are quadruplicates of demonstrating barcoding of 5 nuclei.

FIG. 12 shows gel electrophoresis of demonstrates the ability to generate libraries from few numbers of cells. Column 1 shows an E-gel 1 kb Plus DNA ladder. Column 2 shows a negative control. Columns 3 and 4 are duplicates of demonstrating barcoding of 100 nuclei. Columns 5-8 are quadruplicates of demonstrating barcoding of 5 nuclei. The results illustrated in FIG. 12, shows that it is possible to generate libraries from a plurality of cells (e.g. 5 and 100 cells, according to the results illustrated herein).

Example 10: Preparing Single Cells for on Device Loading

The nuclei were passed through a 25 g needle 5× and then strained through a 10 µm filter. Nuclei were counted on a C-chip: concentration of 120 nuclei/µL.
The on-device calculations were performed according to the following protocols:
  Overall device layout contains 48 wells with each well (ideally) containing 3.3 nL per well
  Total volume over 48 wells is 158.4 nL
  Loading occurs at 30% occupancy—aiming for 14.4 cells over 158.4 nL, i.e. concentration of cells to load=90.91 cells/µL
  Made at 10 µL mixture containing cells, BSA, Evagreen, and water to load onto the device (see Table 6)

TABLE 6

Reagents contained in an exemplary mixture to be loaded onto the device

| | Initial Conc | Final Conc | Volume (uL) to mix |
|---|---|---|---|
| Cells (dA tailed) (conc: cells/uL) | 120 | 90.91 | 7.58 |
| BSA (conc: mg/mL) | 20 | 1 | 0.50 |
| Evagreen (conc: X) | 20 | 1 | 0.50 |
| H$_2$O | | | 1.42 |
| | | Total | 10.00 |

The device was assembled according to the following protocol. Two devices were used, each containing 34 adapters. Upon assembly of both devices, all 34 adapters were still present. Device 1 had 23 clumps; device 2 had 10 clumps (majority of the clumps were single cells—about 10-15% consisted of 2-4 cell clumps).

To run through the device, the device was positioned in the first alignment to load cells. The device was then flushed through with 1×PBS, 1 mM EDgTA, 0.1% Triton, and 1 mg/mL BSA and then vacuumed out to coat the glass walls of the device with BSA to limit cell sticking. Cell mixture described previously was then loaded and then slipped in.

After unslipping and realigning for reloading, the device was flushed again with 1×PBS, 1 mM EDgTA, 0.1% Triton, and 1 mg/mL BSA solution and then vacuumed out. 2× instant sticky mix was then flown through and then slipped to mix with the cells/spotted adapters Adapter ligation was performed for 6 hours at 25° C.

Prior to unloading off the device, the unloading channel was flushed through with 1×PBS, 1 mM EDgTA, 0.1% Triton, and 1 mg/mL BSA solution. Device contents were unloaded into a microcentrifuge tube.

Contents of device were washed twice with 1×PBS, 1 mM EDgTA, and 0.1% Triton solution prior to being coupled overnight at 6° C. at 1000 rpm to 100 µL of NHS beads (beads being washed with 1 M HCl and twice with 1×PBS) immersed in urea lysis buffer.

After coupling, the beads were washed with M2 buffer before being quenched for 3 hours at 12° C. at 1000 rpm using 1M Tris, 0.5 mM EDgTA and 0.1% Triton After quenching, the beads were washed once with LoTrEe buffer before performing barcode ligation.

The same barcode ligation and PCR setup procedures described in Example 5 was used for on and off device samples.

Figure 13:
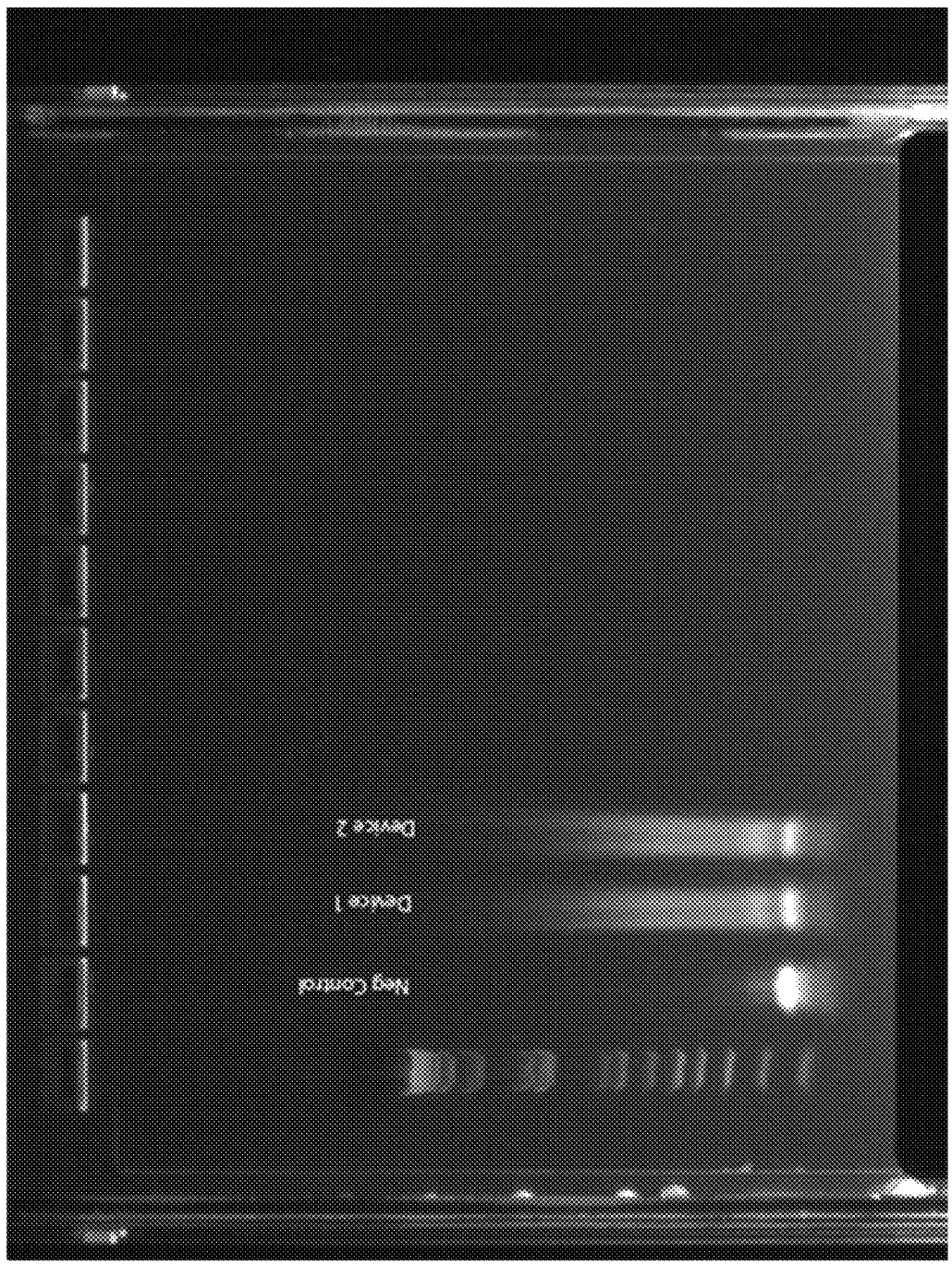
FIG. 13 shows gel electrophoresis of single nuclei libraries (columns 3 and 4) that were originally barcoded on SlipChip devices. Nuclei were loaded 30% occupancy on two separate SlipChip devices with each device containing 48 wells. The nuclei were pooled together after barcoding with complex-specific barcoding occurring off device. Column 1 shows an E-gel 1 kb Plus DNA ladder. Column 2 shows a negative control.

FIG. 13 shows gel electrophoresis of single nuclei libraries (columns 3 and 4) that were originally barcoded on SlipChip devices. Nuclei were loaded 30% occupancy on two separate SlipChip devices with each device containing 48 wells. The nuclei were pooled together after barcoding with complex-specific barcoding occurring off device. Column 1 shows an E-gel 1 kb Plus DNA ladder. Column 2 shows a negative control.

Example 11: Nuclear Lysis and Coupling of Molecular Complexes

Isolation of molecular complexes from cell-specific barcoded nuclei was performed using the Covaris M220

Focused-ultrasonicator. Nuclei were washed twice in lysis buffer 3 (1.5 mM EDTA pH 8.0, 1.5 mM EGTA pH 8.0, 100 mM NaCl, 0.1% sodium deoxycholate, 0.5% sodium lauryl sarconate (NLS)) and resuspended in lysis buffer 3 to achieve a minimum concentration of 100 nuclei/μL. Of this, 1500 nuclei were withdrawn and placed in Covaris microTube-15 and filled to 15 μL with lysis buffer 3. The conditions on the ultrasonicator were applied (Incident Power: 30 W, Duty Cycle: 3.3%, Temperature range: 4° C.-8° C. with 6° C. defined as the setpoint temperature) and the nuclei solution was sonicated for 5 minutes.

In parallel, 600 μL of N-hydroxysuccinimide (NHS)-magnetic beads (Pierce) were activated for coupling the molecular complexes lysed from nuclei. With the aid of a DynaMag-2 Magnet (ThermoFisher), the beads were washed with 600 μL of ice-cold 1M HCl followed by a 600 μL wash of ice-cold 1×PBS. The sonicate containing molecular complexes was added with 585 μL of coupling buffer (1×PBS, 0.1% SDS) to the beads, and the coupling occurred overnight at 4° C. at 1200 rpm. Following coupling, the supernatant was removed and replaced with 600 of quenching buffer (1M Tris pH 7.5, 0.5 mM EDTA pH 8.0, 0.5 mM EGTA pH 8.0, 0.1% Triton X-100), where quenching was done for 60 mins at 4° C. at 1200 rpm. The beads were then washed twice with ice-cold RLT2+ buffer (0.2% NLS, 1 mM EDTA pH 8.0, 1 mM EGTA pH 8.0, 10 mM Tris pH 7.5, 0.1% Triton X-100, 0.1% NP-40; final concentrations attained in Buffer RLT (Qiagen)). The beads were washed thrice more in M2 Buffer (50 mM NaCl, 20 mM Tris pH 7.5, 0.2% Triton X-100, 0.2% NP-40, 0.2% DOC).

Example 12: Combinatorial Barcoding of Molecular Complexes

The molecular complex combinatorial barcoding is done similarly as previously described by Quinodoz in 2018 [1]. Firstly, the beads were resuspended in a solution containing M2 Buffer and nuclease-free $H_2O$ (10 parts M2 buffer to 7.2 parts $H_2O$) to attain a total volume of 1125 μL. Additionally, the wells of a lo-bind 96-well plate were pre-spotted with 2.4 μL of 4.5 μM either Odd, Even, or Y-end barcoded oligonucleotides (see FIGS. 25 to 28).

The order of barcodes for the complex-specific ligation started with the ligation of Odd barcodes, followed by Even, and lastly Y-end. To each well, 11.2 μL of complex-coupled NETS-beads were added followed by the addition of 6.4 μL of ligation mix (stock batch of 220 μL 2× Instant Sticky-end Ligase Master Mix (NEB), 352 μL of 5×NEBNext Quick Ligation Reaction Buffer (NEB), and 132 μL of 1,2-Propanediol). The ligation was performed at 20° C. on Eppendorf ThermomixerC, where the plate was shaking at 1600 rpm for 30 seconds every 5 minutes. After each ligation round, the 96-well plate was quickly spun down before adding 60 μL of RLT2+ buffer to each well to stop the ligation reaction.

The contents from each well were then pooled together into a 25 mL reservoir, and the plate was rinsed with 100 μL of RLT2+ buffer and pooled with the reservoir. The reservoir solution was eventually pooled into a 1.5 mL Eppendorf tube, and the beads were washed thrice with 600 μL of M2 Buffer. The complex-specific barcode ligation was repeated twice more for the addition of the Even and Y-end barcodes.

Once fully barcoded, the beads were split into 10% aliquots. To each aliquot, 92 of MyK buffer (20 mM Tris pH 8.0, 0.2% SDS, 100 mM NaCl, 10 mM EDTA pH 8.0, 10 mM EGTA pH 8.0, 0.5% Triton X-100) and 8 μL of Proteinase K (NEB) was added. The aliquots were reverse crosslinked overnight at 60° C. at 1200 rpm.

Figure 18:
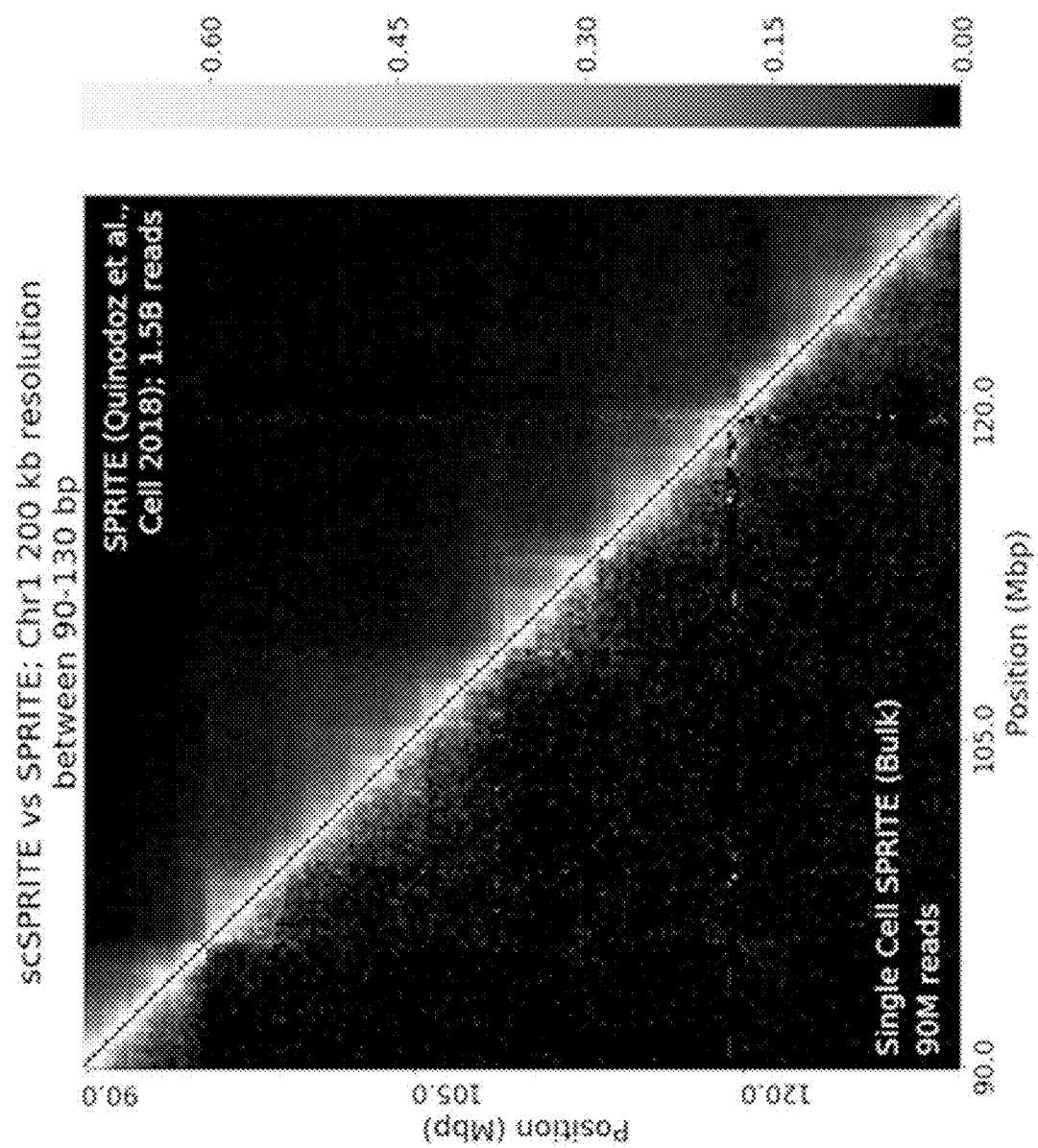
FIG. 18 shows a gray scale version of contact map demonstrating the frequency of interactions in chromosome 1 between 90-130 Mbp of mESCs at 200 kbp resolution. The left half of the contact map is the population of all single cell data from our combinatorial single-cell method. The right half of the contact map is the population-wide data from the original SPRITE method demonstrated by Quinodoz et al. 2018 [1] (Here is demonstrated the ability to recreate the same contacts present in chromosome 1, showing the same short- and long-range contacts as previously characterized and published.
Figure 19:
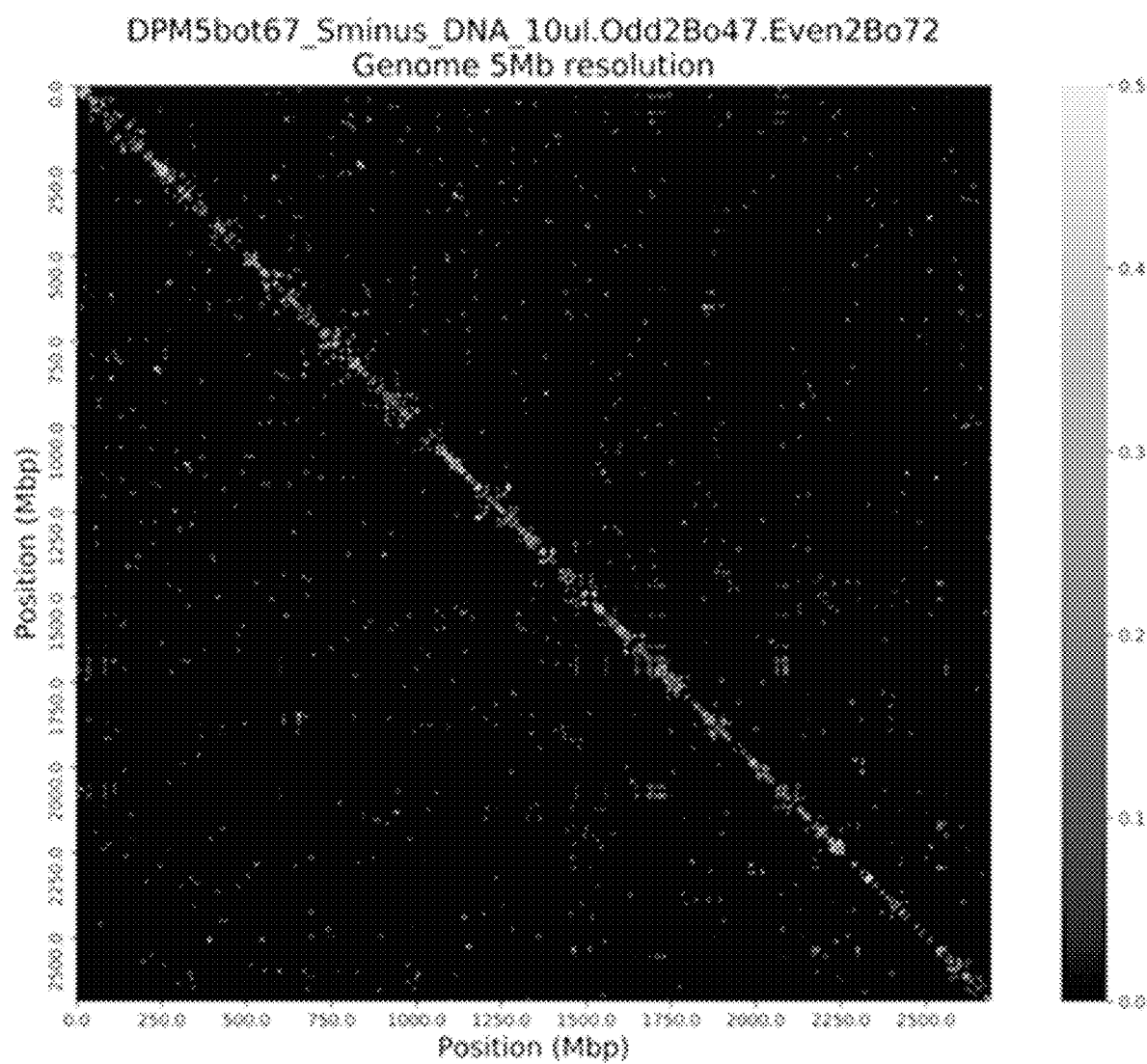
FIG. 19 shows a gray scale version of a contact map from a single cell demonstrating the frequency of interactions at the genome-wide scale at 5 Mbp resolution. Here, preservation of chromosome-territories, is shown, as noted by the high frequency of interactions along the diagonal.
Figure 20:
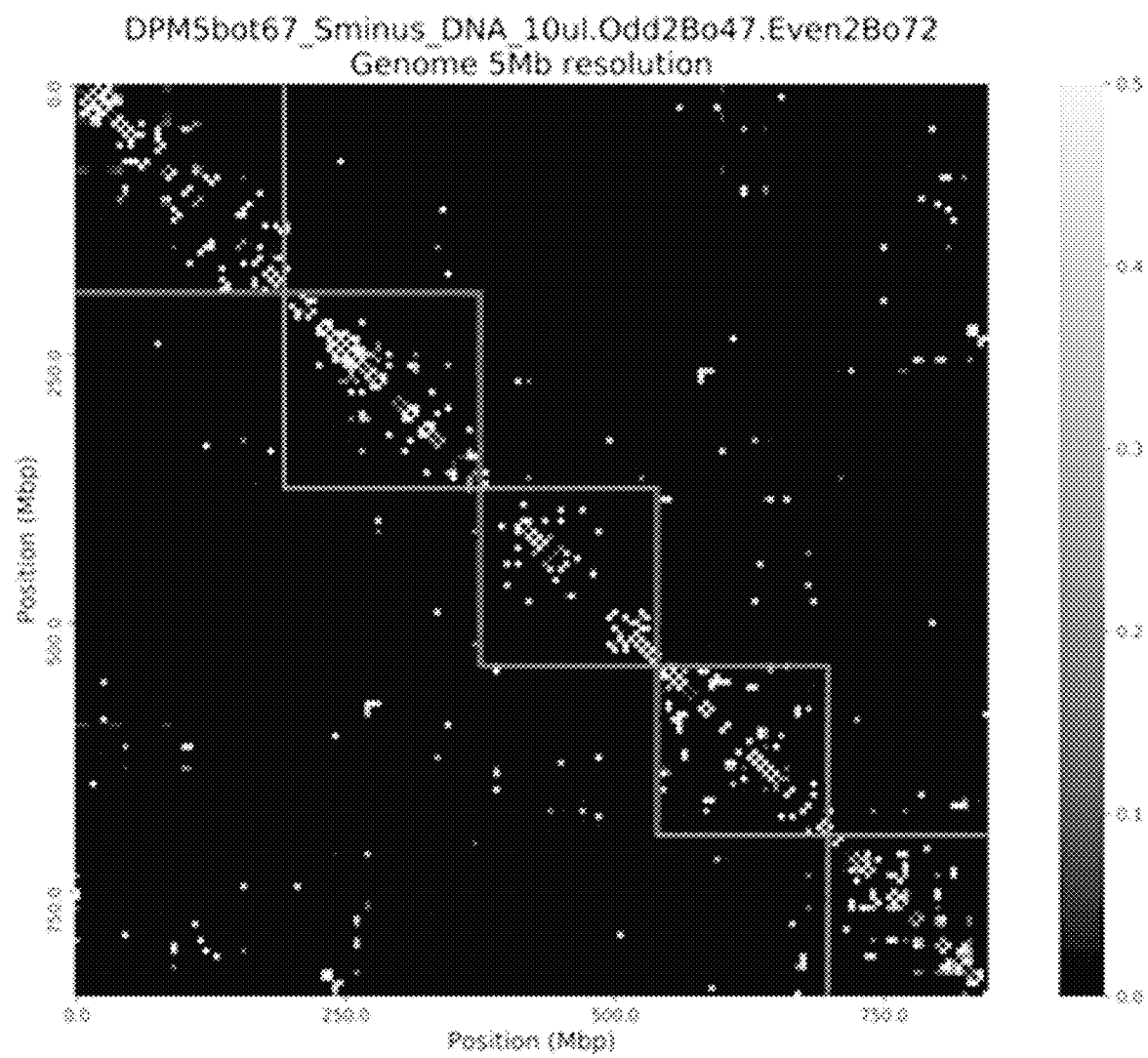
FIG. 20 shows a grayscale version of a contact map from a single cell demonstrating the frequency of interactions at the genome-wide scale at 5 Mbp resolution, but zoomed-in to explore the interactions between chromosomes 1-5. The outlined boxes are the sizes of chromosome 1-5, respectively, as you move from the top-left to the bottom-right of the diagonal.
Figure 21:
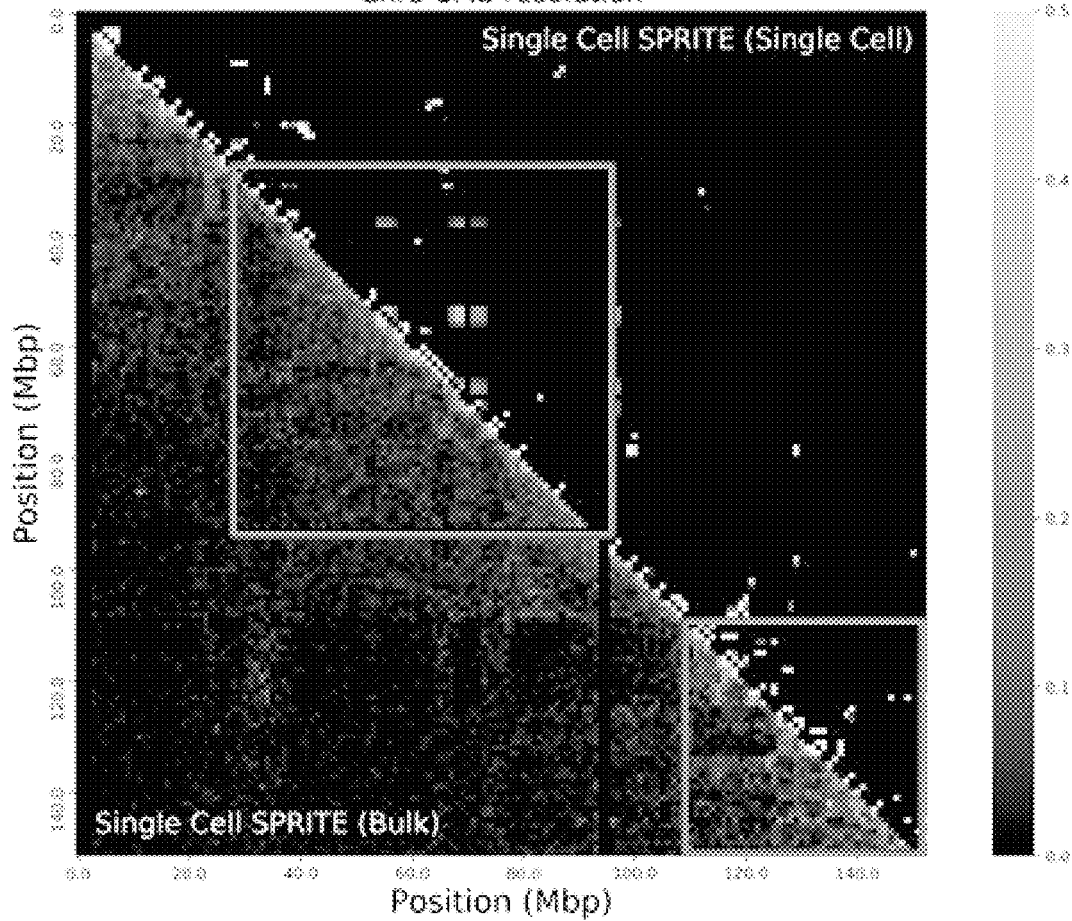
FIG. 21 shows a grayscale version contact map demonstrating the frequency of interactions in chromosome 1 at 1 Mbp resolution. The left half of the contact map is the population of all single cell data from our combinatorial single-cell method. The right half of the contact map is interactions deriving from one of the single cell data sets. The outlined boxes are regions of conserved chromosome interactions between the population and single-cell data sets.

Example 13: Amplification, Purification, Sequencing, and Analysis of Single-Cell Libraries The supernatant containing barcoded DNA from the reverse crosslinked beads was transferred to a new 1.5 mL Eppendorf tube and was purified using Zymo Clean-and-Concentrator-5 column using 5× binding buffer and eluted in 12 μL of nuclease-free $H_2O$. To this, 15 μL of Q5 Hot Start High-Fidelity 2× Master Mix (NEB), 1.5 μL of 20× Evagreen, 0.3 μL nuclease-free $H_2O$, and 1.2 μL of indexed Illumina adaptor primers. DNA was amplified using BioRad CFX96 Real-Time PCR under the following cycle conditions: Step 1—98° C. for 120 s; Step 2—4 cycles of 98° C. for 10 s, 68° C. for 30 s, 72° C. for 90 s; Step 3—1 cycle of 98° C. for 10 s, 70° C. for 90 s. Afterwards, repeated cycles of 70° C. for 10 s, 98° C. for 10 s, and 70° C. for 90 s were performed until early exponential amplification was noted. The amplification was then stopped and a final cycle of 98° C. for 10 s, 70° C. for 180 s was done and was kept at 20° C. forever. The PCR products were diluted 4-fold and loaded into an E-gel EX 1% agarose gel. Gel electrophoresis was done for 10 min, and libraries between 300-1000 bp were cut and purified using Zymoclean Gel DNA Recovery kit using 5× binding buffer. The libraries were lastly purified by performing two rounds of 0.7×SPRI (AMPure XP) beads to remove excess primers. The concentration of libraries and size distribution of our libraries was determined by Qubit 3.0 Fluorometer and Tapestation 2200, respectively. Illumina's HiSeq 2500 instrument was used to generated paired-end sequencing data with read 1=95 bp and read 2=120 bp. The barcode identification, alignment, clustering, and heatmap generation was done as described by Quinodoz in 2018 [1], but with read 2 having the barcode sequence of Odd-Even-Odd-Even-Y (FIG. 18). To parse the data into single-cell files, the clustering files were sorted to individual files by pulling all clusters containing the same first three barcodes (DPM-Odd-Even) (FIGS. 19-21).

Example 14: Simplified Single-Cell Preparation Technique

A number of the steps addressed previously are performed in bulk off-device to allow for the use of validated existing chemistries for bulk reactions.

A method has been developed [57, 62], to keep the nuclear contents separate during all processing steps off-device. This method involves lysing cells, porating nuclei, and using the porated nucleus as a contained environment in which to perform all enzymatic processing steps. This nuclear poration protocol has also already been validated as a way to maintain nuclear structure in single-cells via Hi-C analysis to determine DNA-DNA contact pairs[57, 62] and also as a way to increase the yield in the Hi-C protocol [58, 63].

The method takes cells that have been formaldehyde crosslinked, and performs a nuclear isolation, followed by a nuclear poration using sodium dodecyl sulfate. After the nuclear poration, the chromatin in the nuclei is digested using a restriction enzyme. In our protocol, the restriction enzyme used is HpyCH4V which cuts on the sequence TGCA leaving a blunt end. After digestion of the chromatin, the DNA ends are dA-tailed in-nuclei prior to ligation of the universal adapters. After this point, the nuclei are lysed, and the split-and-pool protocol proceeds. In this nuclear poration protocol, all steps prior to ligation of the universal adapter can be performed in bulk with many cells. Ligation of the universal adapter would require separation of the nuclei to ensure that each nucleus received a uniquely barcoded adapter through isolation on a microfluidic device or 96-well plate.

Figure 4:
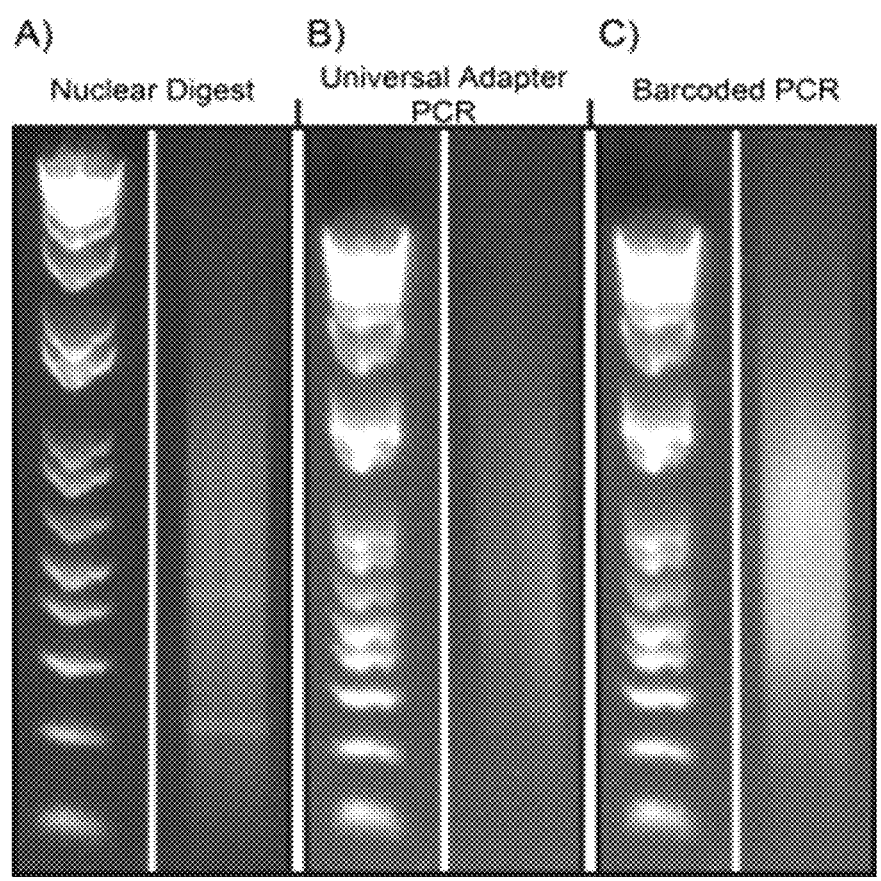
FIG. 4 shows gel images obtained at various states of a sample of nuclei used for split-and-pool barcoding after in-nuclei ligation: (A) the distribution of fragments obtained after restriction digest; (B) the distribution of amplified product acquired from (A) after addition of a universal adapter by in-nuclei ligation followed by lysis and bead-coupling; and (C) the distribution of amplified product acquired from (B) after in five rounds of split-and-pool barcoding. Products (B-C) were amplified using PCR. In the left side of each panel, an E-Gel 1 kb plus ladder is shown.

The first step in developing an in-nuclei processing approach was to determine the proper restriction enzyme or mixture of enzymes to fragment the chromatin into 300-700 bp fragments. A 4-base cutter would be preferable because given a random genome the enzyme would cut the DNA on average every $4^4$ or 256 bases. One suitable enzyme is the HpyCH4V enzyme, which cuts on the recognition sequence TGCA and under experimental procedures is capable of digesting 1% formaldehyde PSM-33 mouse embryonic stem cells (FIG. 4, panel A). After digestion, the nuclei were prepared for ligation using the NEBNext dA-tailing module, and as a bulk control had a universal adapter ligated. These nuclei were then lysed and the contents of the nuclei were coupled to beads. To confirm that the nuclei were processed correctly throughout the dA tailing, ligation, and coupling steps; a small portion of the beads were used to check for PCR amplification from the universal barcodes FIG. 4, panel B. The remainder of the beads were then processed using the split-and-pool barcoding method through five rounds of barcoding before PCR amplification (FIG. 4, panel C).

Figure 5:
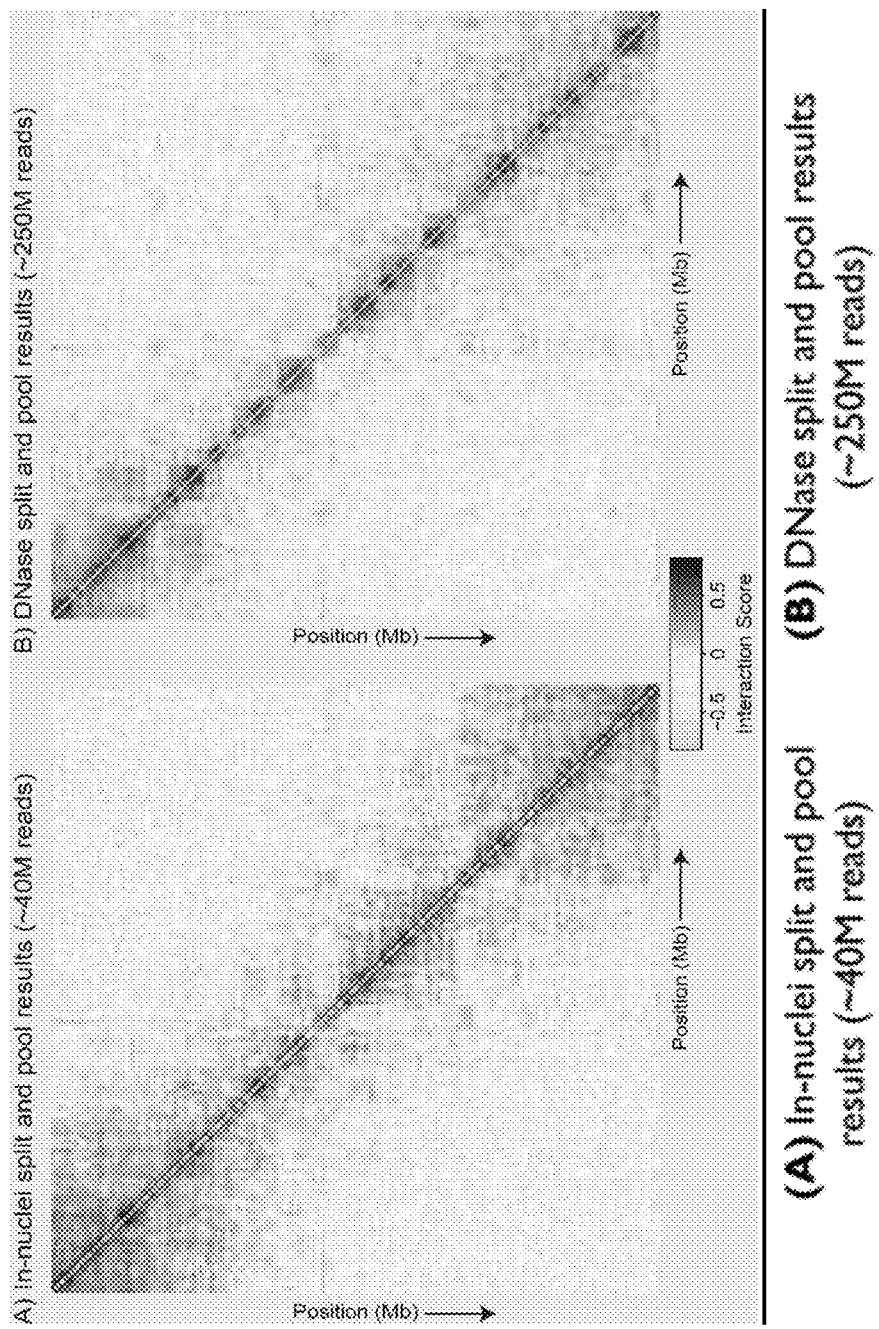
FIG. 5 shows a gray scale version of heat maps comparing the observed interactions in chromosome 1 at the megabase scale between samples prepared using in-nuclei ligation (A) according to one embodiment of the current disclosure or using DNase treatment (B).

Upon successful split-and-pool barcoding, the amount of template attached to beads was quantified by amplifying the contents of 1% of the beads for 13 cycles, and checking the concentration of the resultant DNA using an Agilent Bioanalyzer. A 2.5% portion of the sample representing 20M unique fragments was then submitted for 200-cycle Hi-seq, aiming for 2× coverage. The resultant sequencing reads were analyzed by grouping together aligned sequences based on barcode, and preparing heat maps based on the frequency of interactions among the Mb regions of each chromosome (FIG. 5, panel A). As expected, the sequencing run showed most interactions occurred along the diagonal; however, there are a number of areas that have a higher density of interactions, and we also observed a number of off-diagonal structures. Overall, the sequencing results share many of the same features of the DNase nuclear preparation method described earlier (FIG. 5, panel B).

Figure 6:
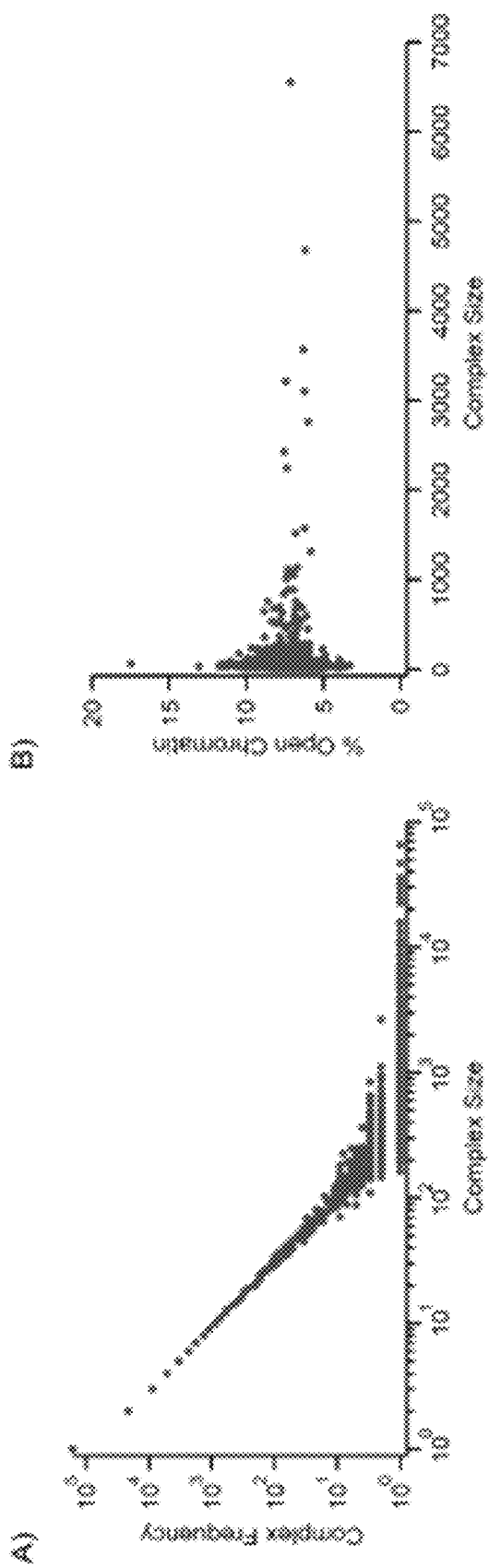
FIG. 6 shows plots of the sizes of sequenced complexes as a factor of complex frequency and as a factor of the percentage of open chromatin. Panel (A): Complex frequency (the number of times a complex of a specific size was observed by sequencing) compared to its size. Panel (B): The percentage of open chromatin as a function of complex size.

FIG. 6, panel A shows that the largest complex size in the dataset analyzed contained 65,523 sequences, which equates to 2,146,599,003 contact pairs. In contrast, there are only 21,197 complexes that contain two sequences equating to 21,197 contact pairs (FIG. 6, panel A). Therefore, there are five orders of magnitude more pair-wise interactions identified in a complex of many fragments, compared with a large number of smaller complexes.

To validate that closed chromatin did not lead to the generation of higher order complexes, the complex size was compared to the percentage of open chromatin in a complex as defined by DNase hypersensitivity datasets. It is observed that percentage of open chromatin does not correlate with the size of complexes (FIG. 6, panel B).

Figure 8:
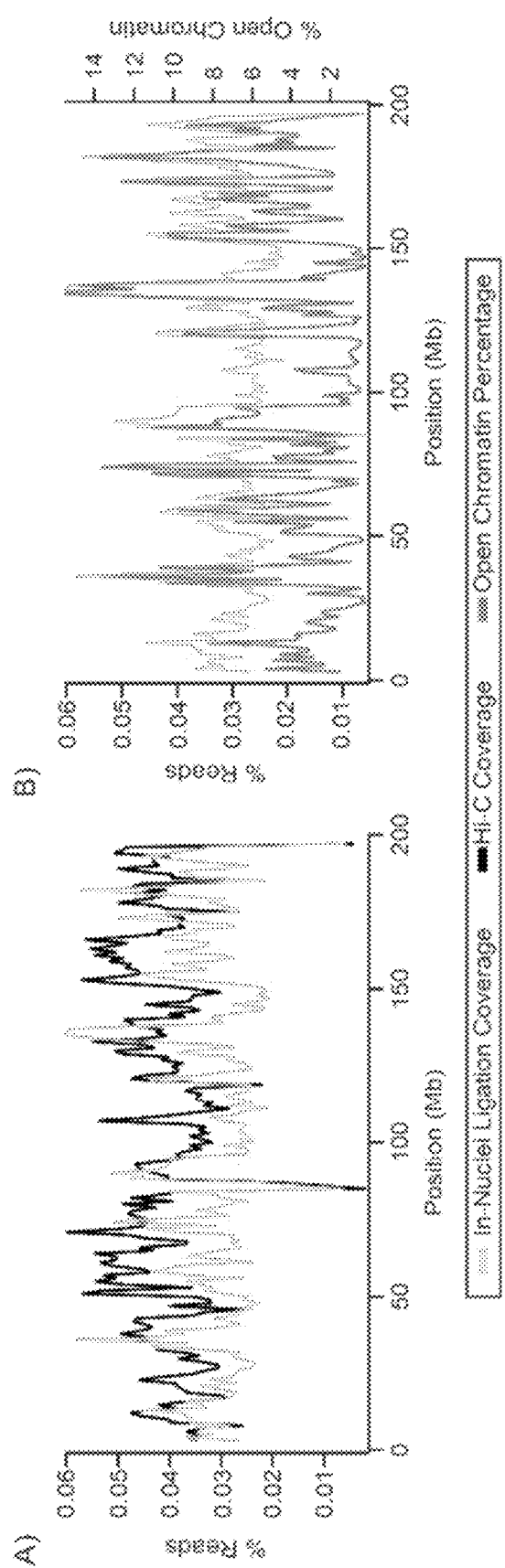
FIG. 8 shows the sequencing coverage as denoted by the percentage of reads of total reads contained within Mb bins of chromosome 1 from in-nuclei ligation compared to the sequencing coverage of Hi-C (A) and the percentage of open chromatin by DNase hypersensitivity (B) testing.

In order to test whether or not the large complexes observed above were known compartments such as the nucleolus, the coverage across each of the clusters can be determined of which chromosomes are represented. If these structures are nucleoli, it would be expected that they would be enriched in chromosomes 12, 15, 16, 17, 18, and 19. [64] The analysis was first performed by taking all clusters which contained greater than 10,000 fragments, determining the representative numbers of fragments from each chromosome, normalizing to the number of expected fragments based on that chromosome size, and calculating a percent representation (FIG. 7, panel A). This was then repeated on just the largest cluster (FIG. 8, panel A). As can be seen, there is no significant variation between the chromosomes which decreases the likelihood that these large clusters are representative of nucleoli.

To determine whether sample was lost during processing, read coverage was analyzed. This allows to detect regions of chromatin that are not represented and thus determine whether sample was lost. The coverage from in-nuclei ligation of chromosome 1 was determined to be suitable (FIG. 9). Hi-C is an alternative sequencing preparation method that has the potential to compare well with our results because both methods use restriction digest to fragment chromatin. The read coverage of these two methods showed some similar peaks and troughs across chromosome 1 (FIG. 9, panel A), however, there is a much stronger correlation to DNase hypersensitivity data (FIG. 9, panel B). This suggests that the cutting frequency of our restriction digest is limited mainly in regions of closed chromatin due to blockage of recognition sites, which is less likely to occur in sections of open chromatin. It should be noted, however, that even in the case of sections of chromatin with chiefly closed regions, a suitable read coverage is still observed.

Example 16: Split and Pool Barcoding of Isolated Nuclei

Cells were prepared via lysis, nuclear poration, restriction digestion with HpyCH4V in nuclei, dA tailing in nuclei. Cells were then counted and stochastically loaded onto either a well plate (a) or a SlipChip device (b). Cells were mixed with 20 nM adapters, and ligated with 1× NEB Instant Sticky Ligase Mix. After 6 hours of ligation, cells were lysed with a urea-based lysis buffer and coupled to Pierce NHS-activated beads overnight.

Following bead coupling, beads were washed, dummy-barcoded with a y-end adapter, and then decoupled at high 60 C for an hour with Proteinase K. Finally, these products were amplified with y-end specific primers and run on a 1% gel for library quality assessment.

Figure 10:
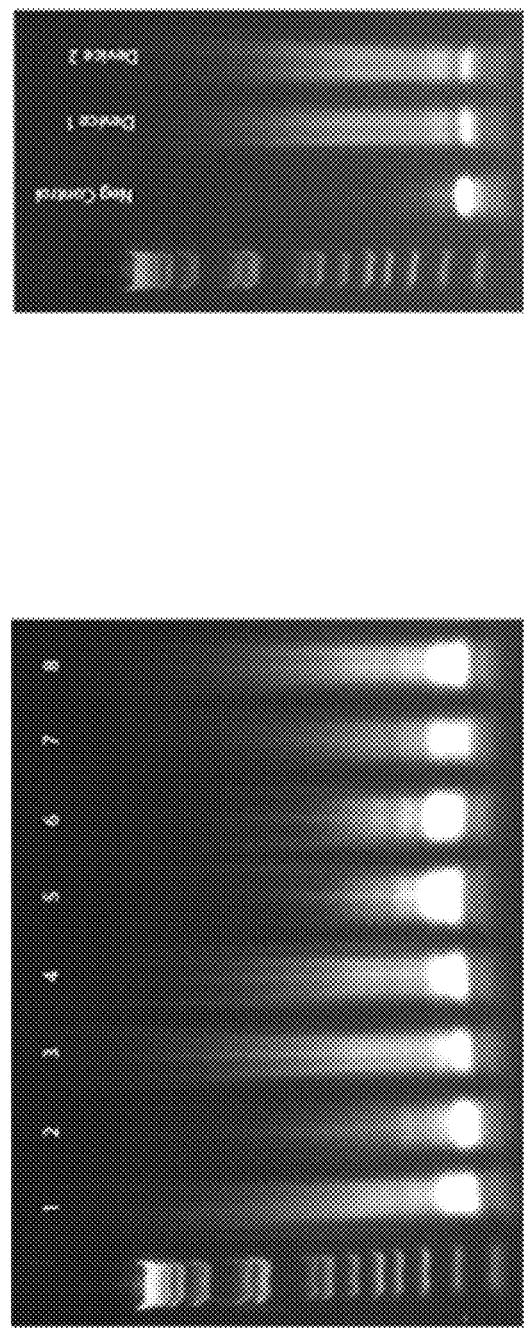
FIG. 10 shows a gel electrophoresis of libraries of barcoded complexes obtained with a method of the present disclosure. In particular, FIG. 10 Panel A shows a gel of libraries from individual single cells that were Poisson loaded to 60% occupancy on 16 wells of a 96-well plate (of which, 8 wells are shown), barcoded and amplified separately.

The results are reported in FIG. 10 which shows cells prepared via lysis, nuclear poration, restriction digestion with HpyCH4V in nuclei, dA tailing in nuclei. Cells were then counted and stochastically loaded onto either a well plate (FIG. 10 Panel a) or aSlipChip device (FIG. 10 Panel b). Cells were mixed with 20 nM adapters, and ligated with 1×NEB Instant Sticky Ligase Mix. After 6 hours of ligation, cells were lysed with a urea-based lysis buffer and coupled to Pierce NHS activated beads overnight. Following bead coupling, beads were washed, dummy-barcoded with a y-end adapter, and then decoupled at high 60 C for an hour with Proteinase K. Finally, these products were amplified with y-end specific primers and run on a 1% gel for library quality assessment.

Example 17: Mitochondrial Preparation

MtDNA chromosome conformation studies will be done using the GM12878 human cell line, a cell line that has been studied extensively in previous genome organization studies. Cells will be lysed using a hypotonic lysis buffer (HLB) to break the cell membranes while keeping the organelles intact. Following lysis, a light centrifugation will be done (approx. 1,000 g) to pellet denser organelles (e.g. nuclei). The supernatant containing mitochondria will be recovered and centrifuged at a higher rate (approx. 15,000 g) to pellet and isolate mitochondria. Spatial information in mtDNA will be preserved through formaldehyde crosslinking. Mitochondria will then be lysed and subjected to a more generic restriction enzyme treatment than seen with previous chromosome conformation methods. Given human mitochondrial genomes are approximately 16,000 bp long, using a specific 4 bp cutter such as HpyCH4V will cut every 256 bp, resulting in a maximum of 62.5 different complexes. This may provide vague information about mtDNA organization, as it is not enough to resolve structural domains and other existing features. Using a more generic digest enzyme such as CviJI (recognizes RGCY sites (R=purine, Y=pyrimidine)) would result in cuts every 64 bp, resulting in a maximum of 250 different complexes. These complexes will then be coupled to N-hydroxysuccimide magnetic beads at a ratio of 1:4 (one complex per every 4 beads) to ensure a 1:1 mapping between the complexes and beads.

Example 18: Method to Provide in-Mitochondrion Nucleic Acid and/or Protein Complexes to Analyze Chromosome Structures To uniquely identify the chromosomal fragments of mtDNA that comprise each complex, a combinatorial barcoding approach will be carried out. This will allow one to capture all pairwise interactions that are preserved in each complexes by matching the barcode sequences attached to each chromosomal fragment instead of using proximity ligation, which has its limitations. The coupled beads will be split across a 96-well plate, with each well containing a different barcode sequence. Following ligation of the first barcode, the beads will be mixed and split over another 96-well plate, which contains barcodes that specifically ligate to the overhang sequence of the previous barcode sequence to prevent the formation of chimeric sequences.

While this method would ideally need to be carried out twice to generate enough unique barcode combinations ($96^2$=9216 different combinations, which far exceeds the 250 complexes theoretically calculated), this would imply that this method is conducted over a maximum of 4 cells as a cell may contain up to 2000 different mitochondria. To increase throughput and to prevent misidentification by tagging the same barcode onto DNA in two different complexes, a minimum of 3 rounds of combinatorial barcoding will be conducted ($96^3$=8.85×10$^5$ different combinations), allowing one to apply this method with up to 440 different cells.

Following barcoding, complexes will be reverse crosslinked, amplified using PCR, and submitted for paired-end next generation sequencing to reconstruct the spatial organization of the mitochondrial genome.

Example 19: Method to Provide in-Mitochondrion Nucleic Acid and/or Protein Complexes to Analyze the Influence of Gene Expression on Mitochondrial Genome Organization To understand how mitochondrial gene expression is influenced in genome organization, one can assess how application of transcriptional inhibitors affects the mitochondrial genome. Cells will be treated with ethidium bromide, which has been demonstrated previously to halt mitochondrial transcription. After treatment, excess ethidium bromide will be washed from the cells, and mitochondrial extraction and crosslinking will be done as described previously. Based on their suspected origins as bacterial DNA, domains should be present in mitochondrial DNA that are composed of regions of supercoiling (plectenemes) and separated by plecteneme-free regions under normal conditions. In the presence of ethidium bromide, domain boundaries are expected to be disrupted, which signifies the overall disruption of mtDNA transcription. However, the overall structure of the chromosome should be conserved. These results would be reflected in heat map images from sequencing data, where triangular regions reflecting domain regions would be absent.

Example 20: Method to Provide in-Mitochondrion Nucleic Acid and/or Protein Complexes to Analyze Disruption of Nuclear Processes on Mitochondrial Genome Organization The nucleus-mitochondria relationship is important in upholding mitochondrial function. Most proteins that reside in mitochondria are transcribed from the nucleus and imported into mitochondria following post-translational modifications. One example highlighting this relationship regards mitochondria's transcriptional machinery. Regulation of mitochondrial gene expression is managed by Polrmt, Tfam, and Tfb2m, three proteins whose genes reside in the nucleus. Polrmt is the equivalent RNA polymerase in mitochondria for transcribing mtDNA while Tfam and Tfb2m are initiation factors that aid Polrmt in transcription. The expression of these genes are influenced by the nuclear transcription factor NRF-1 and nearby estrogen receptors.

One of these proteins that appears key in mitochondrial organization is Tfam. Tfam has been demonstrated in previous studies to aid mtDNA organization though the compaction of DNA and formation of nucleoid structures. Since Tfam is only transcribed in the nucleus, it would suggest that the nucleus is a key player in not only exporting proteins in maintaining mitochondrial function, but also in supporting mitochondrial genome organization.

To highlight the nucleus' role in regulating mitochondrial gene expression, knockdown of Tfam will be done to greatly reduce Tfam protein levels. Following knockdown, standard methodology as presented previously will be done to reconstruct the mitochondrial genome. Because of the impacts Tfam has on transcription, it is possible that domain features that would otherwise be present would be suppressed. This would be compared against the wild type case to see how these features would differ, and to emphasize the relationship in the nucleus in supporting mitochondrial function.

Example 21: Spatial Reconstruction of Mitochondrial Genome

Figure 23:
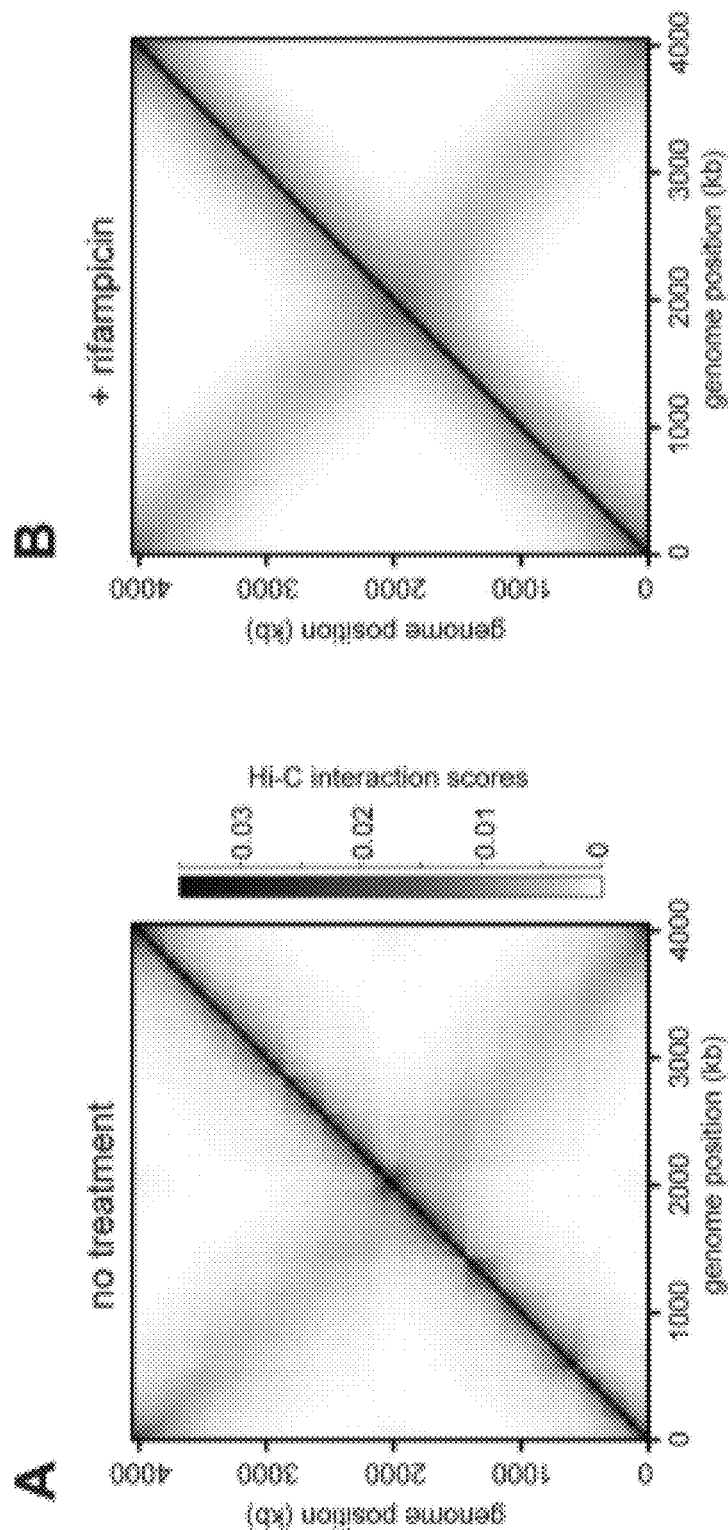
FIG. 23 shows a spatial chromosomal reconstruction from swarmer *Caulobacter crescentus* bacteria.

Heat map generation of mtDNA sequencing data will be done to provide the first look of spatial mitochondrial genome organization. Since mitochondria were thought to have originated from bacterial cells, one should expect the genome organization to resemble that of bacteria, where one diagonal contains the prominent interactions from loci in the same chromosome arm, while the other diagonal reflects inter-arm loci contacts, as reflected by Le et al. (FIG. 23A). This also is supported by what has been seen with microscopy, where mtDNA appears to be arranged as a circular-like chromosome, similar to what is seen in bacteria.[24] Since these arms appear to be independent of each other in gene production, the strength of the inter-arm diagonal should be weaker than that of the intra-arm diagonal.

Figure 24:
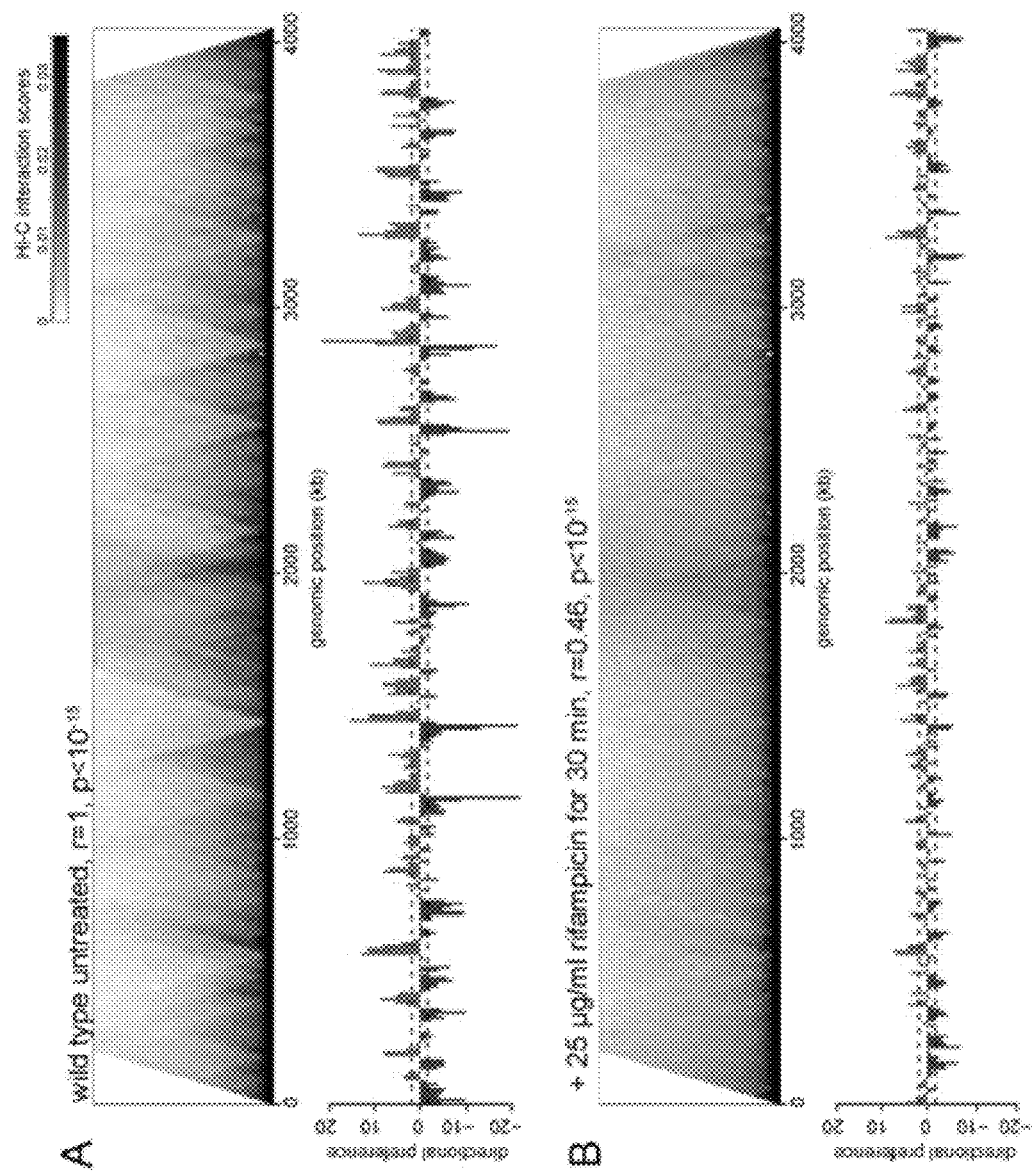
FIG. 24 shows normalized Hi-C maps highlighting the presence and absence of CID regions for untreated and rifampicin treated, respectively, from swarmer *C. crescentus* bacteria. (Figure S18 from Le et al [3]))
Figure 29:
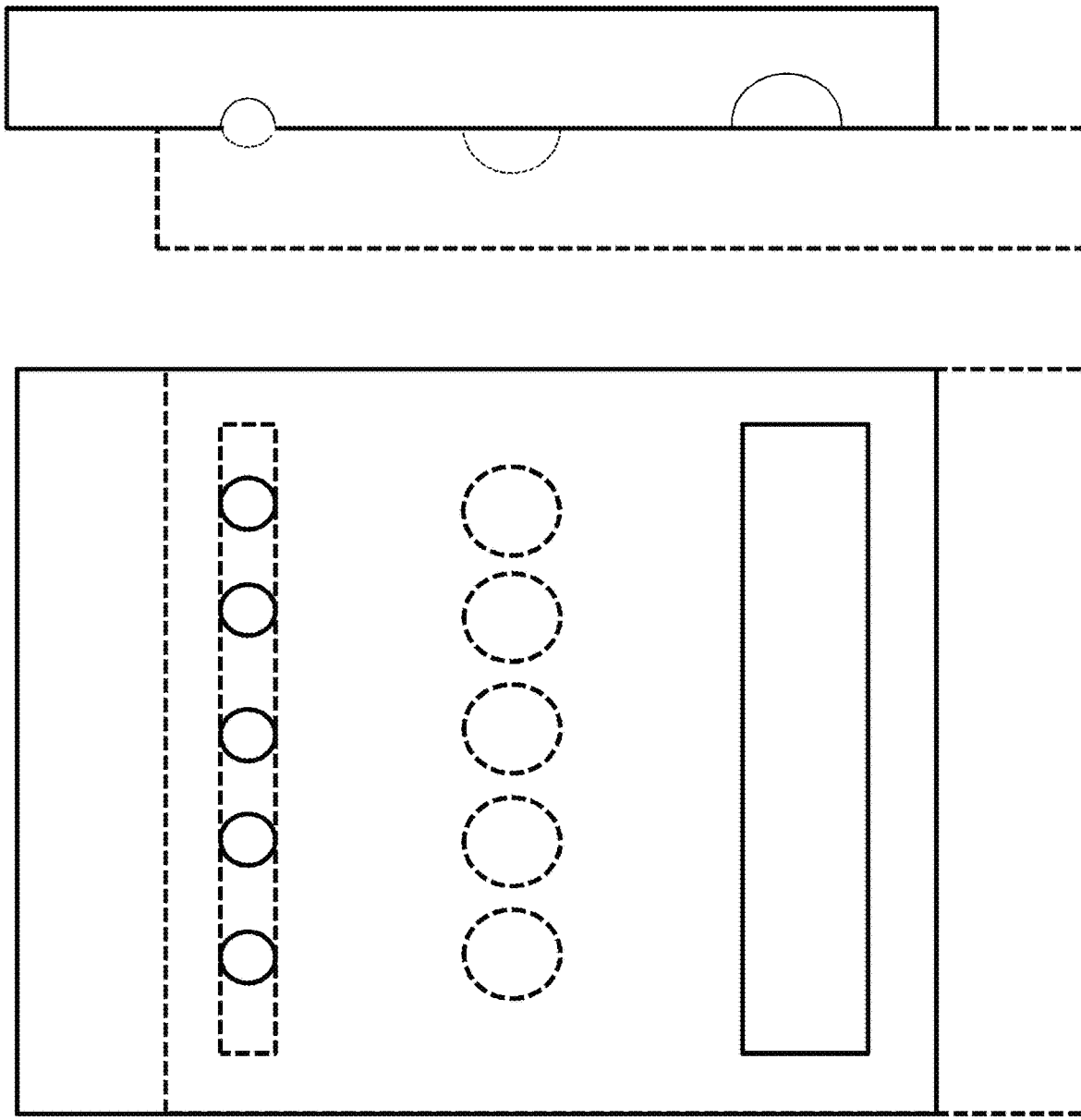
FIG. 29 shows an exemplary device (not to scale) for methods and systems herein described where the barcoding is performed on a single cell. In the illustration of FIG. 29, the device is in position to load loading wells, side (cross-sectional) and top views.
Figure 30:
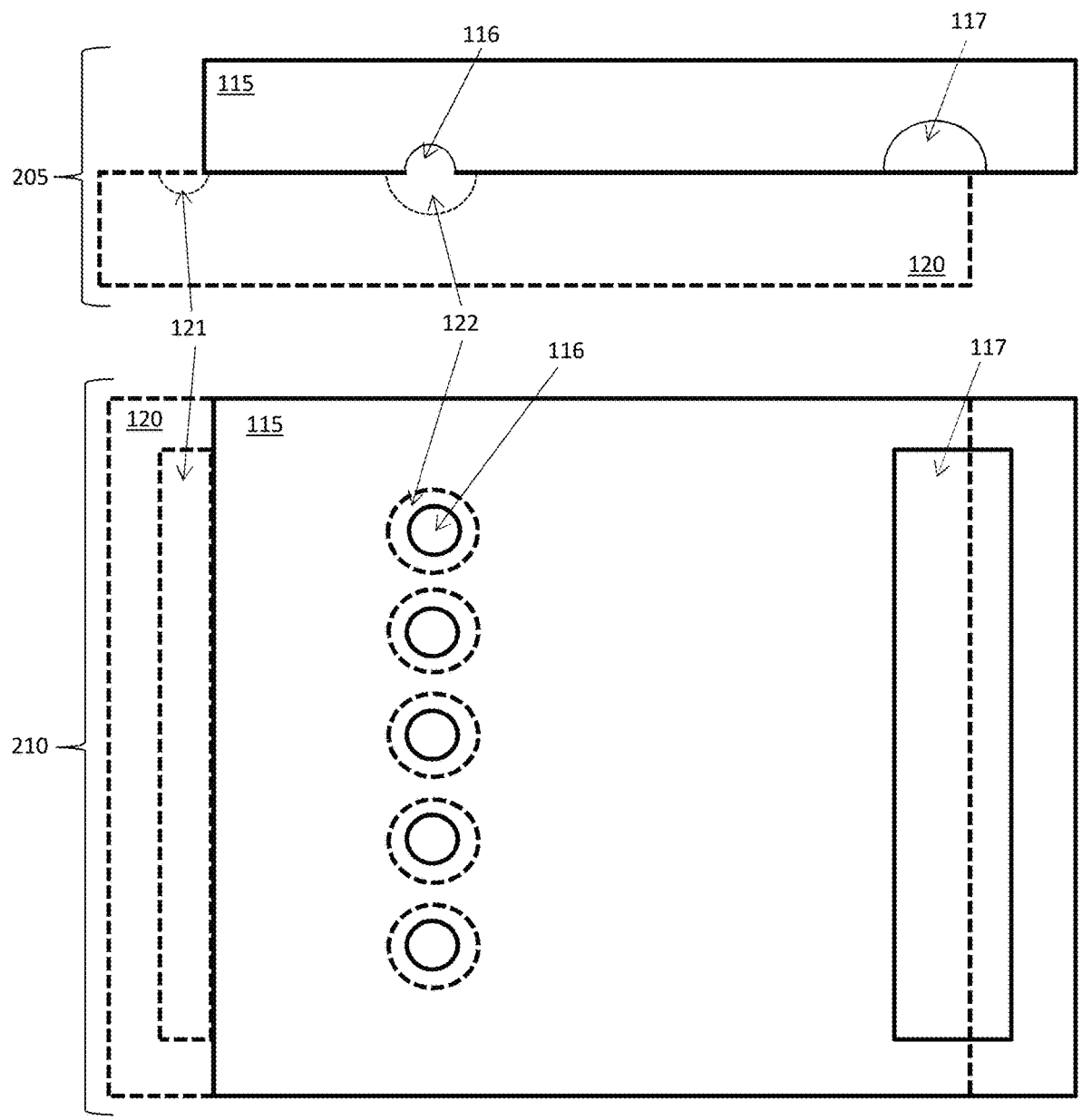
FIG. 30 shows the example device of FIG. 29 in position to drop in from loading wells to pooling wells, side (cross-sectional) and corresponding top views.
Figure 31A:
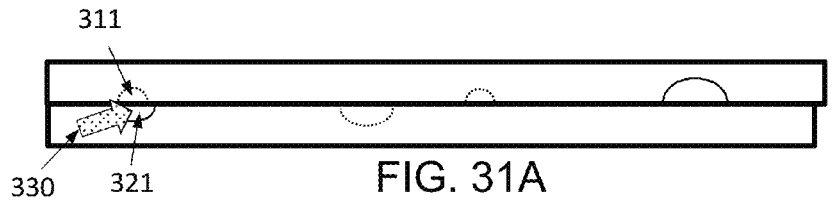
FIGS. 31A-31F shows an exemplary use of an exemplary (not to scale) device, for methods and systems herein described where the barcoding is performed on a single cell. In the illustration of FIGS. 31A-31F, the device is shown in side (cross sectional) view.
Figure 31B:
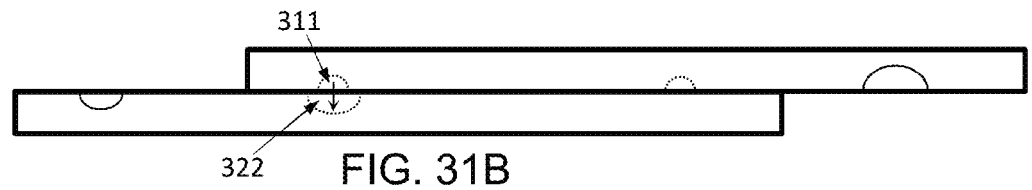
Figure 31C:
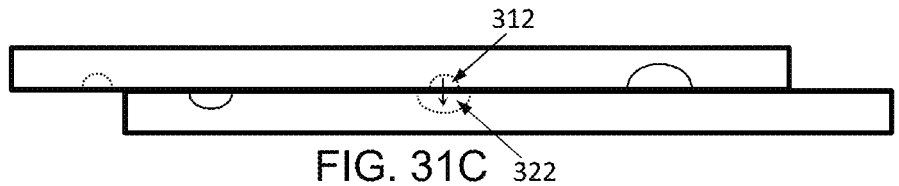
Figure 31D:
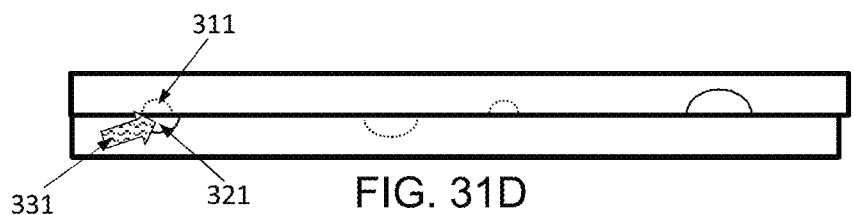
Figure 31E:
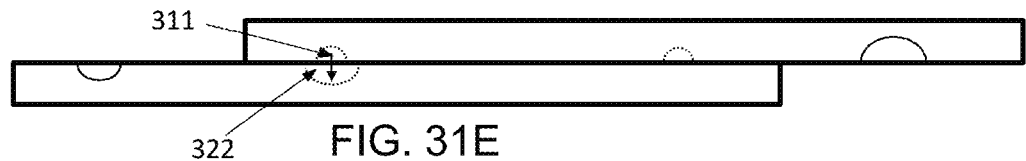
Figure 31F:
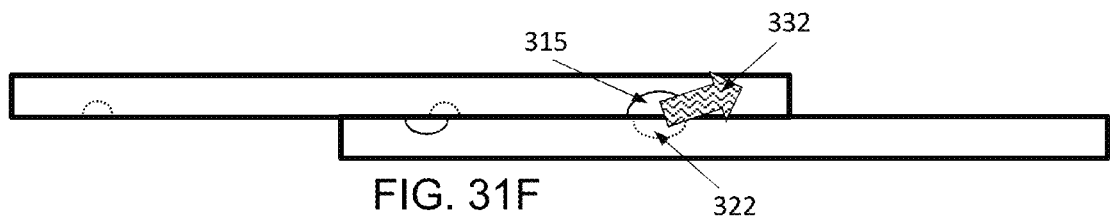

Furthermore, one would expect there to be similar structural domains in the mitochondrial genome similar to chromosomal interaction domains (CIDs) in bacterial chromosomes. As reflected in Le et al., plecteneme-like structures emerge from the genome to indicate regions of dense self-interaction regions (FIG. 23A, 24A). Furthermore, these plectoneme regions resemble that of "bottle brush fiber" organization, which demonstrates that these regions are not likely to interact with neighboring CIDs as they are restricted by boundaries between each CID. However, the stability of CIDs is aided by HU, a histone-like protein identified in bacteria. Like bacteria, mitochondria contain their own histone-like protein, termed HM. It has been exhibited that HM introduces supercoiling in mitochondria, similar to what histones and HUs do in nuclear and bacterial genomes, respectively. Therefore, plectoneme-like domains should emerge in mtDNA organization, with similar boundary formation to separate each domain region.

It is worth noting that the spatial reconstruction of the mitochondria would be demonstrative of a population averaging of structural features across numerous organelles. However, while eukaryotic and prokaryotic cells only contain one genomic copy of DNA, mitochondria carry anywhere between 1-15 copies of DNA per organelle. These copies may not exactly be identical due to heteroplasmy, where multiple mtDNA variants may coexist in the same organelle. The heat maps may reflect the general features associated with normal mtDNA expression, but this could also introduce some features that might be reflective of mtDNA variants, depending on the degree of heteroplasmy.

When transcription was disrupted in bacterial cells, while the general construction of the chromosome remained intact, the presence of CIDs was absent (FIG. 23B, 24B). Boundaries were constructed to separate domains of highly expressed genes, but in the absence of transcription, there appeared to be no traces of boundary regions. However, the lack of boundary regions also coincides with the lack of domain preservation. One should expect to see something similar in the inhibition of mitochondrial transcription. Since ethidium bromide halts all gene expression, structural domains should collapse similarly to the effect that rifampicin had on bacterial cells. Furthermore, the overall structure of the genome should be preserved, which should be reflected in similar diagonal traces on the heat map.

Similarly, one would expect disruption of domain formation when key proteins imported from the nucleus is interrupted. There may still be some domain formation based on a population averaging of all mitochondria, but there should be significant reduction in the degree of domain expression on the heat maps. The overall chromosome should remain intact assuming the overall structure of DNA is not impacted by the lack of Tfam, leading to a similar heat map diagonal highlighting both the heavy and light strands. This effect on genome organization would highlight the importance of nucleus-mitochondria relationship in ensuring proper mitochondrial structure and function.

In summary, methods and systems are provided and related compositions to perform single-cell marking of a nucleic acid and/or protein in a sample based on in-cell or in-organelle barcoding of nucleic acid and/or protein complexes of the cell or organelle; the methods and systems herein described are configured to provide in-cell or in-organelle single-cell marked nucleic acid and/or protein complexes comprising a single-cell, cell-specific, or a single-cell organelle-specific marker.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and systems according to various embodiments and scope of the claims.

All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P2266-US-Seq-List ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Quinodoz, S. A., et al., *Higher-Order Inter-chromosomal Hubs Shape 3D Genome Organization in the Nucleus*. Cell, 2018. 174(3): p. 744-757.e24.
2. Taanman, J. W., *The mitochondrial genome: structure, transcription, translation and replication*. Biochim Biophys Acta, 1999. 1410(2): p. 103-23.
3. Le, T. B., et al., *High-resolution mapping of the spatial organization of a bacterial chromosome*. Science, 2013. 342(6159): p. 731-4.
4. Soderberg, O., et al., *Direct observation of individual endogenous protein complexes in situ by proximity ligation*. Nat Methods, 2006. 3(12): p. 995-1000.
5. Ramani, V., R. Qiu, and J. Shendure, *High-throughput determination of RNA structure by proximity ligation*. Nat Biotechnol, 2015. 33(9): p. 980-4.
6. Dekker, J., et al., *Capturing chromosome conformation*. Science, 2002. 295(5558): p. 1306-11.
7. Weibrecht, I., et al., *Proximity ligation assays: a recent addition to the proteomics toolbox*. Expert Review of Proteomics, 2010. 7(3): p. 401-409.
8. Greenwood, C., et al., *Proximity assays for sensitive quantification of proteins*. Biomolecular Detection and Quantification, 2015. 4: p. 10-16.
9. G-Biosciences, *Detergents: Handbook & Selection Guide to Detergents & Detergent Removal*. 2018, Geno Technology Inc.
10. Neugebauer, J. M., [18] *Detergents: An overview, in Methods in Enzymology*, M. P. Deutscher, Editor. 1990, Academic Press. p. 239-253.
11. Schramm, L. L., E. N. Stasiuk, and D. G. Marangoni, 2 *Surfactants and their applications*. Annual Reports Section "C" (Physical Chemistry), 2003. 99(0): p. 3-48.
12. Bindu, S., D. DSomashekar, and R. Joseph, *A comparative study on permeabilization treatments for in situ determination of phytase of Rhodotorula gracilis*. Letters in Applied Microbiology, 1998. 27: p. 336-340.
13. Los, G. V., et al., *HaloTag: a novel protein labeling technology for cell imaging and protein analysis*. ACS Chem Biol, 2008. 3(6): p. 373-82.
14. Singh, V., et al., *Genetically encoded multispectral labeling of proteins with polyfluorophores on a DNA backbone*. J Am Chem Soc, 2013. 135(16): p. 6184-91.
15. Blackstock, D. and W. Chen, *Halo-tag mediated self-labeling of fluorescent proteins to molecular beacons for nucleic acid detection*. Chem Commun (Camb), 2014. 50(89): p. 13735-8.
16. Kozlov, I. A., et al., *Efficient strategies for the conjugation of oligonucleotides to antibodies enabling highly sensitive protein detection*. Biopolymers, 2004. 73(5): p. 621-30.
17. Richards, F. M. and J. R. Knowles, *Glutaraldehyde as a protein cross-linking reagent*. Journal of Molecular Biology, 1968. 37(1): p. 231-233.
18. Thermo Fisher Scientific Inc., *Instructions: Imidoester Crosslinkers: DMA, DMP, DMS, DTBP*. 2012: Rockford, Ill., USA.
19. Tian, B., J. Yang, and A. R. Brasier, *Two-step Crosslinking for Analysis of Protein-Chromatin Interactions*. Methods in molecular biology (Clifton, N.J.), 2012. 809: p. 105-120.
20. ProteoChem, *DSG Crosslinker Protocol and Product Information Sheet*. 2014: Loves Park, Ill., USA.
21. Hoffman, E. A., et al., *Formaldehyde crosslinking: a tool for the study of chromatin complexes*. J Biol Chem, 2015. 290(44): p. 26404-11.
22. Kennedy-Darling, J. and L. M. Smith, *Measuring the Formaldehyde Protein-DNA Cross-Link Reversal Rate*. Analytical Chemistry, 2014. 86(12): p. 5678-5681.
23. Wikipedia. *Crosslinking of DNA*. 2018 [cited 2018 Sep. 19, 2018]; Available from: https://en/wikipedia.org/wiki/Crosslinking_of_DNA.
24. Guainazzi, A. and O. D. Scharer, *Using synthetic DNA interstrand crosslinks to elucidate repair pathways and identify new therapeutic targets for cancer chemotherapy*. Cell Mol Life Sci, 2010. 67(21): p. 3683-97.
25. Coste, F., et al., *Crystal structure of a double-stranded DNA containing a cisplatin interstrand cross-link at 1.63 A resolution: hydration at the platinated site*. Nucleic Acids Research, 1999. 27(8): p. 1837-1846.
26. Chen, W., et al., *Reactive oxygen species (ROS) inducible DNA cross-linking agents and their effect on cancer cells and normal lymphocytes*. J Med Chem, 2014. 57(11): p. 4498-510.
27. Stone, M. P., et al., *Interstrand DNA cross-links induced by alpha, beta-unsaturated aldehydes derived from lipid peroxidation and environmental sources*. Acc Chem Res, 2008. 41(7): p. 793-804.

28. Kirchner, J. J., S. T. Sigurdsson, and P. B. Hopkins, *Interstrand cross-linking of duplex DNA by nitrous acid: covalent structure of the dG-to-dG cross-link at the sequence 5'-CG*. Journal of the American Chemical Society, 1992. 114(11): p. 4021-4027.
29. Engreitz, J. M., et al., *RNA-RNA interactions enable specific targeting of noncoding RNAs to nascent PremRNAs and chromatin sites*. Cell, 2014. 159(1): p. 188-199.
30. Harris, M. E. and E. L. Christian, *Chapter 7—RNA Crosslinking Methods*, in *Methods in Enzymology*. 2009, Academic Press. p. 127-146.
31. New England Biolabs. *Types of Restriction Endonucleases*. 2018 Sep. 19, 2018]; Available from: https://www.neb.com/products/restriction-endonucleases/restriction-endonucleases/types-of-restriction-endonucleases.
32. New England Biolabs. *Restriction Endonucleases*. 2018 Sep. 19, 2018]; Available from: https://www.neb.com/products/restriction-endonucleases.
33. Ramani, V., et al., *Mapping 3D genome architecture through in situ DNase Hi-C*. Nature Protocols, 2016. 11: p. 2104.
34. Ling, G. and D. J. Waxman, *DNase I Digestion of Isolated Nuclei for Genome-Wide Mapping of DNase Hypersensitivity Sites in Chromatin*. Methods in molecular biology (Clifton, N.J.), 2013. 977: p. 21-33.
35. Mótyán, J. A., F. Toth, and J. Tözsér, *Research Applications of Proteolytic Enzymes in Molecular Biology*. Biomolecules, 2013. 3(4): p. 923-942.
36. Du, W., et al., *SlipChip*. Lab on a Chip, 2009. 8: p. 2286-2292.
37. Ge, S., et al., *Digital, Ultrasensitive, End-Point Protein Measurements with Large Dynamic Range via Brownian Trapping with Drift*. J Am Chem Soc, 2014. 136(42): p. 14662-14665.
38. Li, L., et al., *Dead-end filling of SlipChip evaluated theoretically and experimentally as a function of the surface chemistry and the gap size between the plates for lubricated and dry SlipChips*. Langmuir, 2010. 26(14): p. 12465-71.
39. Liu, W., et al., *SlipChip for immunoassays in nanoliter volumes*. Anal Chem, 2010. 82(8): p. 3276-82.
40. Ma, L., et al., *Individually addressable arrays of replica microbial cultures enabled by splitting SlipChips*. Integr Biol (Camb), 2014. 6(8): p. 796-805.
41. Ma, L., et al., *Gene-targeted microfluidic cultivation validated by isolation of a gut bacterium listed in Human Microbiome Project's Most Wanted taxa*. Proc Natl Acad Sci USA, 2014. 111(27): p. 9768-73.
42. Selck, D. A., et al., *Increased robustness of singlemolecule counting with microfluidics, digital isothermal amplification, and a mobile phone versus real-time kinetic measurements*. Anal Chem, 2013. 85(22): p. 11129-36.
43. Shen, F., et al., *Digital Isothermal Quantification of Nucleic Acids via Simultaneous Chemical Initiation of Recombinase Polymerase Amplification Reactions on SlipChip*. Analytical Chemistry, 2011. 83(9): p. 3533-3540.
44. Shen, F., et al., *Nanoliter multiplexed PCR arrays on a SlipChip*. Analytical Chemistry, 2010. 82: p. 4606-4612.
45. Shen, F., et al., *Digital PCR on a SlipChip*. Lab on a Chip, 2010. 10: p. 2666-2672.
46. Shen, F., et al., *Multiplexed quantification of nucleic acids with large dynamic range using multivolume digital RT-PCR on a rotational SlipChip tested with HIV and Hepatitis C viral load*. Journal of the American Chemical Society, 2011. 133(44): p. 17705-17712.
47. Sun, B., et al., *Measuring fate and rate of singlemolecule competition of amplification and restriction digestion, and its use for rapid genotyping tested with hepatitis C viral RNA*. Angew Chem Int Ed Engl, 2014. 53(31): p. 8088-92.
48. Sun, B., et al., *Mechanistic evaluation of the pros and cons of digital RT-LAMP for HIV-1 viral load quantification on a microfluidic device and improved efficiency via a two-step digital protocol*. Anal Chem, 2013. 85(3): p. 1540-6.
49. Rotem, A., et al., *Single-cell ChIP-seq reveals cell subpopulations defined by chromatin state*. Nat Biotechnol, 2015. 33(11): p. 1165-72.
50. Nilsson, J., et al., *Review of cell and particle trapping in microfluidic systems*. Anal Chim Acta, 2009. 649(2): p. 141-57.
51. Hosic, S., S. K. Murthy, and A. N. Koppes, *Microfluidic Sample Preparation for Single Cell Analysis*. Anal Chem, 2016. 88(1): p. 354-80.
52. Xin, Y., et al., *Use of the Fluidigm C1 platform for RNA sequencing of single mouse pancreatic islet cells*. Proc Natl Acad Sci USA, 2016. 113(12): p. 3293-8.
53. Yin, H. and D. Marshall, *Microfluidics for single cell analysis*. Curr Opin Biotechnol, 2012. 23(1): p. 110-9.
54. Collins, D. J., et al., *The Poisson distribution and beyond: methods for microfluidic droplet production and single cell encapsulation*. Lab Chip, 2015. 15(17): p. 3439-59.
55. Pamme, N., *Magnetism and microfluidics*. Lab Chip, 2006. 6(1): p. 24-38.
56. Lee, S. H., et al., *Effective mixing in a microfluidic chip using magnetic particles*. Lab Chip, 2009. 9(3): p. 479-82.
57. Nagano, T., et al., *Single-cell Hi-C reveals cell-to-cell variability in chromosome structure*. Nature, 2013. 502 (7469): p. 59-64.
58. Rao, S. S., et al., *A 3D map of the human genome at kilobase resolution reveals principles of chromatin looping*. Cell, 2014. 159(7): p. 1665-80.
59. Engreitz, J. M., et al., *The Xist lncRNA exploits threedimensional genome architecture to spread across the X chromosome*. Science, 2013. 341(6147): p. 1237973.
60. Sigma Aldrich. *Cell Dissociation with Trypsin*. 2018 Sep. 19, 2018]; Available from: https://www.sigmaldrich.com/technical-documents/articles/biology/cell-dissociation-with-trypsin.html.
61. Sigma Aldrich. *Removal of Adherent Cells from a Culture Surface Using Trypsin*. 2018 Sep. 19, 2018]; Available from: https://www.sigmaldrich.com/technical-documents/protocols/biology/removal-of adherent-cells.html.
62. Nagano, T., et al., *Single-cell Hi-C for genome-wide detection of chromatin interactions that occur simultaneously in a single cell*. Nat Protoc, 2015. 10(12): p. 1986-2003.
63. Nagano, T., et al., *Comparison of Hi-C results using in-solution versus in-nucleus ligation*. Genome Biol, 2015. 16: p. 175.
64. Dev, V. G., et al., *Nucleolus organizers in Mus musculus subspecies and in the RAG mouse cell line*. Genetics, 1977. 86(2 Pt. 1): p. 389-98.

The invention claimed is:

1. A method to perform single-cell marking of a nucleic acid and/or protein in a sample comprising a plurality of cells, the method comprising:
   crosslinking a cell from the plurality of cells to provide a crosslinked cell comprising a crosslinked nucleic acid and/or protein material,
   permeabilizing the crosslinked cell or an organelle thereof, to provide a permeabilized cell or organelle thereof;
   in cell or in-organelle fragmenting the crosslinked nucleic acid and/or protein material to provide molecular complexes each comprising fragmented crosslinked nucleic acid and/or protein material
   in-cell or in-organelle attaching a series of tags to a nucleic acid and/or protein in the molecular complexes of the permeabilized cell or organelle thereof, following the in-cell or in-organelle fragmenting,
      to provide a barcoded cell or organelle comprising in-cell or in-organelle single-cell or single organelle marked molecular complexes of the cell comprising a nucleic acid and/or protein complexes each comprising nucleic acids and/or proteins barcoded with a single-cell or single-organelle specific marker,
   lysing the barcoded cell or organelle to provide a barcoded cell or organelle lysate comprising a mixture of single-cell or single-organelle marked molecular complexes and
   attaching a series of tags to nucleic acids and/or proteins in the mixture of single-cell or single-organelle marked molecular complexes to obtain a plurality of single-cell marked molecular complexes each comprising nucleic acids and/or proteins barcoded with a single-cell or single-organelle specific and complex-specific barcode
   wherein the attaching a series of tags is performed by split-and-pool sequential direct covalent linkage, to the nucleic acids and/or proteins, of a tag with another tag, to form a barcode comprising a series of two or more tags directly attached one to another through covalent linkage.

2. The method of claim 1, wherein the in-cell or in-organelle attaching a series of tags is performed without performing an enzymatic intracomplex ligation step directed to include a covalent linkage between two nucleic acids and/or proteins which are attached to one another within a complex.

3. The method of claim 1, wherein
   the permeabilizing is performed by permeabilizing the organelle thereof; and
   the in-cell or in-organelle attaching a series of tags is performed in-organelle,
   to provide a barcoded organelle comprising single-cell marked molecular complexes comprising a nucleic acid and/or protein barcoded with a single-cell organelle specific marker.

4. The method of claim 3, wherein the method further comprises,
   isolating the organelle thereof from the cell, the isolating performed before the crosslinking.

5. The method of claim 3, wherein the method further comprises,
   isolating the cell from the plurality of cells before crosslinking the cell to provide a crosslinked cell.

6. The method of claim 5, wherein the method further comprises,
   isolating the organelle thereof from the cell, the isolating performed after isolating the cell and before the crosslinking.

7. The method of claim 3, wherein the organelle is a single organelle from a single cell of the plurality of cells and the in-organelle barcoding is performed by ligating a barcode comprising a single tag to the nucleic acid and/or protein in the molecular complexes.

8. The method of claim 3, wherein the organelle is a plurality of organelles each from a single cell of the plurality of cells and the in-organelle barcoding is performed by in organelle split and pool barcoding the molecular complexes of each organelle of the plurality of organelles.

9. The method of claim 1, wherein the organelle is a nucleus, a mitochondrion and/or a chloroplast.

10. The method of claim 9, wherein the permeabilizing is performed by permeabilizing the cell; and the in-cell or in-organelle attaching a series of tags is performed in-cell, and wherein the barcoded cell comprises single-cell marked molecular complexes comprising a nucleic acid and/or protein barcoded with a single-cell marker.

11. The method of claim 9, wherein the method further comprises, before the crosslinking:

isolating the cell from the plurality of cells to provide an isolated cell, the isolating performed before the crosslinking, and wherein the crosslinking a cell from the plurality of cells is performed on the isolated cell.

12. The method of claim 10, wherein the cell is a single cell of the plurality of cells and the in-cell barcoding is performed by ligating a barcode comprising a single tag to the nuclei acid and/or protein in the molecular complexes of the permeabilized cell.

13. The method of claim 10, wherein the cell is a plurality of cells and the in-cell barcoding is performed by in-cell split and pool barcoding the molecular complexes of each cell.

14. The method of claim 1 wherein the method further comprises, isolating the cell from the plurality of cells before crosslinking the cell to provide a crosslinked cell.

15. The method of claim 1 wherein the in-cell or in-organelle barcoding is performed by in-cell or in-organelle barcoding a nucleic acid of nucleic acid complexes and/or nucleic acid protein complexes.

16. The method of claim 1 wherein the in-cell or in-organelle barcoding is performed by in-cell or in-organelle barcoding a protein of protein complexes and/or nucleic acid protein complexes.

17. The method of claim 1, wherein:

the in-cell or in-organelle attaching a series of tags is performed by attaching a series of tags to a ribonucleic acid of the molecular complexes.

* * * * *